US012727993B2

United States Patent
Mitra

(12) United States Patent
(10) Patent No.: US 12,727,993 B2
(45) Date of Patent: Sep. 8, 2026

(54) EXPANDABLE SEALING SKIRT TECHNOLOGY FOR LEAK-PROOF ENDOVASCULAR PROSTHESES

(71) Applicant: Endoluminal Sciences Pty Ltd., Eveleigh (AU)

(72) Inventor: Ashish Mitra, Bondi (AU)

(73) Assignee: Endoluminal Sciences Pty Ltd., Eveleigh (AU)

( * ) Notice: Subject to any disclaimer, the term of this patent is extended or adjusted under 35 U.S.C. 154(b) by 0 days.

(21) Appl. No.: 16/759,986

(22) PCT Filed: Oct. 29, 2018

(86) PCT No.: PCT/IB2018/001400
§ 371 (c)(1),
(2) Date: Apr. 28, 2020

(87) PCT Pub. No.: WO2019/086958
PCT Pub. Date: May 9, 2019

(65) Prior Publication Data
US 2020/0337837 A1 Oct. 29, 2020

Related U.S. Application Data

(60) Provisional application No. 62/674,522, filed on May 21, 2018, provisional application No. 62/674,519,
(Continued)

(51) Int. Cl.
*A61F 2/24* (2006.01)
*A61F 2/07* (2013.01)

(52) U.S. Cl.
CPC .............. *A61F 2/2418* (2013.01); *A61F 2/07* (2013.01); *A61F 2/2433* (2013.01);
(Continued)

(58) Field of Classification Search
None
See application file for complete search history.

(56) References Cited

U.S. PATENT DOCUMENTS 3,012,893 A 12/1961 Kremzner et al.
3,605,294 A 9/1971 Cunningham et al.
(Continued)

FOREIGN PATENT DOCUMENTS

CN 1264321 A 8/2000
CN 1578647 A 2/2005
(Continued)

OTHER PUBLICATIONS

AU2010206489 Examination Report No. 1 dated Jun. 18, 2012.
(Continued)

*Primary Examiner* — Ann Hu

(57) ABSTRACT

Disclosed herein are device assemblies for endovascular prosthesis implantation in a human patient comprising a collapsed delivery configuration and an expanded deployed configuration comprising: a stent frame comprising a plurality of expandable stent cells arranged in more than one layer and stacked in a longitudinal direction; a valve attached to the stent frame; and an expandable sealing skirt coupled to the stent frame, the expandable sealing skirt comprising a protruding region configured to expand radially past the stent frame when the device assembly is in the expanded deployed configuration and a non-protruding region.

38 Claims, 32 Drawing Sheets

Related U.S. Application Data filed on May 21, 2018, provisional application No. 62/674,517, filed on May 21, 2018, provisional application No. 62/674,515, filed on May 21, 2018, provisional application No. 62/674,510, filed on May 21, 2018, provisional application No. 62/579,005, filed on Oct. 30, 2017.

(52) U.S. Cl.
CPC .... *A61F 2/2436* (2013.01); *A61F 2230/0054* (2013.01); *A61F 2250/0023* (2013.01); *A61F 2250/0069* (2013.01)

(56) References Cited

U.S. PATENT DOCUMENTS 3,755,826 A 9/1973 Roberts
3,987,497 A 10/1976 Stoy et al.
4,059,552 A 11/1977 Zweigle et al.
4,106,129 A 8/1978 Carpentier et al.
4,352,883 A 10/1982 Lim
4,391,909 A 7/1983 Lim
4,407,957 A 10/1983 Lim
4,409,331 A 10/1983 Lim
4,673,566 A 6/1987 Goosen et al.
4,689,293 A 8/1987 Goosen et al.
4,744,933 A 5/1988 Rha et al.
4,749,620 A 6/1988 Rha et al.
4,806,355 A 2/1989 Goosen et al.
5,229,045 A 7/1993 Soldani
5,344,442 A 9/1994 Deac
5,354,330 A 10/1994 Hanson et al.
5,427,935 A 6/1995 Wang et al.
5,480,424 A 1/1996 Cox
5,499,995 A 3/1996 Teirstein et al.
5,500,015 A 3/1996 Deac
5,514,378 A 5/1996 Mikos et al.
5,536,274 A 7/1996 Neuss
5,609,626 A 3/1997 Quijano et al.
5,709,854 A 1/1998 Griffith-Cima et al.
5,713,950 A 2/1998 Cox
5,718,725 A 2/1998 Sterman et al.
5,769,882 A 6/1998 Fogarty et al.
5,797,960 A 8/1998 Stevens et al.
5,823,956 A 10/1998 Roth et al.
5,824,036 A * 10/1998 Lauterjung ............... A61F 2/07
623/1.13
6,029,671 A 2/2000 Stevens et al.
6,110,201 A 8/2000 Quijano et al.
6,123,723 A 9/2000 Konya et al.
6,129,761 A 10/2000 Hubbell
6,171,335 B1 1/2001 Wheatley et al.
6,217,278 B1 4/2001 Shiokawa et al.
6,254,564 B1 7/2001 Wilk et al.
6,271,278 B1 8/2001 Park et al.
6,287,334 B1 9/2001 Moll et al.
6,331,189 B1 12/2001 Wolinsky et al.
6,379,383 B1 4/2002 Palmaz et al.
6,398,758 B1 6/2002 Jacobsen et al.
6,406,493 B1 6/2002 Tu et al.
6,458,153 B1 10/2002 Bailey et al.
6,530,952 B2 3/2003 Vesely
6,537,310 B1 3/2003 Palmaz et al.
6,569,196 B1 5/2003 Vesely
6,572,652 B2 6/2003 Shaknovich
6,589,279 B1 7/2003 Anderson et al.
6,652,555 B1 11/2003 Vantassel et al.
6,682,558 B2 1/2004 Tu et al.
6,682,559 B2 1/2004 Myers et al.
6,695,865 B2 2/2004 Boyle et al.
6,719,787 B2 4/2004 Cox
6,733,525 B2 5/2004 Yang et al.
6,736,827 B1 5/2004 Mcandrew et al.
6,790,229 B1 9/2004 Berreklouw
6,805,711 B2 10/2004 Quijano et al.
6,830,584 B1 12/2004 Seguin
6,830,585 B1 12/2004 Artof et al.
6,830,586 B2 12/2004 Quijano et al.
6,849,085 B2 2/2005 Marton
6,858,229 B1 2/2005 Hubbell et al.
6,936,066 B2 8/2005 Palmaz et al.
7,044,966 B2 5/2006 Svanidze et al.
7,122,048 B2 10/2006 Dimatteo et al.
7,141,064 B2 11/2006 Scott et al.
7,179,290 B2 2/2007 Cao
7,195,641 B2 3/2007 Palmaz et al.
7,201,772 B2 4/2007 Schwammenthal et al.
7,217,287 B2 5/2007 Wilson et al.
7,276,078 B2 10/2007 Spenser et al.
7,318,278 B2 1/2008 Zhang et al.
7,331,991 B2 2/2008 Kheradvar et al.
7,331,993 B2 2/2008 White
7,338,484 B2 3/2008 Schoon et al.
7,361,189 B2 4/2008 Case et al.
7,364,585 B2 4/2008 Weber
7,371,258 B2 5/2008 Woo et al.
7,374,571 B2 5/2008 Pease et al.
7,402,171 B2 7/2008 Osborne et al.
7,410,499 B2 8/2008 Bicer
7,416,530 B2 8/2008 Turner et al.
7,422,603 B2 9/2008 Lane
7,431,733 B2 10/2008 Knight et al.
7,435,257 B2 10/2008 Lashinski et al.
7,455,689 B2 11/2008 Johnson
7,470,284 B2 12/2008 Lambrecht et al.
7,481,838 B2 1/2009 Carpentier et al.
7,500,989 B2 3/2009 Solem et al.
7,503,929 B2 3/2009 Johnson et al.
7,503,930 B2 3/2009 Sharkawy et al.
7,510,572 B2 3/2009 Gabbay
7,513,909 B2 4/2009 Lane et al.
7,534,261 B2 5/2009 Friedman
7,712,606 B2 5/2010 Salahieh et al.
7,790,194 B2 9/2010 Petersen
7,943,678 B2 5/2011 Heijkants et al.
7,955,372 B2 6/2011 Butterwick et al.
8,052,749 B2 11/2011 Salahieh et al.
8,062,352 B2 11/2011 Tittelbach et al.
8,083,768 B2 12/2011 Ginn et al.
8,231,890 B2 7/2012 Cruise et al.
8,313,504 B2 11/2012 Do et al.
8,465,779 B2 6/2013 Cruise et al.
8,814,928 B2 8/2014 Robin
9,216,076 B2 12/2015 Mitra et al.
11,263,354 B2 3/2022 Peck
2002/0064512 A1 5/2002 Petersen et al.
2002/0123790 A1 9/2002 White et al.
2002/0177890 A1 11/2002 Lenker
2002/0177894 A1 11/2002 Acosta et al.
2003/0040792 A1 2/2003 Gabbay
2003/0042186 A1 3/2003 Boyle
2003/0120332 A1 6/2003 Hartley
2003/0120333 A1 * 6/2003 Ouriel ....................... A61F 2/07
623/1.14
2003/0204235 A1 10/2003 Edens et al.
2003/0204249 A1 10/2003 Letort
2003/0208256 A1 11/2003 Dimatteo et al.
2003/0232895 A1 12/2003 Omidian et al.
2004/0093063 A1 5/2004 Wright et al.
2004/0106976 A1 6/2004 Bailey et al.
2004/0215338 A1 10/2004 Elkins et al.
2004/0260382 A1 12/2004 Fogarty et al.
2004/0260389 A1 12/2004 Case et al.
2005/0037050 A1 2/2005 Weber
2005/0043759 A1 2/2005 Chanduszko
2005/0070794 A1 3/2005 Deal et al.
2005/0137681 A1 6/2005 Shoemaker et al.
2005/0137688 A1 6/2005 Salahieh et al.
2005/0137695 A1 6/2005 Salahieh et al.
2005/0182483 A1 8/2005 Osborne et al.
2005/0283231 A1 12/2005 Haug et al.
2006/0004442 A1 1/2006 Spenser et al.
2006/0015083 A1 1/2006 Munro et al.
2006/0020327 A1 1/2006 Lashinski et al.

(56) References Cited

U.S. PATENT DOCUMENTS

| | | | | |
|---|---|---|---|---|
| 2006/0067967 | A1 | 3/2006 | Bowman et al. | |
| 2006/0122689 | A1 | 6/2006 | Kocur et al. | |
| 2006/0161248 | A1 | 7/2006 | Case et al. | |
| 2006/0259136 | A1 | 11/2006 | Nguyen et al. | |
| 2006/0259137 | A1 | 11/2006 | Artof et al. | |
| 2006/0287717 | A1 | 12/2006 | Rowe et al. | |
| 2007/0027531 | A1 | 2/2007 | Dimatteo et al. | |
| 2007/0060998 | A1 | 3/2007 | Butterwick et al. | |
| 2007/0061002 | A1 | 3/2007 | Paul et al. | |
| 2007/0135904 | A1 | 6/2007 | Eidenschink et al. | |
| 2007/0179600 | A1 | 8/2007 | Vardi | |
| 2007/0237956 | A1 | 10/2007 | Figuly et al. | |
| 2007/0239265 | A1 | 10/2007 | Birdsall | |
| 2007/0239269 | A1 | 10/2007 | Dolan et al. | |
| 2007/0244544 | A1 | 10/2007 | Birdsall et al. | |
| 2007/0244546 | A1 | 10/2007 | Francis | |
| 2007/0282436 | A1 | 12/2007 | Pinchuk | |
| 2008/0038325 | A1 | 2/2008 | Nho et al. | |
| 2008/0071361 | A1 | 3/2008 | Tuval et al. | |
| 2008/0071362 | A1 | 3/2008 | Tuval et al. | |
| 2008/0071366 | A1 | 3/2008 | Tuval et al. | |
| 2008/0077234 | A1 | 3/2008 | Styrc et al. | |
| 2008/0082163 | A1 | 4/2008 | Woo | |
| 2008/0125859 | A1 | 5/2008 | Salahieh et al. | |
| 2008/0140189 | A1 | 6/2008 | Nguyen et al. | |
| 2008/0161909 | A1 | 7/2008 | Kheradvar et al. | |
| 2008/0177381 | A1 | 7/2008 | Navia et al. | |
| 2008/0195199 | A1 | 8/2008 | Kheradvar et al. | |
| 2008/0208327 | A1 | 8/2008 | Rowe | |
| 2008/0228263 | A1 | 9/2008 | Ryan | |
| 2008/0234814 | A1 | 9/2008 | Salahieh et al. | |
| 2008/0255660 | A1 | 10/2008 | Guyenot et al. | |
| 2008/0269878 | A1 | 10/2008 | Iobbi | |
| 2008/0275550 | A1 | 11/2008 | Kheradvar et al. | |
| 2009/0099653 | A1 | 4/2009 | Suri et al. | |
| 2010/0036007 | A1 | 2/2010 | Journee | |
| 2010/0131001 | A1 | 5/2010 | Peterson | |
| 2010/0247598 | A1 | 9/2010 | Shetty et al. | |
| 2011/0022157 | A1 | 1/2011 | Essinger et al. | |
| 2011/0098802 | A1* | 4/2011 | Braido | A61F 2/243 623/2.11 |
| 2011/0282426 | A1 | 11/2011 | Mitra et al. | |
| 2012/0041551 | A1 | 2/2012 | Spenser et al. | |
| 2012/0089218 | A1 | 4/2012 | Dardi et al. | |
| 2012/0101571 | A1 | 4/2012 | Thambar et al. | |
| 2012/0123529 | A1 | 5/2012 | Levi et al. | |
| 2012/0271398 | A1* | 10/2012 | Essinger | A61F 2/2412 623/1.11 |
| 2013/0138068 | A1 | 5/2013 | Hu et al. | |
| 2013/0190857 | A1 | 7/2013 | Mitra et al. | |
| 2013/0197622 | A1 | 8/2013 | Mitra et al. | |
| 2013/0204356 | A1 | 8/2013 | Dwork et al. | |
| 2013/0274873 | A1* | 10/2013 | Delaloye | A61F 2/2469 623/2.18 |
| 2013/0331929 | A1 | 12/2013 | Mitra et al. | |
| 2014/0052168 | A1 | 2/2014 | Sawhney | |
| 2014/0194973 | A1 | 7/2014 | Chobotov | |
| 2014/0228453 | A1 | 8/2014 | Bennett et al. | |
| 2014/0277422 | A1* | 9/2014 | Ratz | A61F 2/2418 623/2.37 |
| 2015/0282970 | A1 | 10/2015 | Delaloye | |
| 2016/0030165 | A1 | 2/2016 | Mitra et al. | |
| 2016/0106538 | A1 | 4/2016 | Mitra et al. | |
| 2016/0120646 | A1 | 5/2016 | Dwork et al. | |
| 2016/0158004 | A1 | 6/2016 | Kumar et al. | |
| 2016/0194425 | A1 | 7/2016 | Mitra et al. | |
| 2016/0354201 | A1 | 12/2016 | Keogh | |
| 2016/0361163 | A1* | 12/2016 | Yohanan | A61F 2/2418 |
| 2017/0044344 | A1 | 2/2017 | Gerges et al. | |
| 2019/0046479 | A1 | 2/2019 | Pathak | |
| 2019/0374326 | A1 | 12/2019 | Mitra et al. | |
| 2020/0338154 | A1 | 10/2020 | Garruto et al. | |
| 2022/0112350 | A1 | 4/2022 | Mitra et al. | |

FOREIGN PATENT DOCUMENTS

| | | | | |
|---|---|---|---|---|
| DE | 20003874 | U1 | 5/2000 | |
| DE | 202007005491 | U1 | 6/2007 | |
| EP | 2033593 | A1 | 3/2009 | |
| EP | 2047824 | A1 | 4/2009 | |
| GB | 2476649 | A | 7/2011 | |
| JP | H09500561 | A | 1/1997 | |
| JP | H10507097 | A | 7/1998 | |
| JP | 2004124065 | A | 4/2004 | |
| JP | 2005532120 | A | 10/2005 | |
| NL | 1021328 | C2 | 3/2004 | |
| WO | WO-9602212 | A1 | 2/1996 | |
| WO | WO-9709008 | A1 | 3/1997 | |
| WO | WO-9719653 | A1 | 6/1997 | |
| WO | WO-9851408 | A1 | 11/1998 | |
| WO | WO-0205731 | A1 | 1/2002 | |
| WO | WO-0249535 | A2 * | 6/2002 | A61F 2/06 |
| WO | WO-02098324 | A1 | 12/2002 | |
| WO | WO-03020172 | A1 | 3/2003 | |
| WO | WO-03089506 | A1 | 10/2003 | |
| WO | WO-2004004603 | A1 | 1/2004 | |
| WO | WO-2005070343 | A1 | 8/2005 | |
| WO | WO-2006058163 | A2 | 6/2006 | |
| WO | WO-2006083763 | A1 | 8/2006 | |
| WO | WO-2006127765 | A1 | 11/2006 | |
| WO | WO-2007121072 | A2 | 10/2007 | |
| WO | WO-2007071436 | A3 | 11/2007 | |
| WO | WO-2008023160 | A1 | 2/2008 | |
| WO | WO-2008028569 | A1 | 3/2008 | |
| WO | WO-2008040555 | A2 | 4/2008 | |
| WO | WO-2008042093 | A2 | 4/2008 | |
| WO | WO-2008134493 | A1 | 11/2008 | |
| WO | WO-2009024859 | A2 | 2/2009 | |
| WO | WO-2009053497 | A1 | 4/2009 | |
| WO | WO-2009091509 | A1 | 7/2009 | |
| WO | WO-2010045238 | A2 | 4/2010 | |
| WO | WO-2010045297 | A2 | 4/2010 | |
| WO | WO-2010049160 | A1 | 5/2010 | |
| WO | WO-2010083558 | A1 | 7/2010 | |
| WO | WO-2011027087 | A1 | 3/2011 | |
| WO | WO-2011051043 | A1 | 5/2011 | |
| WO | WO-2011057087 | A1 | 5/2011 | |
| WO | WO-2013033791 | A1 * | 3/2013 | A61F 2/0063 |
| WO | WO-2014145564 | A2 | 9/2014 | |
| WO | WO-2015055652 | A1 | 4/2015 | |
| WO | WO-2016109870 | A1 | 7/2016 | |
| WO | WO-2018170149 | A1 | 9/2018 | |
| WO | WO-2019086958 | A1 | 5/2019 | |
| WO | WO-2020260948 | A1 | 12/2020 | |

OTHER PUBLICATIONS

AU2012307020 Examination Report No. 1 dated May 7, 2014.

AU2014203366 Examination Report No. 1 dated Apr. 27, 2016.

AU2015205978 Examination Report No. 1 dated Mar. 17, 2016.

Baril et al.: Endovascular stent-graft repair of failed endovascular abdominal aortic aneurysm repair, Ann. Vasc. Surg., 22(1):30-6 (2008).

EP10733140.7 European Supplemental Search Report dated Oct. 1, 2015.

EP12829481.6 European Search Report dated Jun. 19, 2015.

EP12829481.6 Office Action dated Jul. 25, 2018.

EP14764576.6 European Supplemental Search Report dated Apr. 13, 2017.

European Patent Application No. 18873278.8 European Search Report dated Jun. 29, 2021.

Ferrari et al.: Transcatheter aortic valve implantation (TAVI): state of the art techniques and future perspectives, Swiss Med Wkly, 140:w13127 (2010).

Grube et al.: Progress and current status of percutaneous aortic valve replacement: results of three device generations of the CoreValve Revalving system, Circ. Cardiovasc, Interv., 1:167- 175 (2008).

Himbert et al.: Results of transfemoral or transapical aortic valve implantation following a uniform assessment in high-risk patients with aortic stenosis, J. Am. Coll. Cardiol., 54:303-311 (2009).

(56) References Cited

OTHER PUBLICATIONS

Indian Patent Application No. 1366/DELNP/2014 First Examination Report dated Jul. 26, 2019.
Indian Patent Application No. IN6395/DELNP/2011 Office Action dated Sep. 14, 2017.
Jackson et al.: Devices used for endovascular aneurysm repair: past, present, and future, Seminars in Interventional Radiology, 26:39-43 (2009).
Kim et al.: Swelling and mechanical properties of superporous. hydrogels of poly(acrylamide-co-acrylic acid)/polyethylenimine interpenetrating polymer networks, Polymer 45, 189-196 (2004).
Leon et al.: Standardized endpoint definitions for transcatheter aortic valve implantation clinical trials, J Am Coll Cardiol., 57:253-69 (2011).
Leon et al.: Transcatheter aortic-valve implantation for aortic stenosis in patients who cannot undergo surgery, N. Engi. J. Med., 363:1597-1607 (2010).
Ma et al.: Development of cationic polymer coatings to regulate foreign-body responses, Adv. Mater., 23:H189-94 (2011).
Patel et al.: Endovascular aortic aneurysm repair with chimney and snorkel grafts: indications, techniques and results, Cardiovascular and Interventional Radiology, 36 (6): 1443-1451 (2013).
Pawelec-Wojtalik et al.: Closure of left ventricle perforation with the use of muscular VSD occlude, European J Cardio-Thoracic Surg, 27:714-716 (2005).
PCT/AU2010/000050 International Search Report dated May 25, 2010.
PCT/AU2010/000050 International Preliminary Report on Patentability dated Jul. 26, 2011.
PCT/AU2012/001080 International Preliminary Report on Patentability dated Mar. 12, 2014.
PCT/AU2012/001080 International Search Report dated Mar. 14, 2013.
PCT/AU2016/050003 International Search Report dated Mar. 18, 2016.
PCT/AU2016/050003 International Preliminary Report on Patentability dated May 9, 2017.
PCT/IB2018/001400 Invitation to Pay Additional Fees dated Jan. 16, 2019.
PCT/IB2018/001400 International Search Report and Written Opinion dated Mar. 22, 2019.
PCT/IB2018/001400 International Preliminary Report on Patentability dated May 5, 2020.
PCT/IB2020/000540 International Search Report and Written Opinion dated Nov. 6, 2020.
PCT/US2014/030355 International Search Report dated Oct. 17, 2014.
PCT/US2014/030355 International Preliminary Report on Patentability dated Sep. 15, 2015.
Qiu et al.: Superporous IPN hydrogels having enhanced mechanical properties, AAPS Pharm Sci Tech., 40(4):406-412 (2003).
Rodes-Cabau et al.: Transcatheter aortic valve implantation for the treatment of severe symptomatic aortic stenosis in patients at very high or prohibitive surgical risk: acute and late outcomes of the multicenter Canadian experience', J. Am. Coll. Cardiol., 55:1080-90 (2010).
Shazly et al.: Augmentation of postswelling surgical sealant potential of adhesive hydrogels, J. Biomed. Mat. Res., Pt. A, 95A(4): 1159-1169 (2010).
Singh et al.: What Is Your Preferred EVAR Device and Why, Endovasular Today, February:63- 66 (2013).
U.S. Appl. No. 13/145,957 Office Action dated Jun. 28, 2017.
U.S. Appl. No. 13/596,894 Final Office Action dated Jan. 2, 2019.
U.S. Appl. No. 13/844,535 Office Action dated Feb. 17, 2017.
U.S. Appl. No. 13/844,535 Office Action dated May 31, 2016.
U.S. Appl. No. 13/844,535 Office Action dated Sep. 17, 2015.
U.S. Appl. No. 14/976,917 Final Office Action dated Nov. 30, 2018.
U.S. Appl. No. 13/145,957Office Action dated Apr. 11, 2014.
U.S. Appl. No. 13/145,957 Office Action dated Jan. 6, 2015.
U.S. Appl. No. 13/145,957 Office Action dated Jul. 11, 2016.
U.S. Appl. No. 13/145,957 Office Action dated Mar. 23, 2016.
U.S. Appl. No. 13/145,957 Office Action dated Sep. 15, 2015.
U.S. Appl. No. 13/476,695 Office Action dated Jul. 8, 2015.
U.S. Appl. No. 13/476,695 Office Action dated Sep. 12, 2014.
U.S. Appl. No. 16/759,986 Restriction Requirement dated Nov. 29, 2021.
Webb et al.: Transcatheter aortic valve implantation: impact on clinical and valve-related outcomes, Circulation, 119:3009-16 (2009).
EP20833122-3 European Search Report dated Jan. 18, 2024.
U.S. Appl. No. 16/457,608 Final Office Action dated Sep. 26, 2023.
U.S. Appl. No. 16/457,608 Office Action dated Feb. 3, 2023.
U.S. Appl. No. 16/457,608 Restriction Requirement dated Aug. 11, 2022.
U.S. Appl. No. 16/457,608 Office Action dated Apr. 25, 2024.
U.S. Appl. No. 17/559,956 Office Action dated Aug. 13, 2024.

* cited by examiner

Fig. 1B
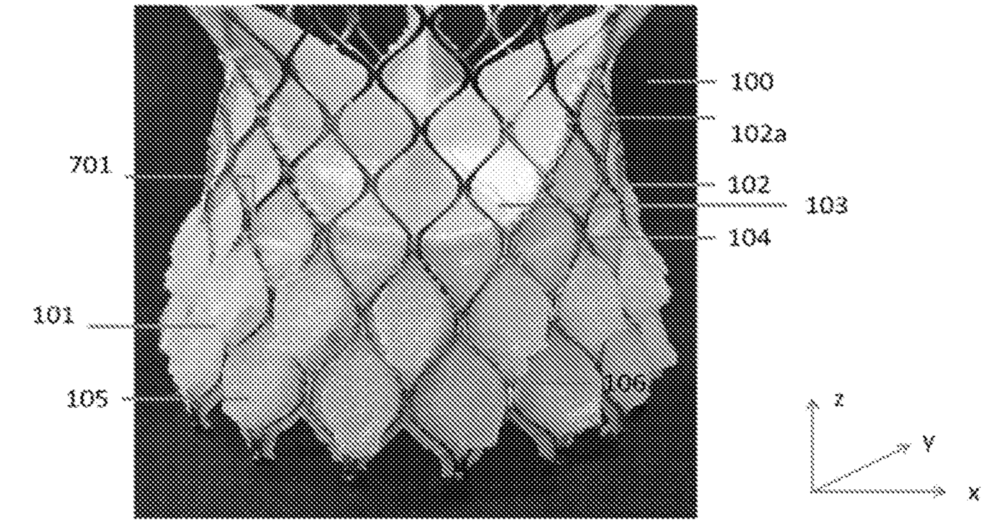
Fig. 1C
Fig. 1D
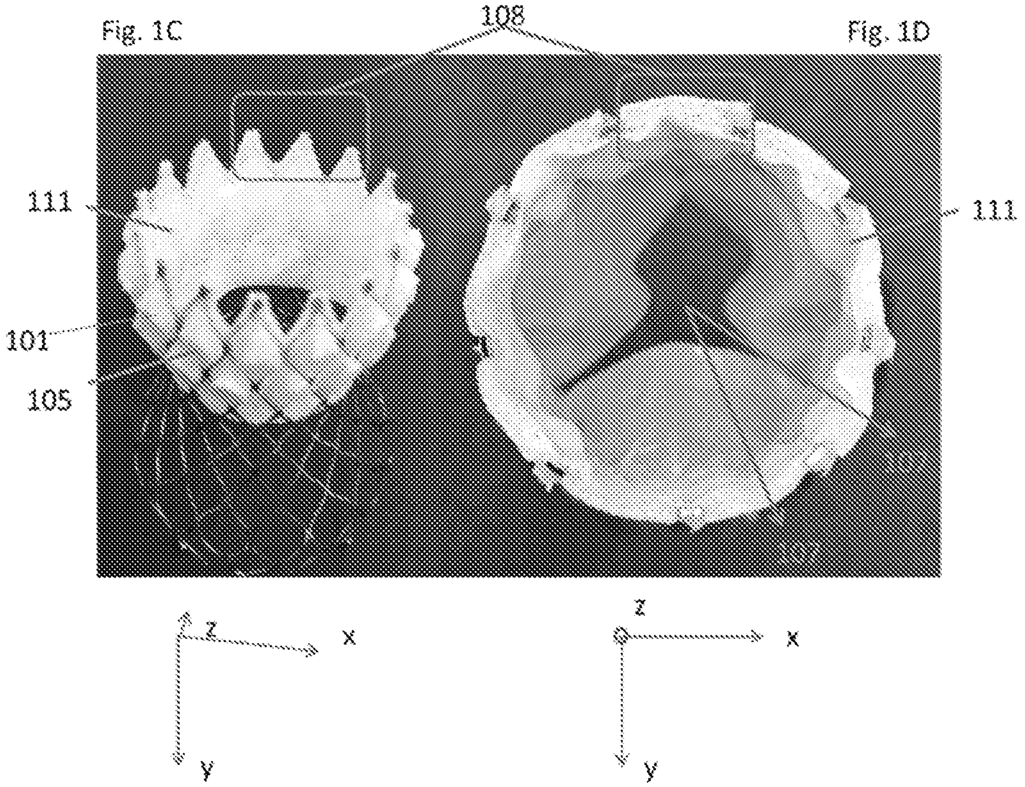

A
A'
110
120
130
100
102a
102
104
101a
101
105
101b
z
y
x

Loading direction
Longitudinal direction
114
102
B
114
Radial direction 801b
801a
801c
814
801
811
812
a
h
a 102
102a 110
120
130

102b
110
130

110
130

110
130
102b
102
102a
110
130
24.535
0.330
0.730
51.236
R1
R0.800
2
R0.400
2.900
13
0.330
110
120
130
2.900
R1
2
R0.400
131a
131b
130a
1.320
0.330

102a
102
102b
110
120
130
19.60
26
102f
102g
102e
102a
102d
102f
81.67
37.32
0.40
9.24
4.10
19.60
0.43

111

X
112
C

G
105
H
C
W
114

Y
SECTION C-C
SCALE 2 : 1

101b

Fig. 4E
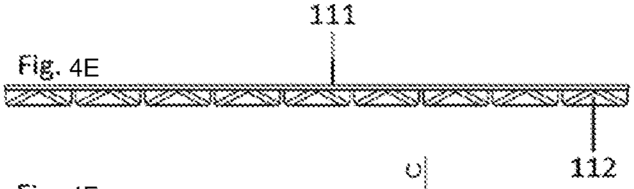
Fig. 4F
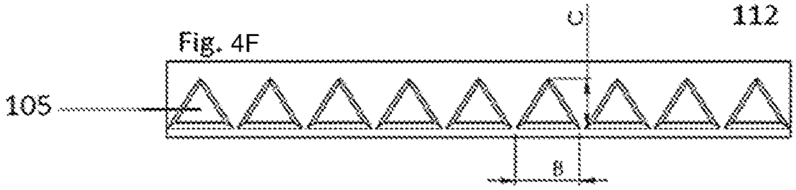
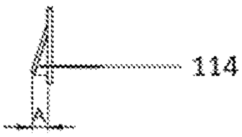
Fig. 4H
Fig. 4G
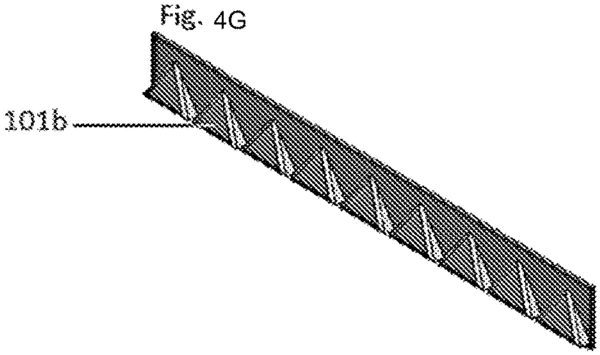

FIG. 4I
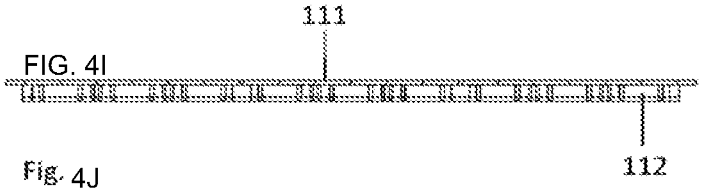
Fig. 4J
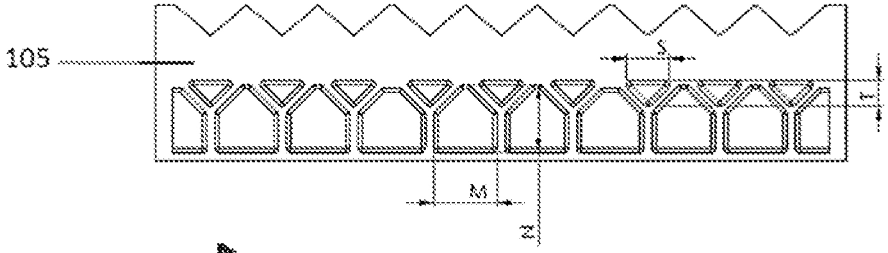
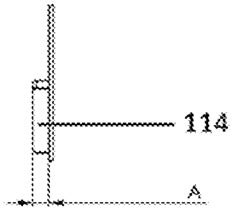
Fig. 4L
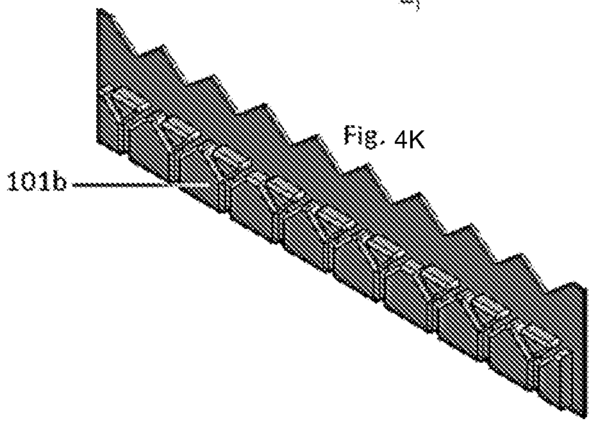
Fig. 4K

Fig. 4M
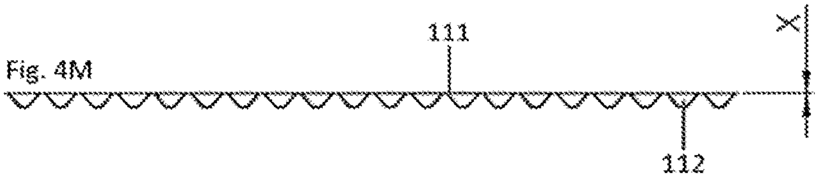
Fig. 4N
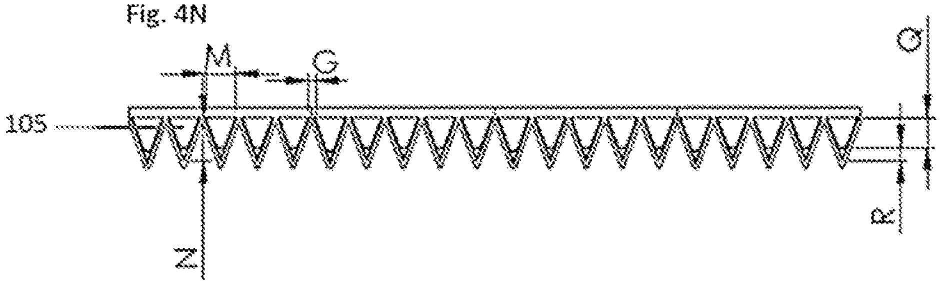
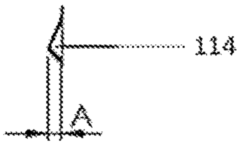
Fig. 4P
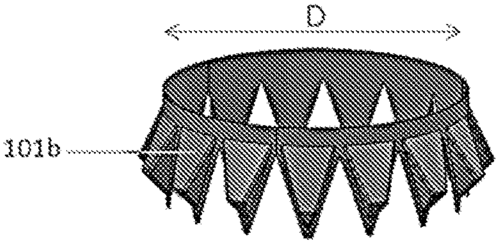
Fig. 4O 111
112
X

105
G
Y
W

101b

114
B
C
A

Fig. 5E
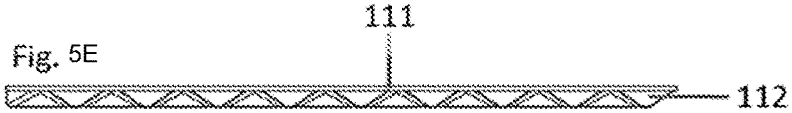
Fig. 5F
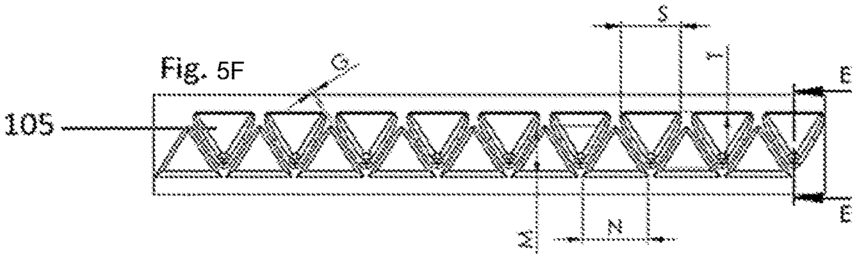
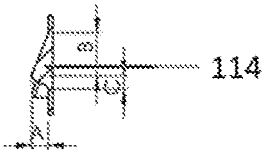
Fig. 5H
SECTION E-E
SCALE 2 : 1
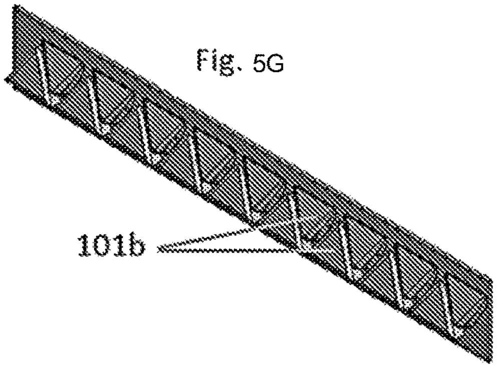
Fig. 5G
Fig. 5I
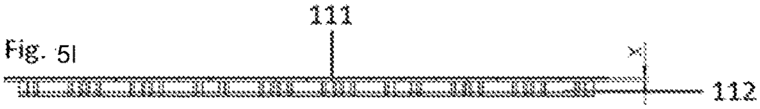
Fig. 5J
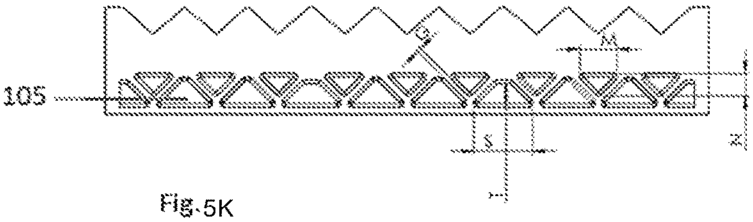
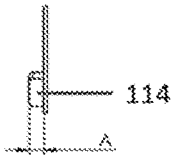
Fig. 5L
Fig. 5K
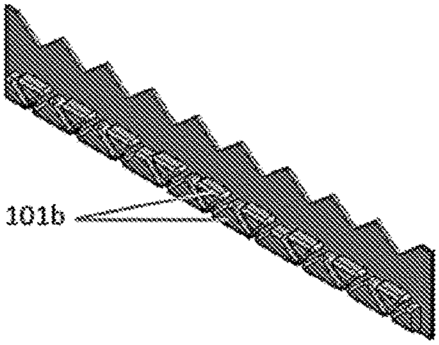

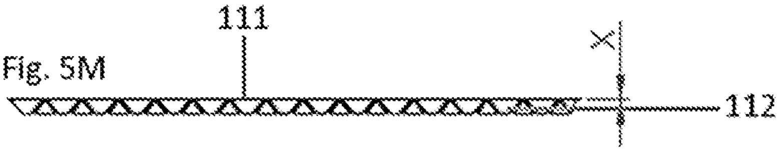
Fig. 5M
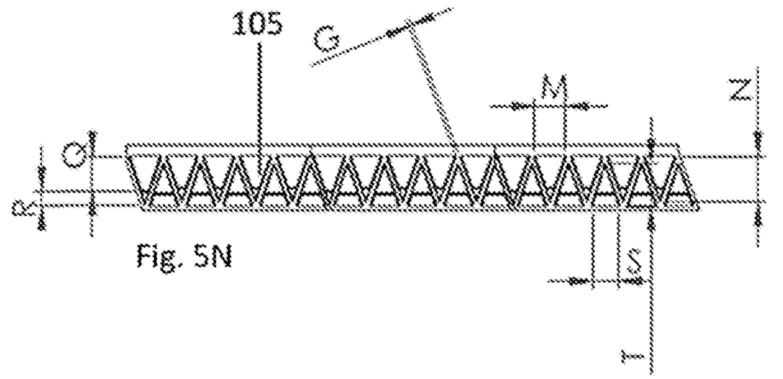
Fig. 5N
Fig. 5P
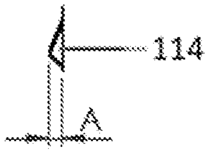
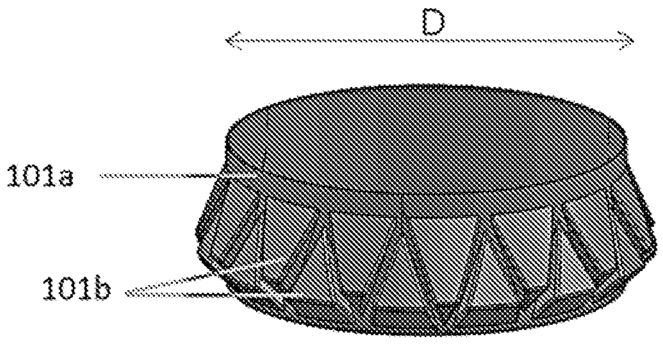
Fig. 5O

111

112
105
101d 114
101d 101b
101a
105
101b
101c

101d 101b
101a
105
d2
d4
d6
dn+1
d1
d3
d5
dn
105

101b
101a
105
d2
d4
d6
dn+1
d1
d3
d5
dn
105

101b
101a
105
d2
d4
d6
dn+1
d1
d3
d5
dn
101c 101a
101b
105
d1
d3
d5
dn
d2
d4
d6
dn+1
101c 0.30
6.79
6.26
E
E
5.72
7.43

4.75
1.50
1.87
SECTION E-E
SCALE 2 : 1

EXPANDABLE SEALING SKIRT TECHNOLOGY FOR LEAK-PROOF ENDOVASCULAR PROSTHESES

CROSS-REFERENCE

This application claims priority to U.S. Provisional Patent Application No. 62/579,005, filed on Oct. 30, 2017, U.S. Provisional Patent Application No. 62/674,510, filed on May 21, 2018, U.S. Provisional Patent Application No. 62/674,515, filed on May 21, 2018, U.S. Provisional Patent Application No. 62/674,517, filed on May 21, 2018, U.S. Provisional Patent Application No. 62/674,519, filed on May 21, 2018, and U.S. Provisional Patent Application No. 62/674,522, filed on May 21, 2018, each of which is entirely incorporated herein by reference.

BACKGROUND OF THE INVENTION

Over the last decade, a significant number of patients with valvular heart diseases, such as aortic stenosis and mitral and tricuspid incompetence, are not offered definitive therapy because they are deemed high-risk for open surgical valve replacement. The development of percutaneous heart valve technologies, such as transcatheter aortic valve implantation (TAVI) or transcatheter mitral valve repair (TMVR) can transform cardiovascular medicine by providing a minimally invasive approach for heart valve replacement in inoperable and high-risk patients. TAVI and TMVR can provide a treatment alternative that is associated with significantly lower procedural morbidity/mortality, shorter hospitalization and more rapid recovery.

SUMMARY OF THE INVENTION

The development of percutaneous heart valve technologies, such as transcatheter aortic valve implantation (TAVI) or transcatheter mitral valve repair (TMVR) can transform cardiovascular medicine by providing a minimally invasive approach for heart valve replacement in inoperable and high-risk patients. However, the critical limitation is that the devices are associated with unacceptably high rates of leakage of blood around the transcatheter valve (e.g., paravalvular regurgitation), a problem that is rare in conventional surgical valve replacement. The problem of paravalvular regurgitation remains a key barrier in preventing the extension of the potential benefits of TAVI and/or TMVR to the two thirds of patients that are currently offered conventional open heart surgery. Significant paravalvular regurgitation can be associated with increased mortality and represents the most significant unresolved problem of TAVI and TMVR. The present disclosure which includes a leak-proof transcatheter valve can advantageously eliminate or minimize paravalvular leak thereby transforming TAVI and/or TMVR by improving outcomes for inoperable and high-risk patients, and facilitating the expansion of TAVI and/or TMVR into current surgical patients.

Provided herein is a device assembly for endovascular prosthesis implantation in a human patient, the device assembly comprising a collapsed delivery configuration and an expanded deployed configuration and comprising when in the expanded deployed configuration: a stent frame comprising a generally conical section, a flared section, and a constriction region between the conical section and the flared section, and a first layer and a second layer of expandable stent cells in the generally conical section, the layers stacked in a longitudinal direction, wherein each of the plurality of expandable stent cells of the first and second layers comprise a cell pattern defined by a first zig-zag extending in the longitudinal direction comprising a first leg and a second leg coupled thereto by a first inflection, and a second zig-zag extending in the longitudinal direction comprising a third leg coupled to a fourth leg by a second inflection, wherein the first leg is coupled to the third leg at a third inflection, and the second leg is coupled to the fourth leg at a fourth inflection, forming thereby a substantially diamond shape, wherein the first leg and the second leg are unequal in length; a valve attached to the stent frame; and an expandable sealing skirt coupled to the stent frame at the generally conical section, the expandable sealing skirt comprising a non-protruding region and a protruding region extending radially beyond the expandable stent cells in the generally conical section of the stent frame. In some embodiments, a protruding thickness of the protruding region along the radial direction is spatially variable at least along a longitudinal direction. In some embodiments, the protruding region comprises protruding cells and connecting regions connecting the protruding cells, wherein the protruding cells expand radially beyond the expandable stent cells. In some embodiments, the protruding cells comprise a pattern reflecting the cell pattern of the stent frame in the conical section, or wherein the protruding cells comprise a pattern reflecting a portion of the cell pattern of the stent frame in the conical section, or wherein one or more of the protruding cells comprise a pattern reflecting the cell pattern of the stent frame in the conical section and one or more of the protruding cells comprise a second pattern reflecting a portion of the cell pattern of the stent frame in the conical section. In some embodiments, the protruding cells extend through one or more of the expandable stent cells in the first layer and the second layer. In some embodiments, the connecting regions are coincident with one or more of the first leg through the fourth leg, or are coincident with at least one or more of the first through the fourth inflections, or a combination thereof. In some embodiments, the connecting regions are coincident with a portion of one or more of the first leg through the fourth leg, or are coincident with a portion of at least one or more of the first through the fourth inflections, or a portion or a combination thereof. In some embodiments, the device assembly is in the expanded deployed configuration, one or more of the protruding cells comprises a cross section along a radial direction that is substantially a rectangle, or a triangle. In some embodiments, the device assembly is in the expanded deployed configuration, one or more of the protruding cells comprises a cross section along a radial direction that protrudes less through the expandable stent cell at its proximal end than it protrudes through the expandable stent cell at its distal end. In some embodiments, the protruding region forms a protruding ring. In some embodiments, the protruding ring when viewed longitudinally from the proximal to distal end of the protruding region, has protruding cells around the entire circumference of the protruding region. In some embodiments, the protruding cells, the connecting region, or both, comprises foam. In some embodiments, the foam has an open pore structure, a closed pore structure, or a combination. In some embodiments, the foam has a controlled porosity. In some embodiments, the foam has a uniform porosity. In some embodiments, the foam has a variable porosity. In some embodiments, the foam has a porosity of about 5-500 micrometers. In some embodiments, the more than one layer comprises five layers. In some embodiments, stent cells in a first layer are no smaller than the stent cells in a second layer that is more distal to the first layer when the stent frame is in the expanded deployed configuration. In some embodiments, stent cells from a first layer comprise a shape that is substantially identical to a second shape of the stent cells from a second layer when the stent frame is in the expanded deployed configuration. In some embodiments, the stent frame comprises up to thirty total zig-zags inclusive of the first and second zig-zags, each zig-zag extending in the longitudinal direction, and each zig-zag coupled to adjacent zig-zags at inflections to form a device assembly in a tube shape wherein each of the two layers each comprises closed diamond shaped cells. In some embodiments, when the stent frame is in the expanded deployed configuration and laid flat, the plurality of stent cells comprises one or more a diamond shape. In some embodiments, the stent frame comprises a proximal or top portion, and a bottom or distal portion, wherein at least part of the generally conical section is in the bottom portion. In some embodiments, at least part of the flared section is in the top portion. In some embodiments, the stent frame comprises a cross section that is substantially circular at the top portion, the bottom portion, or both when the stent frame is in the expanded deployed configuration. In some embodiments, each stent cell of the one or more layers of stent cells comprises a height along the longitudinal direction of about 6 mm to about 12 mm when the stent frame is in the expanded deployed configuration. In some embodiments, the stent frame comprises a maximum height along the longitudinal direction in the range of 30 mm to 45 mm when the stent frame is in the expanded deployed configuration. In some embodiments, the stent frame comprises a diameter (outer diameter) of a cross section perpendicular to the longitudinal direction in the range of 15 mm to 40 mm when the stent frame is in the expanded deployed configuration as measured from outer wall of the stent frame optionally at a distal end of the stent frame. In some embodiments, the stent frame comprises a thickness of about 0.2 mm to about 1 mm along a radial direction. In some embodiments, the stent frame comprises a layer of open ends proximal to a most proximal layer of stent cells. In some embodiments, the stent frame comprises a layer of open ends distal to a most distal layer of stent cells. In some embodiments, one or more inflections of one or more stent cells of the plurality of stent cells comprise two stent struts directly attached together or integrally formed together. In some embodiments, the two stent struts remain attached when the stent frame is in the expanded deployed configuration or the collapsed delivery configuration. In some embodiments, the device assembly is configured to be delivered within a delivery catheter. In some embodiments, the expandable sealing skirt is self-expandable when the device assembly is deployed. In some embodiments, the expandable sealing skirt is configured to self-expand against the vessel wall instantaneously, in about 0.001 second to about 1 minute after it is out of the delivery catheter. In some embodiments, the expandable sealing skirt comprises from a 2× to a 30×, a 3× to a 20×, a 5× to a 30×, a 10× to a 30×, a 2× to a 20×, at least 2×, at least 5×, at least 10×, 1.5× to 20×, 1.5× to 30×, at most 20×, at most 10×, or at most a 30× volumetric expansion from an collapsed state to an expanded state. In some embodiments, the protruding cells comprise from a 2× to a 30×, a 3× to a 20×, a 5× to a 30×, a 10× to a 30×, a 2× to a 20×, at least 2×, at least 5×, at least 10×, 1.5× to 20×, 1.5× to 30×, at most 20×, at most 10×, or at most a 30× volumetric expansion from an collapsed state to an expanded state. In some embodiments, the device assembly comprises sutures coupling the expandable sealing skirt to the stent frame. In some embodiments, the expandable sealing skirt is coupled by the sutures to the stent frame at one or more proximally-facing edges of protruding cells. In some embodiments, the expandable sealing skirt is coupled by the sutures to the stent frame at the intersection of the non-protruding region and the protruding region along a proximal edge of the protruding cells. In some embodiments, the expandable sealing skirt is coupled by the sutures to the stent frame at the distal legs of the most distal layer of the first layer and second layer of the stent frame. In some embodiments, the expandable sealing skirt is coupled by the sutures to the stent frame at one or more proximal facing legs of the most proximal layer of the first layer and second layer of the stent frame. In some embodiments, the expandable sealing skirt is coupled by the sutures to the stent frame at one or more distal facing legs of the most distal layer of the first layer and second layer of the stent frame. In some embodiments, the expandable skirt is biocompatible and biostable when the device assembly is implanted in the human patient. In some embodiments, the expandable skirt is attached to a top, middle, or bottom portion of the stent frame. In some embodiments, the expandable skirt is compressible instantaneously within a time period of about 0.001 second to about 1 minute. In some embodiments, the device assembly comprises a pericardial tissue skirt attached to the stent frame or a PET or Dacron skirt. In some embodiments, the non-protruding region is permanently integrated with the protruding region. In some embodiments, the non-protruding region is at least partly located within the stent frame when coupled to the stent frame. In some embodiments, a maximum protruding thickness of the protruding region along the radial direction is in the range of about 3 mm to about 1 cm, or 3 mm to 1 cm.

Provided herein is a method of endovascular prosthesis implantation with an expandable skirt in a human patient using the device assembly herein, the method comprising: delivering the device assembly within a delivery catheter in the collapsed delivery configuration to a preselected location within the human patient, deploying the device assembly by: relative movement of the delivery catheter with respect to the device assembly thereby allowing the stent frame and the expandable skirt to self-expand or expand in a controlled manner against a vessel wall. In some embodiments, the method comprises recapturing the device assembly within the delivery catheter by relative movement of the delivery catheter with respect to the device assembly thereby allowing the expandable skirt to compress within the delivery catheter. In some embodiments, the method comprises retrieving the delivery catheter from the patient, the delivery catheter enclosing the device assembly therewithin in a resheathed state. In some embodiments, the method comprises controlled expansion is via controlling a balloon catheter that the expandable skirt is loaded thereon.

Provided herein is a device assembly for endovascular prosthesis implantation in a human patient, the device assembly comprising a collapsed delivery configuration and an expanded deployed configuration, and the device assembly comprising: a stent frame comprising a plurality of expandable stent cells arranged in more than one layer and stacked in a longitudinal direction, wherein in the expanded deployed configuration the stent frame comprises a substantially columnar section and a flared section, wherein two or more layers of stent cells are of a substantially diamond shape, and wherein the stent frame comprises non-expandable connectors positioned between the substantially conical section or the substantially columnar section and the flared section; a valve attached to the stent frame; and an expandable sealing skirt coupled to the stent frame at the substantially columnar section, the expandable sealing skirt comprising a protruding region configured to expand radially past the more than one layers of stent cells of the stent frame when the device assembly is in the expanded deployed configuration and a non-protruding region. In some embodiments, a protruding thickness of the protruding region along the radial direction is spatially variable at least along a longitudinal direction. In some embodiments, the protruding region comprises protruding cells and connecting regions connecting the protruding cells, wherein the protruding cells expand radially beyond the expandable stent cells. In some embodiments, the protruding cells comprise a pattern reflecting the cell pattern of the stent frame in the columnar section, or wherein the protruding cells comprise a pattern reflecting a portion of the cell pattern of the stent frame in the columnar section, or wherein one or more of the protruding cells comprise a pattern reflecting the cell pattern of the stent frame in the columnar section and one or more of the protruding cells comprise a second pattern reflecting a portion of the cell pattern of the stent frame in the columnar section. In some embodiments, the protruding cells extend through one or more of the expandable stent cells in the first layer and the second layer. In some embodiments, the connecting regions are coincident with one or more of a first leg through a fourth leg of the diamond shape of the stent cell, or are coincident with at least one or more of a first through fourth inflection of the diamond shape of the stent cell, or a combination thereof. In some embodiments, the connecting regions are coincident with a portion of one or more of a first leg through a fourth leg of the diamond shape of the stent cell, or are coincident with a portion of at least one or more of a first through a fourth inflections of the diamond shape of the stent cell, or a portion or a combination thereof. In some embodiments, when the device assembly is in the expanded deployed configuration, one or more of the protruding cells comprises a cross section along a radial direction that is substantially a rectangle, or a triangle. In some embodiments, when the device assembly is in the expanded deployed configuration, one or more of the protruding cells comprises a cross section along a radial direction that protrudes less through the expandable stent cell at its proximal end than it protrudes through the expandable stent cell at its distal end. In some embodiments, the protruding region forms a protruding ring. In some embodiments, the protruding ring when viewed longitudinally from the proximal to distal end of the protruding region, has protruding cells around the entire circumference of the protruding region. In some embodiments, the expandable skirt comprises foam. In some embodiments, the foam has an open pore structure, a closed pore structure, or a combination. In some embodiments, the foam has a controlled porosity. In some embodiments, the foam has a uniform porosity. In some embodiments, the foam has a variable porosity. In some embodiments, the foam has a porosity of about 5-500 micrometers. In some embodiments, the more than one layer comprises four or five layers. In some embodiments, stent cells in a first layer of the substantially columnar section is smaller than the stent cells in a second layer that is more distal to the first layer when the stent frame is in the expanded deployed configuration. In some embodiments, stent cells in a first layer comprise a shape that is substantially identical to a second shape of the stent cells from a second layer when the stent frame is in the expanded deployed configuration. In some embodiments, when the stent frame is in the expanded deployed configuration the plurality of stent cells comprises one or more shapes of: a diamond shape and a rhomboid shape. In some embodiments, stent cells from a most proximal layer comprise a substantially diamond shape when the stent frame is in the expanded deployed configuration. In some embodiments, stent cells from a most distal layer comprise a substantially diamond shape when the stent frame is in the expanded deployed configuration. In some embodiments, each stent cell comprises a substantially identical shape when the stent frame is in the expanded deployed configuration. In some embodiments, each stent cell comprises a substantially diamond shape when the stent frame is in the expanded deployed configuration. In some embodiments, the stent frame comprises a top portion, a bottom portion, and optionally a middle portion. In some embodiments, at least part of the substantially columnar section is in the bottom portion. In some embodiments, at least part of the flared section is in the top portion. In some embodiments, the top portion is more proximal than the bottom portion, and directly attached to the bottom portion. In some embodiments, the top portion and the bottom portion are connected by the connectors. In some embodiments, the connectors comprise one or more straight struts and one or more loops. In some embodiments, a height of the connectors is smaller than the height of the stent cells. In some embodiments, each of the connectors connects two stent cells, and wherein the two stent cells do not share any vertices. In some embodiments, the stent frame comprises a cross section that is substantially circular at the top portion, the bottom portion, or both when the stent frame is in the expanded deployed configuration. In some embodiments, each stent cell of the one or more layers of stent cells comprises a height along the longitudinal direction of about 8 mm to about 15 mm, when the stent frame is in the expanded deployed configuration. In some embodiments, each stent cell of the one or more layers of stent cells comprises a height along the longitudinal direction of about 20 mm to about 40 mm, when the stent frame is in the expanded deployed configuration. In some embodiments, the stent frame comprises a height along the longitudinal direction in the range of 40 mm to 60 mm, when the stent frame is in the expanded deployed configuration. In some embodiments, the stent frame comprises a diameter (outer diameter) of a cross section perpendicular to the longitudinal direction in the range of 15 mm to 40 mm when the stent frame is in the expanded deployed configuration as measured from outer wall of the stent frame optionally at a distal end of the stent frame. In some embodiments, the stent frame comprises a thickness of about 0.2 mm to about 1 mm along a radial direction. In some embodiments, he stent frame comprises a layer of open ends proximal to a most proximal layer of stent cells. In some embodiments, the stent frame comprises a layer of open ends distal to a most distal layer of stent cells. In some embodiments, one or more inflections of one or more stent cells of the plurality of stent cells comprise two stent struts directly attached together or integrally formed together. In some embodiments, the protruding region comprises a protruding ring. In some embodiments, the device assembly is configured to be delivered within a delivery catheter. In some embodiments, the device assembly is deployed via relative movement out of the delivery catheter. In some embodiments, the expandable sealing skirt is self-expandable when the device assembly is deployed. In some embodiments, the expandable skirt is configured to self-expand against the vessel wall instantaneously, in about 0.001 second to about 1 minute after it is out of the delivery catheter. In some embodiments, the expandable sealing skirt comprises from a 2× to a 30×, a 3× to a 20×, a 5× to a 30×, a 10× to a 30×, a 2× to a 20×, at least 2×, at least 5×, at least 10×, 1.5× to 20×, 1.5× to 30×, at most 20×, at most 10×, or at most a 30× volumetric expansion from an collapsed state to an expanded state. In some embodiments, the protruding cells comprise from a 2× to a 30×, a 3× to a 20×, a 5× to a 30×, a 10× to a 30×, a 2× to a 20×, at least 2×, at least 5×, at least 10×, 1.5× to 20×, 1.5× to 30×, at most 20×, at most 10×, or at most a 30× volumetric expansion from an collapsed state to an expanded state. In some embodiments, the expandable skirt is attached to one or more of the stent frame, the valve, and a pericardial tissue skirt using sutures. In some embodiments, the expandable skirt is attached to the stent frame at one or more edges of protruding cells of the protruding region. In some embodiments, the device assembly comprises sutures coupling the expandable sealing skirt to the stent frame. In some embodiments, the expandable sealing skirt is coupled by the sutures to the stent frame at one or more proximally-facing edges of protruding cells. In some embodiments, the expandable sealing skirt is coupled by the sutures to the stent frame at the intersection of the non-protruding region and the protruding region along a proximal edge of the protruding cells. In some embodiments, the expandable sealing skirt is coupled by the sutures to the stent frame at the distal legs of the most distal layer of the first layer and second layer of the stent frame. In some embodiments, the expandable sealing skirt is coupled by the sutures to the stent frame at one or more proximal facing legs of the most proximal layer of the first layer and second layer of the stent frame. In some embodiments, the expandable sealing skirt is coupled by the sutures to the stent frame at one or more distal facing legs of the most distal layer of the first layer and second layer of the stent frame. In some embodiments, the expandable skirt is biocompatible and biostable when the device assembly is implanted in the human patient. In some embodiments, the expandable skirt is attached to a top, middle, or bottom portion of the stent frame. In some embodiments, the expandable skirt is compressible instantaneously within a time period of about 0.001 second to about 1 minute. In some embodiments, the device assembly comprises a pericardial tissue skirt attached to the stent frame or a PET or Dacron skirt. In some embodiments, the non-protruding region is permanently integrated with the protruding region. In some embodiments, the non-protruding region is at least partly located within the stent frame when properly attached to the stent frame.

Provided herein is a method of endovascular prosthesis implantation with an expandable skirt in a human patient using the device assembly herein, the method comprising: delivering the device assembly within a delivery catheter in the collapsed delivery configuration to a preselected location within the human patient, deploying the device assembly by: relative movement of the delivery catheter with respect to the device assembly thereby allowing the stent frame and the expandable skirt to self-expand or expand in a controlled manner against a vessel wall. In some embodiments, the method comprises recapturing the device assembly within the delivery catheter by relative movement of the delivery catheter with respect to the device assembly thereby allowing the expandable skirt to compress within the delivery catheter. In some embodiments, the method comprises retrieving the delivery catheter from the patient, the delivery catheter enclosing the device assembly therewithin in a resheathed state. In some embodiments, the controlled expansion is via controlling a balloon catheter that the expandable skirt is loaded thereon.

Provided herein is a device assembly for endovascular prosthesis implantation in a human patient, the device assembly comprising a collapsed delivery configuration and an expanded deployed configuration, and the device assembly comprising when in the expanded deployed configuration: a stent frame being tubular and having a circular cross section comprising a plurality of longitudinally rigid support beams of fixed length, and a first layer and a second layer of expandable stent cells, the layers stacked in a longitudinal direction, wherein the second layer is distal to the first layer and is a distalmost layer of stent cells in the stent frame, wherein each of the plurality of expandable stent cells of the first layer comprises a first shape that is a substantially hexagon shape, and wherein each of the plurality of expandable stent cells of the second layer comprises a second shape that is a substantially diamond shape; a valve attached to the plurality of support beams; and an expandable sealing skirt coupled to the stent frame, the expandable sealing skirt comprising a non-protruding region and a protruding region extending radially the expandable stent cells of the stent frame. In some embodiments, the stent frame comprises extending legs extending distally from the second layer. In some embodiments, the protruding region is positioned distal and adjacent to the second layer and between and adjacent to the extending legs. In some embodiments, a protruding thickness of the protruding region along the radial direction is spatially consistent at least along a longitudinal direction. In some embodiments, the protruding region comprises protruding cells and connecting regions connecting the protruding cells, wherein the protruding cells expand radially beyond the expandable stent cells. In some embodiments, the protruding cells comprise a pattern reflecting a cell pattern of the stent frame, or wherein the protruding cells comprise the pattern reflecting a portion of the cell pattern of the stent frame, or wherein one or more of the protruding cells comprise the pattern reflecting the cell pattern of the stent frame and one or more of the protruding cells comprise a second pattern reflecting a portion of the cell pattern of the stent frame. In some embodiments, the protruding cells extend through one or more of the expandable stent cells in the first layer and the second layer. In some embodiments, the connecting regions are coincident with one or more legs of stent cells, or are coincident with at least one or more inflections, or a combination thereof. In some embodiments, the connecting regions are coincident with a portion of one or more legs, or are coincident with a portion of at least one or more inflections, or a combination thereof. In some embodiments, when the device assembly is in the expanded deployed configuration, one or more of the protruding cells comprises a cross section along a radial direction that is substantially a rectangle. In some embodiments, the protruding region forms a protruding ring. In some embodiments, the protruding ring when viewed longitudinally from the proximal to distal end of the protruding region, has protruding cells around an entire circumference of the protruding region. In some embodiments, the protruding cells, the connecting region, or both, comprises foam. In some embodiments, the foam has an open pore structure, a closed pore structure, or a combination. In some embodiments, the foam has a controlled porosity. In some embodiments, the foam has a uniform porosity. In some embodiments, the foam has a variable porosity. In some embodiments, the foam has a porosity of about 5-500 μm. In some embodiments, the plurality of support beams are provided with bores for allowing suturing or tying the valve or the expandable sealing skirt thereto. In some embodiments, the stent frame comprises a third layer and a fourth layer. In some embodiments, stent cells in a first layer that is more proximal are smaller than the stent cells in a second layer. In some embodiments, stent cells from a most proximal layer comprises a substantially diamond shape. In some embodiments, stent cells from a most proximal layer comprises a substantially hexagon shape. In some embodiments, stent cells from a most distal layer comprises a substantially diamond shape. In some embodiments, stent cells from a most distal layer comprises a substantially hexagon shape. In some embodiments, the stent frame comprises a top or proximal portion, and a bottom or distal portion. In some embodiments, the top portion is more proximal than the bottom portion In some embodiments, the stent frame comprises a cross section that is substantially circular at the top portion, the bottom portion, or both when the stent frame is in the expanded deployed. In some embodiments, each stent cell of the one or more layers of stent cells comprises a height along the longitudinal direction of about 3 mm to about 10 mm. In some embodiments, the stent frame comprises a maximum height along the longitudinal direction in the range of 18 mm to 25 mm. In some embodiments, the stent frame comprises a diameter of a cross section in the range of 20 mm to 40 mm when the stent frame is in the expanded deployed configuration as measured from an outer wall of the stent frame optionally at a distal end of the stent frame. In some embodiments, the stent frame comprises a thickness of about 0.2 mm to about 1 mm along a radial direction. In some embodiments, the stent frame comprises a layer of open ends proximal to a most proximal layer of stent cells. In some embodiments, the stent frame comprises a layer of open ends distal to a most distal layer of stent cells. In some embodiments, one or more open ends of the layer forms at least part of a substantially triangular shape. In some embodiments, one or more open ends of the layer forms a substantially pentagon shape. In some embodiments, one or more inflections of one or more stent cells of the plurality of stent cells comprise two stent struts directly attached together or integrally formed together. In some embodiments, the two stent struts remain attached when the stent frame is in the expanded deployed configuration or the collapsed delivery configuration. In some embodiments, the device assembly is configured to be delivered within a delivery catheter. In some embodiments, the device assembly is deployed via relative movement out of the delivery catheter. In some embodiments, the expandable sealing skirt is self-expandable when the device assembly is deployed. In some embodiments, the expandable sealing skirt is configured to self-expand against the vessel wall instantaneously, in about 0.001 second to about 1 minute after it is out of the delivery catheter. In some embodiments, the expandable sealing skirt comprises from a 2× to a 30×, a 3× to a 20×, a 5× to a 30×, a 10× to a 30×, a 2× to a 20×, at least 2×, at least 5×, at least 10×, 1.5× to 20×, 1.5× to 30×, at most 20×, at most 10×, or at most a 30× volumetric expansion from an collapsed state to an expanded state. In some embodiments, the protruding cells comprise from a 2× to a 30×, a 3× to a 20×, a 5× to a 30×, a 10× to a 30×, a 2× to a 20×, at least 2×, at least 5×, at least 10×, 1.5× to 20×, 1.5× to 30×, at most 20×, at most 10×, or at most a 30× volumetric expansion from an collapsed state to an expanded state. In some embodiments, the device assembly comprises sutures coupling the expandable sealing skirt to the stent frame. In some embodiments, the expandable sealing skirt is coupled by the sutures to the stent frame at one or more proximally-facing edges of protruding cells. In some embodiments, the expandable sealing skirt is coupled by the sutures to the stent frame at the intersection of the non-protruding region and the protruding region along a proximal edge of the protruding cells. In some embodiments, the expandable sealing skirt is coupled by the sutures to the stent frame at the distal legs of the most distal layer of the first layer and second layer of the stent frame. In some embodiments, the expandable sealing skirt is coupled by the sutures to the stent frame at one or more proximal facing legs of the most proximal layer of the first layer and second layer of the stent frame. In some embodiments, the expandable sealing skirt is coupled by the sutures to the stent frame at one or more distal facing legs of the most distal layer of the first layer and second layer of the stent frame. In some embodiments, the expandable skirt is biocompatible and biostable when the device assembly is implanted in the human patient. In some embodiments, the expandable skirt is attached to a top, middle, or bottom portion of the stent frame. In some embodiments, the expandable skirt is compressible instantaneously within a time period of about 0.001 second to about 1 minute. In some embodiments, the non-protruding region is configured to provide a backing for the protruding region thereby preventing the protruding region from bulging inward along the radial direction. In some embodiments, the non-protruding region is permanently integrated with the protruding region. In some embodiments, the non-protruding region is at least partly located within the stent frame when coupled to the stent frame. In some embodiments, a maximal protruding thickness of the protruding region along the radial direction is in the range of about 3 mm to about 1 cm or 3 mm to 1 cm.

Provided herein is a method of endovascular prosthesis implantation with an expandable skirt in a human patient using the device assembly herein, the method comprising: delivering the device assembly within a delivery catheter in the collapsed delivery configuration to a preselected location within the human patient, deploying the device assembly by: relative movement of the delivery catheter with respect to the device assembly thereby allowing the stent frame and the expandable skirt to self-expand or expand in a controlled manner against a vessel wall. In some embodiments, the method comprises recapturing the device assembly within the delivery catheter by relative movement of the delivery catheter with respect to the device assembly thereby allowing the expandable skirt to compress within the delivery catheter. In some embodiments, the method comprises retrieving the delivery catheter from the patient, the delivery catheter enclosing the device assembly therewithin in a resheathed state. In some embodiments, the controlled expansion is via controlling a balloon catheter that the expandable skirt is loaded thereon.

Provided herein is a device assembly for endovascular prosthesis implantation in a human patient, the device assembly comprising a collapsed delivery configuration and an expanded deployed configuration, and the device assembly comprising when in the expanded deployed configuration: a stent frame being tubular and having a circular cross section in the expanded deployed configuration comprising a plurality of angularly spaced longitudinal commissure attachment posts, a plurality of stent cells formed by a plurality of longitudinal struts and rows of circumferential struts extending between and interconnecting the plurality of longitudinal struts; a valve attached to the plurality of commissure attachment posts; and an expandable sealing skirt being annular and coupled to the stent frame at or near a distal end of the stent frame, the expandable sealing skirt an expandable sealing skirt coupled to the stent frame, the expandable sealing skirt comprising a non-protruding region and a protruding region extending radially the expandable stent cells of the stent frame, wherein the rows of circumferential struts includes at least a first row of circumferential struts adjacent the distal end of a valve and a second row of circumferential struts adjacent a proximal end of the valve, wherein the struts of the first row are thicker than the struts of the second row. In some embodiments, at least one row of circumferential struts includes pairs of circumferential struts extending between two longitudinal struts, the struts of each pair having adjacent ends interconnected by a generally U-shaped crown portion defining a gap between the adjacent ends. In some embodiments, an angle between each pair of struts is between about 90 and 110 degrees. In some embodiments, the stent frame comprises a nickel cobalt chromium alloy. In some embodiments, the nickel cobalt chromium alloy comprises MP35N. In some embodiments, the device comprises a reinforcing bar positioned against for reinforcing the attachments between commissures of the valve and the commissure attachment posts.

Provided herein is a device assembly for endovascular prosthesis implantation in a human patient, the device assembly comprising a collapsed delivery configuration and an expanded deployed configuration, and the device assembly comprising when in the expanded deployed configuration: a stent frame comprising a plurality of longitudinally rigid support beams of fixed length; a first layer, a second layer, and a third layer of expandable stent cells, the layers stacked in a longitudinal direction, wherein each expandable stent cell of the first layer comprises a substantially diamond shape, wherein expandable cells of the second layer comprises at least a shape that is substantially diamond and flares outwardly in a radial direction and a substantially concave hexagon shape adjacent thereto, and wherein each of the expandable cells of the third layer comprising two of said support beams; a valve attached to the plurality of support beams; and an expandable sealing skirt coupled to the stent frame, the expandable sealing skirt comprising a non-protruding region and a protruding region extending radially the expandable stent cells of the stent frame. In some embodiments, a protruding thickness of the protruding region along the radial direction is spatially variable at least along a longitudinal direction. In some embodiments, the protruding region comprises protruding cells and connecting regions connecting the protruding cells, wherein the protruding cells expand radially beyond the expandable stent cells. In some embodiments, the protruding cells comprise a pattern reflecting a cell pattern of the stent frame, or wherein the protruding cells comprise the pattern reflecting a portion of the cell pattern of the stent frame, or wherein one or more of the protruding cells comprise the pattern reflecting the cell pattern of the stent frame and one or more of the protruding cells comprise a second pattern reflecting a portion of the cell pattern of the stent frame. In some embodiments, the protruding cells extend through one or more of the expandable stent cells in the first layer. In some embodiments, the connecting regions are coincident with one or more legs of stent cells, or are coincident with at least one or more inflections, or a combination thereof. In some embodiments, the connecting regions are coincident with a portion of one or more legs, or are coincident with a portion of at least one or more inflections, or a combination thereof. In some embodiments, when the device assembly is in the expanded deployed configuration, one or more of the protruding cells comprises a cross section along a radial direction that is substantially a triangle or rectangle. In some embodiments, the protruding region forms a protruding ring. In some embodiments, the protruding ring when viewed longitudinally from the proximal to distal end of the protruding region, has protruding cells around an entire circumference of the protruding region. In some embodiments, the protruding cells, the connecting region, or both, comprises foam. In some embodiments, the foam has an open pore structure, a closed pore structure, or a combination. In some embodiments, the foam has a controlled porosity. In some embodiments, the foam has a uniform porosity. In some embodiments, the foam has a variable porosity. In some embodiments, about 5-500 micrometers. In some embodiments, the plurality of support beams are provided with bores for allowing attachment of the valve or the expandable sealing skirt thereto. In some embodiments, the stent frame comprises a top or proximal portion, and a bottom or distal portion. In some embodiments, the top portion is more proximal than the bottom portion. In some embodiments, the stent frame comprises a cross section that is substantially circular at the bottom portion or at the first layer of stent cells. In some embodiments, the first layer of expandable stent cells is distal to the second layer and the third layer of expandable stent cells. In some embodiments, the second layer of expandable stent cells is distal to the third layer of expandable stent cells. In some embodiments, the shape that is substantially diamond and flares outwardly in the radial direction flares out at the distal-facing legs. In some embodiments, the shape that is substantially diamond and flares outwardly in the radial direction flares out at a portion of the distal-facing legs. In some embodiments, each stent cell of the first layer of stent cells comprises a height along the longitudinal direction of about 5 mm to about 12 mm. In some embodiments, each stent cell of the second layer of stent cells comprises a height along the longitudinal direction of about 5 mm to about 18 mm. In some embodiments, each stent cell of the third layer of stent cells comprises a height along the longitudinal direction of about 25 mm to about 35 mm. In some embodiments, the stent frame comprises a maximum height along the longitudinal direction in the range of 18 mm to 25 mm. In some embodiments, the stent frame comprises a diameter perpendicular to the longitudinal direction of a cross section in the range of 20 mm to 40 mm when the stent frame is in the expanded deployed configuration as measured from an outer wall of the stent frame optionally at a distal end of the stent frame. In some embodiments, the stent frame comprises a thickness of about 0.2 mm to about 1.2 mm along a radial direction. In some embodiments, the stent frame comprises a layer of open ends proximal to the first layer of stent cells. In some embodiments, the stent frame comprises a layer of open ends distal to the third layer of stent cells. In some embodiments, one or more open ends of the layer forms at least part of a substantially triangular shape. In some embodiments, one or more open ends of the layer forms at least part of a substantially trapezoid shape. In some embodiments, one or more inflections of one or more stent cells of the plurality of stent cells comprise two stent struts directly attached together or integrally formed together. In some embodiments, one or more inflections of one or more stent cells of the plurality of stent cells comprise two stent struts directly attached together or integrally formed together thereby forming a U-shape. In some embodiments, the two stent struts remain attached when the stent frame is in the expanded deployed configuration or the collapsed delivery configuration. In some embodiments, the device assembly is configured to be delivered within a delivery catheter. In some embodiments, the device assembly is deployed via relative movement out of the delivery catheter. In some embodiments, the expandable sealing skirt is self-expandable when the device assembly is deployed. In some embodiments, the expandable sealing skirt is configured to self-expand against the vessel wall instantaneously, in about 0.001 second to about 1 minute after it is out of the delivery catheter. In some embodiments, the expandable sealing skirt comprises from a 2× to a 30×, a 3× to a 20×, a 5× to a 30×, a 10× to a 30×, a 2× to a 20×, at least 2×, at least 5×, at least 10×, 1.5× to 20×, 1.5× to 30×, at most 20×, at most 10×, or at most a 30× volumetric expansion from an collapsed state to an expanded state. In some embodiments, the protruding cells comprise from a 2× to a 30×, a 3× to a 20×, a 5× to a 30×, a 10× to a 30×, a 2× to a 20×, at least 2×, at least 5×, at least 10×, 1.5× to 20×, 1.5× to 30×, at most 20×, at most 10×, or at most a 30× volumetric expansion from an collapsed state to an expanded state. In some embodiments, the device assembly comprises sutures coupling the expandable sealing skirt to the stent frame. In some embodiments, the expandable sealing skirt is coupled by the sutures to the stent frame at one or more proximally-facing legs of protruding cells. In some embodiments, the expandable sealing skirt is coupled by the sutures to the stent frame at the distal legs of the first layer of the stent frame. In some embodiments, the expandable skirt is biocompatible and biostable when the device assembly is implanted in the human patient. In some embodiments, the expandable skirt is attached to a top, middle, or bottom portion of the stent frame. In some embodiments, the expandable skirt is compressible instantaneously within a time period of about 0.001 second to about 1 minute. In some embodiments, the non-protruding region is configured to provide a backing for the protruding region thereby preventing the protruding region from bulging inward along the radial direction. In some embodiments, the non-protruding region is permanently integrated with the protruding region. In some embodiments, the non-protruding region is at least partly located within the stent frame when coupled to the stent frame. In some embodiments, a maximal protruding thickness of the protruding region along the radial direction is in the range of about 3 mm to about 1 cm or 3 mm to 1 cm.

Provided herein is a method of endovascular prosthesis implantation with an expandable skirt in a human patient using the device assembly herein, the method comprising: delivering the device assembly within a delivery catheter in the collapsed delivery configuration to a preselected location within the human patient, deploying the device assembly by: relative movement of the delivery catheter with respect to the device assembly thereby allowing the stent frame and the expandable skirt to self-expand or expand in a controlled manner against a vessel wall. The method in some embodiments comprises recapturing the device assembly within the delivery catheter by relative movement of the delivery catheter with respect to the device assembly thereby allowing the expandable skirt to compress within the delivery catheter. The method in some embodiments comprises retrieving the delivery catheter from the patient, the delivery catheter enclosing the device assembly therewithin in a resheathed state. In some embodiments, the controlled expansion is via controlling a balloon catheter that the expandable skirt is loaded thereon.

Disclosed herein is a device assembly for transcatheter aortic valve implantation in a human patient, the device assembly comprising: a stent frame configured to provide a scaffold to the device assembly when properly deployed; a valve attached to the stent frame; optionally a pericardial tissue skirt attached to the stent frame; and an expandable sealing skirt attached to one or more of the stent frame, the valve, and the pericardial tissue skirt, the expandable sealing skirt comprising a three-dimensional geometrical shape comprising: a protruding region protruding outwardly along an radial direction against a vessel wall. In some embodiments, expandable sealing skirt further comprises a non-protruding region. In some embodiments, the protruding level is spatially variable at least along a longitudinal direction of the stent frame, when properly deployed. In some embodiments, the protruding region comprises a plurality of protruding cells. In some embodiments, the plurality of cells are arranged to conform to an arrangement of a plurality of cells of the stent frame. In some embodiments, the plurality of cells is shaped to fit into a plurality of cells of the stent frame. In some embodiments, the arrangement of the plurality of cells comprises a pattern selected from: a fully circumferential, a partially circumferential, a staggered, a triangular, a square, an oval, a partial oval, a rhomboidal shape, and a random and closed configuration. In some embodiments, each of the plurality of cells comprises a three-dimensional shape selected from: a conical, a reverse conical, a cylindrical, a hemispherical and a spherical shape. In some embodiments, the protruding region comprises a circumferential spiral ring. In some embodiments, the device assembly is configured to be delivered within a delivery catheter. In some embodiments, the device assembly is deployed via relative movement out of the delivery catheter. In some embodiments, the expandable sealing skirt is self-expandable when the device assembly is deployed. In some embodiments, the expandable skirt is configured to self-expand against the vessel wall within a few seconds, for example, in about 0.001 second to about 1 minute after it is out of the delivery catheter. In some embodiments, the expansion of the skirt is perceptively instantaneous. That is, the expansion happens so quickly that it is effectively instantaneous within the ranges or timing disclosed herein. Thus, expansion of the skirt occurs within the timing disclosed herein. In some embodiments, the expandable skirt is configured to allow up to 30× volumetric expansion from an undeployed (or compressed) state to a deployed state. In some embodiments, the three-dimensional shape is selected from: a conical, a reverse conical, a cylindrical, and a spherical shape. In some embodiments, the expandable skirt is attached to one or more of the stent frame, the valve, and the pericardial tissue skirt via a conventional suturing method with conventional suture material. In some embodiments, the expandable skirt is biocompatible and biostable when the device assembly is implanted in the human patient. In some embodiments, the expandable skirt comprises foam. In some embodiments, the expandable skirt is attached to a top, middle, or bottom portion of the stent frame. In some embodiments, the expandable skirt is compressible within a time period of about 0.001 second to about 10 seconds, for example, as less as about 0.1 second. In some embodiments, the compression of the skirt is perceptively instantaneous. That is, the compression happens so quickly that it is effectively instantaneous in the ranges or timing disclosed herein. Thus, compression of the skirt occurs within the timing disclosed herein.

Disclosed herein is an expandable sealing skirt for use with a transcatheter aortic valve implantation device for a human patient, the expandable sealing skirt comprising: a three-dimensional geometrical shape comprising: a non-protruding region; and a protruding region protruding outwardly along an radial direction against a vessel wall; and an attachment element configured to attach the expandable skirt to one or more of a stent frame, a valve, and a pericardial tissue skirt. In some embodiments, expandable sealing skirt further comprises a non-protruding region. In some embodiments, the protruding level is spatially variable at least along a longitudinal direction of the stent frame, when properly deployed. In some embodiments, the protruding region comprises a plurality of protruding cells. In some embodiments, the plurality of cells are arranged to conform to an arrangement of a plurality of cells of the stent frame. In some embodiments, the plurality of cells is shaped to fit into a plurality of cells of the stent frame. In some embodiments, each of the plurality of cells comprises a shape selected from: a fully circumferential, a partially circumferential, a staggered, a triangular, a square, an oval, a partial oval, a rhomboidal shape, and a random and closed configuration. In some embodiments, the skirt is configured to be delivered with the stent frame, the valve, and the pericardial tissue skirt within a delivery catheter. In some embodiments, the skirt is deployed via relative movement out of the delivery catheter. In some embodiments, the skirt is self-expandable when the skirt is properly deployed. In some embodiments, the expandable skirt is configured to allow 30× volumetric expansion from an undeployed state to a deployed state. In some embodiments, the expandable skirt is configured to expand against the vessel wall instantaneously within a few seconds, for example, in about 0.001 second to about 1 minute after it is out of the delivery catheter. In some embodiments, the expansion of the skirt is perceptively instantaneous. That is, the expansion happens so quickly that it is effectively instantaneous within the ranges or timing disclosed herein. Thus, expansion of the skirt occurs within the timing disclosed herein. In some embodiments, the expandable skirt comprises foam. In some embodiments, the three-dimensional shape is selected from: a conical, a reverse conical, a cylindrical, and a spherical shape. In some embodiments, each of the plurality of cells comprises a three-dimensional shape selected optionally from: a conical, a reverse conical, a cylindrical, a hemispherical and a spherical shape. In some embodiments, the attachment element is configured to be sutured to one or more of the stent frame, the valve, and the pericardial tissue skirt via a conventional suturing method with conventional suture material. In some embodiments, the expandable skirt is biocompatible and biostable when the device assembly is implanted in the human patient. In some embodiments, the expandable skirt is attached to a top, middle, or bottom portion of the stent frame. In some embodiments, the expandable skirt is compressible instantaneously within a time period of about 0.001 second to about 10 seconds, for example, as less as about 0.1 second. In some embodiments, the compression of the skirt is perceptively instantaneous. That is, the compression happens so quickly that it is effectively instantaneous in the ranges or timing disclosed herein. Thus, compression of the skirt occurs within the timing disclosed herein.

Disclosed herein is a method of transcatheter valve implantation with an expandable skirt in a human patient, the method comprising: delivering a device assembly within a delivery catheter in a un-deployed state to a preselected location within the human patient, wherein the device assembly comprising a stent frame, a valve attached thereto, optionally a pericardial tissue skirt or a PET/Dacron skirt, and an expandable skirt attached to one or more of the stent frame, valve, and pericardial skirt, and wherein the expandable skirt comprises a three-dimensional geometrical shape comprising: a protruding region protruding outwardly at least along an radial direction against a vessel wall; and an attachment element configured to attach the expandable skirt to one or more of a stent frame, a valve, and a pericardial tissue skirt; and deploying the device assembly by relative movement of the delivery catheter with respect to the device assembly thereby allowing the expandable skirt to self-expand against a vessel wall or allowing the expandable skirt to expand in a controlled manner against a vessel wall.

In some embodiments, the method herein further comprises recapturing the device assembly within the delivery catheter by relative movement of the delivery catheter with respect to the device assembly thereby allowing the expandable skirt to compress within the delivery catheter. In some embodiments, the method herein further comprises retrieving the delivery catheter from the patient, the delivery catheter enclosing the device assembly therewithin in a resheathed state.

BRIEF DESCRIPTION OF THE DRAWINGS

A better understanding of the features and advantages of the present subject matter will be obtained by reference to the following detailed description that sets forth illustrative embodiments and the accompanying drawings of which:

FIGS. 1A-1D show non-limiting exemplary embodiments of the expandable sealing skirt in a deployed state (alternatively referred to herein as an expanded sealing skirt or deployed sealing skirt, or sealing skirt) with a COREVALVE® stent frame and valve;

FIG. 1N-1P show non-limiting exemplary embodiments of the expandable sealing skirt in a deployed state (alternatively referred to herein as an expanded sealing skirt or deployed sealing skirt, or sealing skirt) with a ACURATE® stent frame and valve;

FIGS. 4E-4H show a non-limiting exemplary embodiment of the expandable sealing skirt; in this case, the expandable skirt in different views before assembling on to the PORTICO® stent;

FIGS. 4I-4L show a non-limiting exemplary embodiment of the expandable sealing skirt; in this case, the expandable skirt in different views before assembling on to the SAPIEN® stent;

FIGS. 4M-4P show a non-limiting exemplary embodiment of the expandable sealing skirt; in this case, the expandable skirt in different views before assembling on to the ACURATE® stent;

FIGS. 5E-5H show a non-limiting exemplary embodiment of the expandable sealing skirt; in this case, the expandable skirt in different views before assembling on to the PORTICO® stent;

FIGS. 5I-5L show a non-limiting exemplary embodiment of the expandable sealing skirt; in this case, the expandable skirt in different views before assembling on to the SAPIEN® stent;

FIGS. 5M-5P show a non-limiting exemplary embodiment of the expandable sealing skirt; in this case, the expandable skirt in different views before assembling on to the ACURATE stent;

DETAILED DESCRIPTION

Figure 1A:
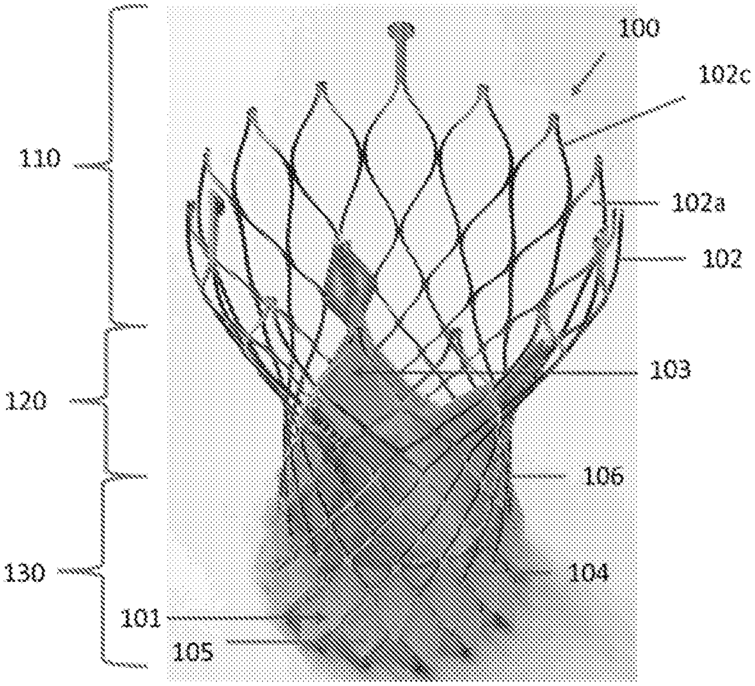

Significant paravalvular regurgitation (PVR) after transcatheter aortic valve implantation (TAVI), due to incomplete annular sealing, is common, occurring in about 10-20% of cases and is the most significant predictor of long-term mortality. In a registry of 3195 TAVI recipients, postprocedural PVR of at least mild-to-moderate (i.e., PVR≥grade 2) severity is observed in about 22% of self-expanding and about 13% of balloon-expandable TAVI cases. PVR≥grade 2 was the strongest independent predictor of 1-year mortality and associated with high rates of death in a number of patient subgroups including renal failure (43%) and PVR<grade 2 at baseline (31%). A meta-analysis of 45 studies incorporating 12926 patients showed that moderate or severe PVR was common post TAVI, occurring in about 11.7% of cases and associated with increased mortality at 30 days and 1 year. It has been found that that though PVR generally remains stable after balloon expandable TAVI, even mild PVR (about 40% of all TAVI patients) is associated with increased late mortality. The prognostic significance of PVR is further reinforced by a multivariate analysis of 2515 TAVI patients that demonstrated that even mild PVR alone is associated with increased late mortality post TAVI.

Paravalvular leak can result from prosthesis-annulus incongruence (i.e. lack of apposition between the TAVI prosthesis and the aortic annulus) and results in leak sites around the transcatheter heart valve. TAVI entails implanting a circular bioprosthesis into a dynamic, oval-shaped aortic annulus. Leakage occurs due to various reasons which may include the presence of bulky calcium protrusions, the presence of a widely varying annular anatomy, incorrect sizing and/or mis-positioning of the device. In a clinical study of 35 aortic stenosis (AS) patients where a self-expanding stent is deployed intraoperatively inside the aortic valve before surgical aortic valve replacement (AVR), the incidence of gaps predisposing to paravalvular leaks can be very common, occurring in about 58% and about 43% respectively of patients with tricuspid and bicuspid aortic valves. Paravalvular leak resulting in aortic regurgitation is a common and serious complication across all TAVI platforms that have significant adverse prognostic impact on therapy outcomes. The promising TAVI data in high-risk patients have fueled immense interest in expanding the application of TAVI to younger and lower risk patients with AS. However, PVR remains the major limitation to broadening transcatheter intervention to a wider patient population.

To mitigate the risk of PVR, transcatheter aortic valves are systematically oversized relative to the aortic annulus in an effort to reduce prosthesis-annulus incongruence. However, transcatheter valve oversizing can be problematic and a major risk factor for catastrophic aortic annular rupture (CIA), a complication that is almost always fatal. Furthermore, transcatheter valve oversizing may increase risk for coronary artery occlusion, and predispose to damage to the cardiac conduction system. A randomized clinical trial comparing balloon expandable and self-expanding TAVI confirms the superior leak results for balloon-expandable TAVI, but also highlights the high rate of acute procedural interventions undertaken to reduce PVR. In patients receiving self-expanding TAVI, moderate or severe PVR can be present in 42.5% of patients immediately after valve implant.

This results in about 49% of self-expanding TAVI patients receiving balloon post dilatation for optimization of leak, an intervention that is associated with increased risk of annular rupture, stroke and prosthetic valve leaflet damage. Furthermore, the presence of significant PVR is a major contributor to about 5.8% of self-expanding valve recipients acutely having a second transcatheter valve deployed within the first valve (valve-in-valve) with attendant escalation in procedural risks. Finally, the use of simple fabric or polymeric sealing cuffs with limited conformability and expansibility such as the Edwards SAPIEN® 3 valve may lead to incremental reductions in PVR but not elimination of the problem, with about 44% of SAPIEN® 3 valve recipients having mild or greater PVR after implantation. In sum, fundamental limitations and risks exist in current approaches to mitigate PVR.

Limitations of existing arts for heart valve replacement include but are not limited to: limited conformability to paravalvular leak-sites due to passive nature of sealing technologies or features (e.g. thickened pericardial skirt on the outside of the stent has limited outward extension; the existing products, e.g., PORTICO® ®, which has no sealing skirt on the outside is even less conformable; (2) additional layering with pericardial skirt (such as in the COREVALVE® ENOLUTE®) causes increase in device profile; (3) need for excessive oversizing which tends to have an impact of creating issues with the conduction system of the heart and therefore leads to an increased risk of pacemaker implantation, and further, excessive oversizing in balloon-expandable devices (such as the SAPIEN® ® valve series) carry the catastrophic risk of aortic root rupture; (4) need for post-dilation is reduced which carries a significant mortality risk from stroke.

While mitral valve repair and replacement (TMVR) has a shorter history as compared to TAVI, it too suffers from the drawbacks present in TAVI, such as limited conformability to paravalvular leak-sites, increased device profile due to layering needs with skirts, need for device oversizing, and stroke risk due to post-dilation need. Skirts as described herein are appropriate for attachment to replacement mitral valves and their supporting stent frames.

Provided herein is a device assembly for endovascular prosthesis implantation in a human patient, the device assembly comprising a collapsed delivery configuration and an expanded deployed configuration and comprising when in the expanded deployed configuration: a stent frame comprising a generally conical section, a flared section, and a constriction region between the conical section and the flared section, and a first layer and a second layer of expandable stent cells in the generally conical section, the layers stacked in a longitudinal direction, wherein each of the plurality of expandable stent cells of the first and second layers comprise a cell pattern defined by a first zig-zag extending in the longitudinal direction comprising a first leg and a second leg coupled thereto by a first inflection, and a second zig-zag extending in the longitudinal direction comprising a third leg coupled to a fourth leg by a second inflection, wherein the first leg is coupled to the third leg at a third inflection, and the second leg is coupled to the fourth leg at a fourth inflection, forming thereby a substantially diamond shape, wherein the first leg and the second leg are unequal in length; a valve attached to the stent frame; and an expandable sealing skirt coupled to the stent frame at the generally conical section, the expandable sealing skirt comprising a non-protruding region and a protruding region extending radially beyond the expandable stent cells in the generally conical section of the stent frame. In some embodiments, a protruding thickness of the protruding region along the radial direction is spatially variable at least along a longitudinal direction. In some embodiments, the protruding region comprises protruding cells and connecting regions connecting the protruding cells, wherein the protruding cells expand radially beyond the expandable stent cells. In some embodiments, the protruding cells comprise a pattern reflecting the cell pattern of the stent frame in the conical section, or wherein the protruding cells comprise a pattern reflecting a portion of the cell pattern of the stent frame in the conical section, or wherein one or more of the protruding cells comprise a pattern reflecting the cell pattern of the stent frame in the conical section and one or more of the protruding cells comprise a second pattern reflecting a portion of the cell pattern of the stent frame in the conical section. In some embodiments, the protruding cells extend through one or more of the expandable stent cells in the first layer and the second layer. In some embodiments, the connecting regions are coincident with one or more of the first leg through the fourth leg, or are coincident with at least one or more of the first through the fourth inflections, or a combination thereof. In some embodiments, the connecting regions are coincident with a portion of one or more of the first leg through the fourth leg, or are coincident with a portion of at least one or more of the first through the fourth inflections, or a portion or a combination thereof. In some embodiments, the device assembly is in the expanded deployed configuration, one or more of the protruding cells comprises a cross section along a radial direction that is substantially a rectangle, or a triangle. In some embodiments, the device assembly is in the expanded deployed configuration, one or more of the protruding cells comprises a cross section along a radial direction that protrudes less through the expandable stent cell at its proximal end than it protrudes through the expandable stent cell at its distal end. In some embodiments, the protruding region forms a protruding ring. In some embodiments, the protruding ring when viewed longitudinally from the proximal to distal end of the protruding region, has protruding cells around the entire circumference of the protruding region. In some embodiments, the connecting region, or both, comprises foam. In some embodiments, the foam has an open pore structure, a closed pore structure, or a combination. In some embodiments, the foam has a controlled porosity. In some embodiments, the foam has a uniform porosity. In some embodiments, the foam has a variable porosity. In some embodiments, the foam has a porosity of about 5-500 micrometers. In some embodiments, the more than one layer comprises five layers. In some embodiments, stent cells in a first layer are no smaller than the stent cells in a second layer that is more distal to the first layer when the stent frame is in the expanded deployed configuration. In some embodiments, stent cells from a first layer comprise a shape that is substantially identical to a second shape of the stent cells from a second layer when the stent frame is in the expanded deployed configuration. In some embodiments, the stent frame comprises up to thirty total zig-zags inclusive of the first and second zig-zags, each zig-zag extending in the longitudinal direction, and each zig zag coupled to adjacent zig zags at inflections to form a device assembly in a tube shape wherein each of the two layers each comprises closed diamond shaped cells. In some embodiments, when the stent frame is in the expanded deployed configuration and laid flat, the plurality of stent cells comprises one or more diamond shapes. In some embodiments, the stent frame comprises a proximal or top portion, and a bottom or distal portion, wherein at least part of the generally conical section is in the bottom portion, wherein at least part of the flared section is in the top portion. In some embodiments, the stent frame comprises a cross section that is substantially circular at the top portion, the bottom portion, or both when the stent frame is in the expanded deployed configuration. In some embodiments, each stent cell of the one or more layers of stent cells comprises a height along the longitudinal direction of about 6 mm to about 12 mm when the stent frame is in the expanded deployed configuration. In some embodiments, the stent frame comprises a maximum height along the longitudinal direction in the range of 30 mm to 45 mm when the stent frame is in the expanded deployed configuration. In some embodiments, the stent frame comprises a diameter (outer diameter) of a cross section perpendicular to the longitudinal direction in the range of 15 mm to 40 mm when the stent frame is in the expanded deployed configuration as measured from an outer wall of the stent frame optionally at a distal end of the stent frame. In some embodiments, the stent frame comprises a thickness of about 0.2 mm to about 1 mm along a radial direction. In some embodiments, the stent frame comprises a layer of open ends proximal to a most proximal layer of stent cells. In some embodiments, the stent frame comprises a layer of open ends distal to a most distal layer of stent cells. In some embodiments, one or more inflections of one or more stent cells of the plurality of stent cells comprise two stent struts directly attached together or integrally formed together. In some embodiments, the two stent struts remain attached when the stent frame is in the expanded deployed configuration or the collapsed delivery configuration. In some embodiments, the device assembly is configured to be delivered within a delivery catheter. In some embodiments, the expandable sealing skirt is self-expandable when the device assembly is deployed. In some embodiments, the expandable sealing skirt is configured to self-expand against the vessel wall instantaneously, in about 0.001 second to about 1 minute after it is out of the delivery catheter. In some embodiments, the expandable sealing skirt comprises from a 2× to a 30×, a 3× to a 20×, a 5× to a 30×, a 10× to a 30×, a 2× to a 20×, at least 2×, at least 5×, at least 10×, 1.5× to 20×, 1.5× to 30×, at most 20×, at most 10×, or at most a 30× volumetric expansion from an collapsed state to an expanded state. In some embodiments, the protruding cells comprise from a 2× to a 30×, a 3× to a 20×, a 5× to a 30×, a 10× to a 30×, a 2× to a 20×, at least 2×, at least 5×, at least 10×, 1.5× to 20×, 1.5× to 30×, at most 20×, at most 10×, or at most a 30× volumetric expansion from an collapsed state to an expanded state. In some embodiments, the device assembly comprises sutures coupling the expandable sealing skirt to the stent frame. In some embodiments, the expandable sealing skirt is coupled by the sutures to the stent frame at one or more proximally-facing edges of protruding cells. In some embodiments, the expandable sealing skirt is coupled by the sutures to the stent frame at the intersection of the non-protruding region and the protruding region along a proximal edge of the protruding cells. In some embodiments, the expandable sealing skirt is coupled by the sutures to the stent frame at the distal legs of the most distal layer of the first layer and second layer of the stent frame. In some embodiments, the expandable sealing skirt is coupled by the sutures to the stent frame at one or more proximal facing legs of the most proximal layer of the first layer and second layer of the stent frame. In some embodiments, the expandable sealing skirt is coupled by the sutures to the stent frame at one or more distal facing legs of the most distal layer of the first layer and second layer of the stent frame. In some embodiments, the expandable skirt is biocompatible and biostable when the device assembly is implanted in the human patient. In some embodiments, the expandable skirt is attached to a top, middle, or bottom portion of the stent frame. In some embodiments, the expandable skirt is compressible instantaneously within a time period of about 0.001 second to about 1 minute. In some embodiments, the device assembly comprises a pericardial tissue skirt attached to the stent frame or a PET or Dacron skirt. In some embodiments, the non-protruding region is permanently integrated with the protruding region. In some embodiments, the non-protruding region is at least partly located within the stent frame when coupled to the stent frame. In some embodiments, a maximum protruding thickness of the protruding region along the radial direction is in the range of about 3 mm to about 1 cm, or 3 mm to 1 cm.

Provided herein is a method of endovascular prosthesis implantation with an expandable skirt in a human patient using the device assembly herein, the method comprising: delivering the device assembly within a delivery catheter in the collapsed delivery configuration to a preselected location within the human patient, deploying the device assembly by: relative movement of the delivery catheter with respect to the device assembly thereby allowing the stent frame and the expandable skirt to self-expand or expand in a controlled manner against a vessel wall. In some embodiments, the method comprises recapturing the device assembly within the delivery catheter by relative movement of the delivery catheter with respect to the device assembly thereby allowing the expandable skirt to compress within the delivery catheter. In some embodiments, the method comprises retrieving the delivery catheter from the patient, the delivery catheter enclosing the device assembly therewithin in a resheathed state. In some embodiments, the method comprises controlled expansion is via controlling a balloon catheter that the expandable skirt is loaded thereon.

Provided herein is a device assembly for endovascular prosthesis implantation in a human patient, the device assembly comprising a collapsed delivery configuration and an expanded deployed configuration, and the device assembly comprising: a stent frame comprising a plurality of expandable stent cells arranged in more than one layer and stacked in a longitudinal direction, wherein in the expanded deployed configuration the stent frame comprises a substantially columnar section and a flared section, wherein two or more layers of stent cells are of a substantially diamond shape, and wherein the stent frame comprises non-expandable connectors positioned between the substantially conical section or the substantially columnar section and the flared section; a valve attached to the stent frame; and an expandable sealing skirt coupled to the stent frame at the substantially columnar section, the expandable sealing skirt comprising a protruding region configured to expand radially past the more than one layers of stent cells of the stent frame when the device assembly is in the expanded deployed configuration and a non-protruding region. In some embodiments, a protruding thickness of the protruding region along the radial direction is spatially variable at least along a longitudinal direction. In some embodiments, the protruding region comprises protruding cells and connecting regions connecting the protruding cells, wherein the protruding cells expand radially beyond the expandable stent cells. In some embodiments, the protruding cells comprise a pattern reflecting the cell pattern of the stent frame in the columnar section, or wherein the protruding cells comprise a pattern reflecting a portion of the cell pattern of the stent frame in the columnar section, or wherein one or more of the protruding cells comprise a pattern reflecting the cell pattern of the stent frame in the columnar section and one or more of the protruding cells comprise a second pattern reflecting a portion of the cell pattern of the stent frame in the columnar section. In some embodiments, the protruding cells extend through one or more of the expandable stent cells in the first layer and the second layer. In some embodiments, the connecting regions are coincident with one or more of a first leg through a fourth leg of the diamond shape of the stent cell, or are coincident with at least one or more of a first through fourth inflection of the diamond shape of the stent cell, or a combination thereof. In some embodiments, the connecting regions are coincident with a portion of one or more of a first leg through a fourth leg of the diamond shape of the stent cell, or are coincident with a portion of at least one or more of a first through a fourth inflections of the diamond shape of the stent cell, or a portion or a combination thereof. In some embodiments, when the device assembly is in the expanded deployed configuration, one or more of the protruding cells comprises a cross section along a radial direction that is substantially a rectangle, or a triangle. In some embodiments, when the device assembly is in the expanded deployed configuration, one or more of the protruding cells comprises a cross section along a radial direction that protrudes less through the expandable stent cell at its proximal end than it protrudes through the expandable stent cell at its distal end. In some embodiments, the protruding region forms a protruding ring. In some embodiments, the protruding ring, when viewed longitudinally from the proximal to distal end of the protruding region, has protruding cells around the entire circumference of the protruding region. In some embodiments, the expandable skirt comprises foam. In some embodiments, the foam has an open pore structure, a closed pore structure, or a combination. In some embodiments, the foam has a controlled porosity. In some embodiments, the foam has a uniform porosity. In some embodiments, the foam has a variable porosity. In some embodiments, the foam has a porosity of about 5-500 micrometers. In some embodiments, the more than one layer comprises four or five layers. In some embodiments, stent cells in a first layer of the substantially columnar section is smaller than the stent cells in a second layer that is more distal to the first layer when the stent frame is in the expanded deployed configuration. In some embodiments, stent cells in a first layer comprise a shape that is substantially identical to a second shape of the stent cells from a second layer when the stent frame is in the expanded deployed configuration. In some embodiments, when the stent frame is in the expanded deployed configuration the plurality of stent cells comprises one or more shapes of: a diamond shape and a rhomboid shape. In some embodiments, stent cells from a most proximal layer comprise a substantially diamond shape when the stent frame is in the expanded deployed configuration. In some embodiments, stent cells from a most distal layer comprise a substantially diamond shape when the stent frame is in the expanded deployed configuration. In some embodiments, each stent cell comprises a substantially identical shape when the stent frame is in the expanded deployed configuration. In some embodiments, each stent cell comprises a substantially diamond shape when the stent frame is in the expanded deployed configuration. In some embodiments, the stent frame comprises a top portion, a bottom portion, and optionally a middle portion. In some embodiments, at least part of the substantially columnar section is in the bottom portion. In some embodiments, at least part of the flared section is in the top portion. In some embodiments, the top portion is more proximal than the bottom portion, and directly attached to the bottom portion. In some embodiments, the top portion and the bottom portion are connected by the connectors. In some embodiments, the connectors comprise one or more straight struts and one or more loops. In some embodiments, a height of the connectors is smaller than the height of the stent cells. In some embodiments, each of the connectors connects two stent cells, and wherein the two stent cells do not share any vertices. In some embodiments, the stent frame comprises a cross section that is substantially circular at the top portion, the bottom portion, or both when the stent frame is in the expanded deployed configuration. In some embodiments, each stent cell of the one or more layers of stent cells comprises a height along the longitudinal direction of about 8 mm to about 15 mm, when the stent frame is in the expanded deployed configuration. In some embodiments, each stent cell of the one or more layers of stent cells comprises a height along the longitudinal direction of about 20 mm to about 40 mm, when the stent frame is in the expanded deployed configuration. In some embodiments, the stent frame comprises a height along the longitudinal direction in the range of 40 mm to 60 mm, when the stent frame is in the expanded deployed configuration. In some embodiments, wherein the stent frame comprises a diameter of a cross section perpendicular to the longitudinal direction in the range of 15 mm to 40 mm when the stent frame is in the expanded deployed configuration, as measured from an outer wall of the stent frame optionally at a distal end of the stent frame. In some embodiments, the stent frame comprises a thickness of about 0.2 mm to about 1 mm along a radial direction. In some embodiments, the stent frame comprises a layer of open ends proximal to a most proximal layer of stent cells. In some embodiments, the stent frame comprises a layer of open ends distal to a most distal layer of stent cells. In some embodiments, one or more inflections of one or more stent cells of the plurality of stent cells comprise two stent struts directly attached together or integrally formed together. In some embodiments, the protruding region comprises a protruding ring. In some embodiments, the device assembly is configured to be delivered within a delivery catheter. In some embodiments, the device assembly is deployed via relative movement out of the delivery catheter. In some embodiments, the expandable sealing skirt is self-expandable when the device assembly is deployed. In some embodiments, the expandable skirt is configured to self-expand against the vessel wall instantaneously, in about 0.001 second to about 1 minute after it is out of the delivery catheter. In some embodiments, the expandable sealing skirt comprises from a 2× to a 30×, a 3× to a 20×, a 5× to a 30×, a 10× to a 30×, a 2× to a 20×, at least 2×, at least 5×, at least 10×, 1.5× to 20×, 1.5× to 30×, at most 20×, at most 10×, or at most a 30× volumetric expansion from an collapsed state to an expanded state. In some embodiments, the protruding cells comprise from a 2× to a 30×, a 3× to a 20×, a 5× to a 30×, a 10× to a 30×, a 2× to a 20×, at least 2×, at least 5×, at least 10×, 1.5× to 20×, 1.5× to 30×, at most 20×, at most 10×, or at most a 30× volumetric expansion from an collapsed state to an expanded state. In some embodiments, the expandable skirt is attached to one or more of the stent frame, the valve, and a pericardial tissue skirt using sutures. In some embodiments, the expandable skirt is attached to the stent frame at one or more edges of protruding cells of the protruding region. In some embodiments, the device assembly comprises sutures coupling the expandable sealing skirt to the stent frame. In some embodiments, the expandable sealing skirt is coupled by the sutures to the stent frame at one or more proximally-facing edges of protruding cells. In some embodiments, the expandable sealing skirt is coupled by the sutures to the stent frame at the intersection of the non-protruding region and the protruding region along a proximal edge of the protruding cells. In some embodiments, the expandable sealing skirt is coupled by the sutures to the stent frame at the distal legs of the most distal layer of the first layer and second layer of the stent frame. In some embodiments, the expandable sealing skirt is coupled by the sutures to the stent frame at one or more proximal facing legs of the most proximal layer of the first layer and second layer of the stent frame. In some embodiments, the expandable sealing skirt is coupled by the sutures to the stent frame at one or more distal facing legs of the most distal layer of the first layer and second layer of the stent frame. In some embodiments, the expandable skirt is biocompatible and biostable when the device assembly is implanted in the human patient. In some embodiments, the expandable skirt is attached to a top, middle, or bottom portion of the stent frame. In some embodiments, the expandable skirt is compressible instantaneously within a time period of about 0.001 second to about 1 minute. In some embodiments, the device assembly comprises a pericardial tissue skirt attached to the stent frame or a PET or Dacron skirt. In some embodiments, the non-protruding region is permanently integrated with the protruding region. In some embodiments, the non-protruding region is at least partly located within the stent frame when properly attached to the stent frame.

Provided herein is a method of endovascular prosthesis implantation with an expandable skirt in a human patient using the device assembly herein, the method comprising: delivering the device assembly within a delivery catheter in the collapsed delivery configuration to a preselected location within the human patient, deploying the device assembly by: relative movement of the delivery catheter with respect to the device assembly thereby allowing the stent frame and the expandable skirt to self-expand or expand in a controlled manner against a vessel wall. In some embodiments, the method comprises recapturing the device assembly within the delivery catheter by relative movement of the delivery catheter with respect to the device assembly thereby allowing the expandable skirt to compress within the delivery catheter. In some embodiments, the method comprises retrieving the delivery catheter from the patient, the delivery catheter enclosing the device assembly therewithin in a resheathed state. In some embodiments, the controlled expansion is via controlling a balloon catheter that the expandable skirt is loaded thereon.

Provided herein is a device assembly for endovascular prosthesis implantation in a human patient, the device assembly comprising a collapsed delivery configuration and an expanded deployed configuration, and the device assembly comprising when in the expanded deployed configuration: a stent frame being tubular and having a circular cross section comprising a plurality of longitudinally rigid support beams of fixed length, and a first layer and a second layer of expandable stent cells, the layers stacked in a longitudinal direction, wherein the second layer is distal to the first layer and is a distalmost layer of stent cells in the stent frame, wherein each of the plurality of expandable stent cells of the first layer comprises a first shape that is a substantially hexagon shape, and wherein each of the plurality of expandable stent cells of the second layer comprises a second shape that is a substantially diamond shape; a valve attached to the plurality of support beams; and an expandable sealing skirt coupled to the stent frame, the expandable sealing skirt comprising a non-protruding region and a protruding region extending radially the expandable stent cells of the stent frame. In some embodiments, the stent frame comprises extending legs extending distally from the second layer. In some embodiments, the protruding region is positioned distal and adjacent to the second layer and between and adjacent to the extending legs. In some embodiments, a protruding thickness of the protruding region along the radial direction is spatially consistent at least along a longitudinal direction. In some embodiments, the protruding region comprises protruding cells and connecting regions connecting the protruding cells, wherein the protruding cells expand radially beyond the expandable stent cells. In some embodiments, the protruding cells comprise a pattern reflecting a cell pattern of the stent frame, or wherein the protruding cells comprise the pattern reflecting a portion of the cell pattern of the stent frame, or wherein one or more of the protruding cells comprise the pattern reflecting the cell pattern of the stent frame and one or more of the protruding cells comprise a second pattern reflecting a portion of the cell pattern of the stent frame. In some embodiments, the protruding cells extend through one or more of the expandable stent cells in the first layer and the second layer. In some embodiments, the connecting regions are coincident with one or more legs of stent cells, or are coincident with at least one or more inflections, or a combination thereof. In some embodiments, the connecting regions are coincident with a portion of one or more legs, or are coincident with a portion of at least one or more inflections, or a combination thereof. In some embodiments, when the device assembly is in the expanded deployed configuration, one or more of the protruding cells comprises a cross section along a radial direction that is substantially a rectangle. In some embodiments, the protruding region forms a protruding ring. In some embodiments, the protruding ring, when viewed longitudinally from the proximal to distal end of the protruding region, has protruding cells around an entire circumference of the protruding region. In some embodiments, the protruding cells, the connecting region, or both, comprises foam. In some embodiments, the foam has an open pore structure, a closed pore structure, or a combination. In some embodiments, the foam has a controlled porosity. In some embodiments, the foam has a uniform porosity. In some embodiments, the foam has a variable porosity. In some embodiments, the foam has a porosity of about 5-500 μm. In some embodiments, the plurality of support beams are provided with bores for allowing suturing or tying the valve or the expandable sealing skirt thereto. In some embodiments, the stent frame comprises a third layer and a fourth layer. In some embodiments, stent cells in a first layer that is more proximal are smaller than the stent cells in a second layer. In some embodiments, stent cells from a most proximal layer comprises a substantially diamond shape. In some embodiments, stent cells from a most proximal layer comprises a substantially hexagon shape. In some embodiments, stent cells from a most distal layer comprises a substantially diamond shape. In some embodiments, stent cells from a most distal layer comprises a substantially hexagon shape. In some embodiments, the stent frame comprises a top or proximal portion, and a bottom or distal portion. In some embodiments, the top portion is more proximal than the bottom portion In some embodiments, the stent frame comprises a cross section that is substantially circular at the top portion, the bottom portion, or both when the stent frame is in the expanded deployed. In some embodiments, each stent cell of the one or more layers of stent cells comprises a height along the longitudinal direction of about 3 mm to about 10 mm. In some embodiments, the stent frame comprises a maximum height along the longitudinal direction in the range of 18 mm to 25 mm. In some embodiments, the stent frame comprises a diameter of a cross section perpendicular to the longitudinal direction in the range of 20 mm to 40 mm when the stent frame is in the expanded deployed configuration as measured from an outer wall of the stent frame optionally at a distal end of the stent frame. In some embodiments, the stent frame comprises a thickness of about 0.2 mm to about 1 mm along a radial direction. In some embodiments, the stent frame comprises a layer of open ends proximal to a most proximal layer of stent cells. In some embodiments, the stent frame comprises a layer of open ends distal to a most distal layer of stent cells. In some embodiments, one or more open ends of the layer forms at least part of a substantially triangular shape. In some embodiments, one or more open ends of the layer forms a substantially pentagon shape. In some embodiments, one or more inflections of one or more stent cells of the plurality of stent cells comprise two stent struts directly attached together or integrally formed together. In some embodiments, the two stent struts remain attached when the stent frame is in the expanded deployed configuration or the collapsed delivery configuration. In some embodiments, the device assembly is configured to be delivered within a delivery catheter. In some embodiments, the device assembly is deployed via relative movement out of the delivery catheter. In some embodiments, the expandable sealing skirt is self-expandable when the device assembly is deployed. In some embodiments, the expandable sealing skirt is configured to self-expand against the vessel wall instantaneously, in about 0.001 second to about 1 minute after it is out of the delivery catheter. In some embodiments, the expandable sealing skirt comprises from a 2× to a 30×, a 3× to a 20×, a 5× to a 30×, a 10× to a 30×, a 2× to a 20×, at least 2×, at least 5×, at least 10×, 1.5× to 20×, 1.5× to 30×, at most 20×, at most 10×, or at most a 30× volumetric expansion from an collapsed state to an expanded state. In some embodiments, the protruding cells comprise from a 2× to a 30×, a 3× to a 20×, a 5× to a 30×, a 10× to a 30×, a 2× to a 20×, at least 2×, at least 5×, at least 10×, 1.5× to 20×, 1.5× to 30×, at most 20×, at most 10×, or at most a 30× volumetric expansion from an collapsed state to an expanded state. In some embodiments, the device assembly comprises sutures coupling the expandable sealing skirt to the stent frame. In some embodiments, the expandable sealing skirt is coupled by the sutures to the stent frame at one or more proximally-facing edges of protruding cells. In some embodiments, the expandable sealing skirt is coupled by the sutures to the stent frame at the intersection of the non-protruding region and the protruding region along a proximal edge of the protruding cells. In some embodiments, the expandable sealing skirt is coupled by the sutures to the stent frame at the distal legs of the most distal layer of the first layer and second layer of the stent frame. In some embodiments, the expandable sealing skirt is coupled by the sutures to the stent frame at one or more proximal facing legs of the most proximal layer of the first layer and second layer of the stent frame. In some embodiments, the expandable sealing skirt is coupled by the sutures to the stent frame at one or more distal facing legs of the most distal layer of the first layer and second layer of the stent frame. In some embodiments, the expandable skirt is biocompatible and biostable when the device assembly is implanted in the human patient. In some embodiments, the expandable skirt is attached to a top, middle, or bottom portion of the stent frame. In some embodiments, the expandable skirt is compressible instantaneously within a time period of about 0.001 second to about 1 minute. In some embodiments, the non-protruding region is configured to provide a backing for the protruding region thereby preventing the protruding region from bulging inward along the radial direction. In some embodiments, the non-protruding region is permanently integrated with the protruding region. In some embodiments, the non-protruding region is at least partly located within the stent frame when coupled to the stent frame. In some embodiments, a maximal protruding thickness of the protruding region along the radial direction is in the range of about 3 mm to about 1 cm or 3 mm to 1 cm.

Provided herein is a method of endovascular prosthesis implantation with an expandable skirt in a human patient using the device assembly herein, the method comprising: delivering the device assembly within a delivery catheter in the collapsed delivery configuration to a preselected location within the human patient, deploying the device assembly by: relative movement of the delivery catheter with respect to the device assembly thereby allowing the stent frame and the expandable skirt to self-expand or expand in a controlled manner against a vessel wall. In some embodiments, the method comprises recapturing the device assembly within the delivery catheter by relative movement of the delivery catheter with respect to the device assembly thereby allowing the expandable skirt to compress within the delivery catheter. In some embodiments, the method comprises retrieving the delivery catheter from the patient, the delivery catheter enclosing the device assembly therewithin in a resheathed state. In some embodiments, the controlled expansion is via controlling a balloon catheter that the expandable skirt is loaded thereon.

Provided herein is a device assembly for endovascular prosthesis implantation in a human patient, the device assembly comprising a collapsed delivery configuration and an expanded deployed configuration, and the device assembly comprising when in the expanded deployed configuration: a stent frame being tubular and having a circular cross section in the expanded deployed configuration comprising a plurality of angularly spaced longitudinal commissure attachment posts, a plurality of stent cells formed by a plurality of longitudinal struts and rows of circumferential struts extending between and interconnecting the plurality of longitudinal struts; a valve attached to the plurality of commissure attachment posts; and an expandable sealing skirt being annular and coupled to the stent frame at or near a distal end of the stent frame, the expandable sealing skirt an expandable sealing skirt coupled to the stent frame, the expandable sealing skirt comprising a non-protruding region and a protruding region extending radially the expandable stent cells of the stent frame, wherein the rows of circumferential struts includes at least a first row of circumferential struts adjacent the distal end of a valve and a second row of circumferential struts adjacent a proximal end of the valve, wherein the struts of the first row are thicker than the struts of the second row. In some embodiments, at least one row of circumferential struts includes pairs of circumferential struts extending between two longitudinal struts, the struts of each pair having adjacent ends interconnected by a generally U-shaped crown portion defining a gap between the adjacent ends. In some embodiments, an angle between each pair of struts is between about 90 and 110 degrees. In some embodiments, the stent frame comprises a nickel cobalt chromium alloy. In some embodiments, the nickel cobalt chromium alloy comprises MP35N. In some embodiments, the device comprises a reinforcing bar positioned against for reinforcing the attachments between commissures of the valve and the commissure attachment posts.

Provided herein is a device assembly for endovascular prosthesis implantation in a human patient, the device assembly comprising a collapsed delivery configuration and an expanded deployed configuration, and the device assembly comprising when in the expanded deployed configuration: a stent frame comprising a plurality of longitudinally rigid support beams of fixed length; a first layer, a second layer, and a third layer of expandable stent cells, the layers stacked in a longitudinal direction, wherein each expandable stent cell of the first layer comprises a substantially diamond shape, wherein expandable cells of the second layer comprises at least a shape that is substantially diamond and flares outwardly in a radial direction and a substantially concave hexagon shape adjacent thereto, and wherein each of the expandable cells of the third layer comprising two of said support beams; a valve attached to the plurality of support beams; and an expandable sealing skirt coupled to the stent frame, the expandable sealing skirt comprising a non-protruding region and a protruding region extending radially the expandable stent cells of the stent frame. In some embodiments, a protruding thickness of the protruding region along the radial direction is spatially variable at least along a longitudinal direction. In some embodiments, the protruding region comprises protruding cells and connecting regions connecting the protruding cells, wherein the protruding cells expand radially beyond the expandable stent cells. In some embodiments, the protruding cells comprise a pattern reflecting a cell pattern of the stent frame, or wherein the protruding cells comprise the pattern reflecting a portion of the cell pattern of the stent frame, or wherein one or more of the protruding cells comprise the pattern reflecting the cell pattern of the stent frame and one or more of the protruding cells comprise a second pattern reflecting a portion of the cell pattern of the stent frame. In some embodiments, the protruding cells extend through one or more of the expandable stent cells in the first layer. In some embodiments, the connecting regions are coincident with one or more legs of stent cells, or are coincident with at least one or more inflections, or a combination thereof. In some embodiments, the connecting regions are coincident with a portion of one or more legs, or are coincident with a portion of at least one or more inflections, or a combination thereof. In some embodiments, when the device assembly is in the expanded deployed configuration, one or more of the protruding cells comprises a cross section along a radial direction that is substantially a triangle or rectangle. In some embodiments, the protruding region forms a protruding ring. In some embodiments, the protruding ring when viewed longitudinally from the proximal to distal end of the protruding region, has protruding cells around an entire circumference of the protruding region. In some embodiments, the protruding cells, the connecting region, or both, comprises foam. In some embodiments, the foam has an open pore structure, a closed pore structure, or a combination. In some embodiments, the foam has a controlled porosity. In some embodiments, the foam has a uniform porosity. In some embodiments, the foam has a variable porosity. In some embodiments, about 5-500 micrometers. In some embodiments, the plurality of support beams are provided with bores for allowing attachment of the valve or the expandable sealing skirt thereto. In some embodiments, the stent frame comprises a top or proximal portion, and a bottom or distal portion. In some embodiments, the top portion is more proximal than the bottom portion. In some embodiments, the stent frame comprises a cross section that is substantially circular at the bottom portion or at the first layer of stent cells. In some embodiments, the first layer of expandable stent cells is distal to the second layer and the third layer of expandable stent cells. In some embodiments, the second layer of expandable stent cells is distal to the third layer of expandable stent cells. In some embodiments, the shape that is substantially diamond and flares outwardly in the radial direction flares out at the distal-facing legs. In some embodiments, the shape that is substantially diamond and flares outwardly in the radial direction flares out at a portion of the distal-facing legs. In some embodiments, each stent cell of the first layer of stent cells comprises a height along the longitudinal direction of about 5 mm to about 12 mm. In some embodiments, each stent cell of the second layer of stent cells comprises a height along the longitudinal direction of about 5 mm to about 18 mm. In some embodiments, each stent cell of the third layer of stent cells comprises a height along the longitudinal direction of about 25 mm to about 35 mm. In some embodiments, the stent frame comprises a maximum height along the longitudinal direction in the range of 18 mm to 25 mm. In some embodiments, the stent frame comprises a diameter of a cross section perpendicular to the longitudinal direction in the range of 20 mm to 40 mm when the stent frame is in the expanded deployed configuration as measured from an outer wall of the stent frame optionally at a distal end of the stent frame. In some embodiments, the stent frame comprises a thickness of about 0.2 mm to about 1.2 mm along a radial direction. In some embodiments, the stent frame comprises a layer of open ends proximal to the first layer of stent cells. In some embodiments, the stent frame comprises a layer of open ends distal to the third layer of stent cells. In some embodiments, one or more open ends of the layer forms at least part of a substantially triangular shape. In some embodiments, one or more open ends of the layer forms at least part of a substantially trapezoid shape. In some embodiments, one or more inflections of one or more stent cells of the plurality of stent cells comprise two stent struts directly attached together or integrally formed together. In some embodiments, one or more inflections of one or more stent cells of the plurality of stent cells comprise two stent struts directly attached together or integrally formed together thereby forming a U-shape. In some embodiments, the two stent struts remain attached when the stent frame is in the expanded deployed configuration or the collapsed delivery configuration. In some embodiments, the device assembly is configured to be delivered within a delivery catheter. In some embodiments, the device assembly is deployed via relative movement out of the delivery catheter. In some embodiments, the expandable sealing skirt is self-expandable when the device assembly is deployed. In some embodiments, the expandable sealing skirt is configured to self-expand against the vessel wall instantaneously, in about 0.001 second to about 1 minute after it is out of the delivery catheter. In some embodiments, the expandable sealing skirt comprises from a 2× to a 30×, a 3× to a 20×, a 5× to a 30×, a 10× to a 30×, a 2× to a 20×, at least 2×, at least 5×, at least 10×, 1.5× to 20×, 1.5× to 30×, at most 20×, at most 10×, or at most a 30× volumetric expansion from an collapsed state to an expanded state. In some embodiments, the protruding cells comprise from a 2× to a 30×, a 3× to a 20×, a 5× to a 30×, a 10× to a 30×, a 2× to a 20×, at least 2×, at least 5×, at least 10×, 1.5× to 20×, 1.5× to 30×, at most 20×, at most 10×, or at most a 30× volumetric expansion from an collapsed state to an expanded state. In some embodiments, the device assembly comprises sutures coupling the expandable sealing skirt to the stent frame. In some embodiments, the expandable sealing skirt is coupled by the sutures to the stent frame at one or more proximally-facing legs of protruding cells. In some embodiments, the expandable sealing skirt is coupled by the sutures to the stent frame at the distal legs of the first layer of the stent frame. In some embodiments, the expandable skirt is biocompatible and biostable when the device assembly is implanted in the human patient. In some embodiments, the expandable skirt is attached to a top, middle, or bottom portion of the stent frame. In some embodiments, the expandable skirt is compressible instantaneously within a time period of about 0.001 second to about 1 minute. In some embodiments, the non-protruding region is configured to provide a backing for the protruding region thereby preventing the protruding region from bulging inward along the radial direction. In some embodiments, the non-protruding region is permanently integrated with the protruding region. In some embodiments, the non-protruding region is at least partly located within the stent frame when coupled to the stent frame. In some embodiments, a maximal protruding thickness of the protruding region along the radial direction is in the range of about 3 mm to about 1 cm or 3 mm to 1 cm.

Provided herein is a method of endovascular prosthesis implantation with an expandable skirt in a human patient using the device assembly herein, the method comprising: delivering the device assembly within a delivery catheter in the collapsed delivery configuration to a preselected location within the human patient, deploying the device assembly by: relative movement of the delivery catheter with respect to the device assembly thereby allowing the stent frame and the expandable skirt to self-expand or expand in a controlled manner against a vessel wall. The method in some embodiments comprises recapturing the device assembly within the delivery catheter by relative movement of the delivery catheter with respect to the device assembly thereby allowing the expandable skirt to compress within the delivery catheter. The method in some embodiments comprises retrieving the delivery catheter from the patient, the delivery catheter enclosing the device assembly therewithin in a resheathed state. In some embodiments, the controlled expansion is via controlling a balloon catheter that the expandable skirt is loaded thereon.

Disclosed herein is a device assembly for transcatheter aortic valve implantation in a human patient, the device assembly comprising: a stent frame configured to provide a scaffold to the device assembly when properly deployed; a valve attached to the stent frame; optionally a pericardial tissue skirt attached to the stent frame; and an expandable sealing skirt attached to one or more of the stent frame, the valve, and the pericardial tissue skirt, the expandable sealing skirt comprising a three-dimensional geometrical shape comprising: a protruding region protruding outwardly along an radial direction against a vessel wall. In some embodiments, expandable sealing skirt further comprises a non-protruding region. In some embodiments, the protruding level is spatially variable at least along a longitudinal direction of the stent frame, when properly deployed. In some embodiments, the protruding region comprises a plurality of protruding cells. In some embodiments, the plurality of cells are arranged to conform to an arrangement of a plurality of cells of the stent frame. In some embodiments, the plurality of cells is shaped to fit into a plurality of cells of the stent frame. In some embodiments, the arrangement of the plurality of cells comprises a pattern selected from: a fully circumferential, a partially circumferential, a staggered, a triangular, a square, an oval, a partial oval, a rhomboidal shape, and a random and closed configuration. In some embodiments, each of the plurality of cells comprises a three-dimensional shape selected from: a conical, a reverse conical, a cylindrical, a hemispherical and a spherical shape. In some embodiments, the protruding region comprises a circumferential spiral ring. In some embodiments, the device assembly is configured to be delivered within a delivery catheter. In some embodiments, the device assembly is deployed via relative movement out of the delivery catheter. In some embodiments, the expandable sealing skirt is self-expandable when the device assembly is deployed. In some embodiments, the expandable skirt is configured to self-expand against the vessel wall within a few seconds, for example, in about 0.001 second to about 1 minute after it is out of the delivery catheter. In some embodiments, the expansion of the skirt is perceptively instantaneous. That is, the expansion happens so quickly that it is effectively instantaneous within the ranges or timing disclosed herein. Thus, expansion of the skirt occurs within the timing disclosed herein. In some embodiments, the expandable skirt is configured to allow up to 30× volumetric expansion from an undeployed (or compressed) state to a deployed state. In some embodiments, the three-dimensional shape is selected from: a conical, a reverse conical, a cylindrical, and a spherical shape. In some embodiments, the expandable skirt is attached to one or more of the stent frame, the valve, and the pericardial tissue skirt via a conventional suturing method with conventional suture material. In some embodiments, the expandable skirt is biocompatible and biostable when the device assembly is implanted in the human patient. In some embodiments, the expandable skirt comprises foam. In some embodiments, the expandable skirt is attached to a top, middle, or bottom portion of the stent frame. In some embodiments, the expandable skirt is compressible within a time period of about 0.001 second to about 10 seconds, for example, as less as about 0.1 second. In some embodiments, the compression of the skirt is perceptively instantaneous. That is, the compression happens so quickly that it is effectively instantaneous in the ranges or timing disclosed herein. Thus, compression of the skirt occurs within the timing disclosed herein.

Disclosed herein is an expandable sealing skirt for use with a transcatheter aortic valve implantation device for a human patient, the expandable sealing skirt comprising: a three-dimensional geometrical shape comprising: a non-protruding region; and a protruding region protruding outwardly along an radial direction against a vessel wall; and an attachment element configured to attach the expandable skirt to one or more of a stent frame, a valve, and a pericardial tissue skirt. In some embodiments, expandable sealing skirt further comprises a non-protruding region. In some embodiments, the protruding level is spatially variable at least along a longitudinal direction of the stent frame, when properly deployed. In some embodiments, the protruding region comprises a plurality of protruding cells. In some embodiments, the plurality of cells are arranged to conform to an arrangement of a plurality of cells of the stent frame. In some embodiments, the plurality of cells is shaped to fit into a plurality of cells of the stent frame. In some embodiments, each of the plurality of cells comprises a shape selected from: a fully circumferential, a partially circumferential, a staggered, a triangular, a square, an oval, a partial oval, a rhomboidal shape, and a random and closed configuration. In some embodiments, the skirt is configured to be delivered with the stent frame, the valve, and the pericardial tissue skirt within a delivery catheter. In some embodiments, the skirt is deployed via relative movement out of the delivery catheter. In some embodiments, the skirt is self-expandable when the skirt is properly deployed. In some embodiments, the expandable skirt is configured to allow 30× volumetric expansion from an undeployed state to a deployed state. In some embodiments, the expandable skirt is configured to expand against the vessel wall instantaneously within a few seconds, for example, in about 0.001 second to about 1 minute after it is out of the delivery catheter. In some embodiments, the expansion of the skirt is perceptively instantaneous. That is, the expansion happens so quickly that it is effectively instantaneous within the ranges or timing disclosed herein. Thus, expansion of the skirt occurs within the timing disclosed herein. In some embodiments, the expandable skirt comprises foam. In some embodiments, the three-dimensional shape is selected from: a conical, a reverse conical, a cylindrical, and a spherical shape. In some embodiments, each of the plurality of cells comprises a three-dimensional shape selected optionally from: a conical, a reverse conical, a cylindrical, a hemispherical and a spherical shape. In some embodiments, the attachment element is configured to be sutured to one or more of the stent frame, the valve, and the pericardial tissue skirt via a conventional suturing method with conventional suture material. In some embodiments, the expandable skirt is biocompatible and biostable when the device assembly is implanted in the human patient. In some embodiments, the expandable skirt is attached to a top, middle, or bottom portion of the stent frame. In some embodiments, the expandable skirt is compressible instantaneously within a time period of about 0.001 second to about 10 seconds, for example, as less as about 0.1 second. In some embodiments, the compression of the skirt is perceptively instantaneous. That is, the compression happens so quickly that it is effectively instantaneous in the ranges or timing disclosed herein. Thus, compression of the skirt occurs within the timing disclosed herein.

Disclosed herein is a method of transcatheter valve implantation with an expandable skirt in a human patient, the method comprising: delivering a device assembly within a delivery catheter in a un-deployed state to a preselected location within the human patient, wherein the device assembly comprising a stent frame, a valve attached thereto, optionally a pericardial tissue skirt or a PET/Dacron skirt, and an expandable skirt attached to one or more of the stent frame, valve, and pericardial skirt, and wherein the expandable skirt comprises a three-dimensional geometrical shape comprising: a protruding region protruding outwardly at least along an radial direction against a vessel wall; and an attachment element configured to attach the expandable skirt to one or more of a stent frame, a valve, and a pericardial tissue skirt; and deploying the device assembly by relative movement of the delivery catheter with respect to the device assembly thereby allowing the expandable skirt to self-expand against a vessel wall or allowing the expandable skirt to expand in a controlled manner against a vessel wall. In some embodiments, the method herein further comprises recapturing the device assembly within the delivery catheter by relative movement of the delivery catheter with respect to the device assembly thereby allowing the expandable skirt to compress within the delivery catheter. In some embodiments, the method herein further comprises retrieving the delivery catheter from the patient, the delivery catheter enclosing the device assembly therewithin in a resheathed state.

In some embodiments, advantages of the disclosed device assemblies include but are not limited to: the expandable sealing skirt of the described device assemblies can replace the conventional pericardial tissue or Polyethylene Terephthalate (PET) skirt without altering any other component of the valve (stent frame, leaflet design and manufacturing/assembly thereof) and thereby not affecting the clinically proven durability and hemodynamics of the valve. This can allow for preserving practically all clinically relevant and proven features, including visualization, device placement techniques, etc. while dramatically improving the sealing performance of the devices and potentially extending the use of the devices in patients with heavy calcification and in patients with bicuspid valves. In some embodiments, the materials and the design of the device assemblies and methods herein enable up to 3000% and no smaller than 1000% volumetric expansion capability that allows for crimping in a low profile catheter within 18F profile (e.g., outer diameter) or lower and seal highly calcified annulus at the same time. Thus, in some embodiments, the device assemblies and methods herein using an expandable technology does not increase device profile. In comparison to the current latest version of the skirt of the COREVALVE®, the described technology may offer an about 2000% increase in outward expansion. In comparison to the SAPIEN® and SAPIEN® XT skirt, the device assemblies disclosed herein can enable active sealing with no compressible or expandable characteristics. In some embodiments, the rapid expansion characteristics of the device assemblies and methods herein allow complete sealing by completion of implantation procedure. In some embodiments, the expandable sealing skirts herein can expand to their approximate full volume in no greater than 15-20 minutes after being deployed from the catheter. In some embodiments, the compression of the skirts is perceptively instantaneous. That is, the compression happens so quickly that it is effectively instantaneous in the ranges or timing disclosed herein. Thus, compression of the skirts occurs within the timing disclosed herein. Such compression characteristics may allow for complete recapturability of device multiple times in situ. The skirts herein can expand fully after multiple recapturing and enable full sealing in no greater than 15-20 minutes of recapturing in situ. In some embodiments, the skirt is biocompatible, biostable and fully compatible with chemical sterilization storage solution, up to 2% glutaraldehyde. In some embodiments, the device assemblies and methods herein are also compatible with ethylene oxide and radiation sterilization methods. In some embodiments, the skirt is compatible with delivery systems used for both balloon-expanding and self-expanding valves. For delivery systems for self-expanding valves, the sheathing/re-sheathing procedures can occur both in the direction towards the ventricle or away from it (i.e. the movement of the delivery sheath during deployment can occur in either direction, towards or away from the ventricle). In some embodiments, the compression force of skirt is much lesser than the radial force of stent, thus allowing preferential expansion of the skirts in the gaps causing paravalvular leaks and does not have an adverse effect on the effective orifice area (EOA) of the device.

In some embodiments, benefits that may be obtained by the users of device assemblies herein include but are not limited to: elimination of paravalvular leaks which results in lower mortality and morbidity rates; possible extension of TAVI devices to treatment of patients with bicuspid valve aortic stenosis; reduction of need for excessive oversizing of the devices that may lead to problems with the conduction system of the heart causing arrhythmias; reduction in the need for post-dilatation of the valves with balloons that carries a significant risk of stroke and therefore mortality. Additional high-level benefits can include: the users/physicians may not have to undergo any significant re-training on the devices as the implantation procedures and delivery systems remain unchanged as the existing art; the manufacturing procedures for the valve may not have any significant changes as conventional methods and materials are used for that purpose; potential to reduce the device profile which allows for treatment of a larger set of patient with smaller access vessels while providing best-in-class sealing performance.

Existing skirts used in endovascular prostheses such as TAVI devices suffer from various degree of paravalvular regurgitation after implantation especially in patients with highly calcified annulus.

Provided herein are improved device assemblies, systems, and methods of sealing of the annulus, especially those with high calcification levels after TAVI procedure. Provided herein are expandable sealing skirts and device assemblies comprising expandable sealing skirts compatible for usage with various devices for TAVI. In some embodiments, the expandable sealing skirts and/or device assemblies comprising expandable sealing skirts are designed to replace or use in combination with the pericardial tissue skirt without altering any other component of the valve or the other elements of the TAVI devices (e.g., stent frame, leaflet design and manufacturing/assembly thereof). In some embodiments, the expandable sealing skirts herein advantageously allows up to 30× volumetric expansion capability (expanded vs. compressed state) and enable crimping conventional valve sizes (e.g. 20, 23, 26, up to 30 mm) within 18F (or lower) profile and effective sealing of highly calcified annulus. In some embodiments, such high volumetric expansion capability allows for outward extension of the expandable sealing skirts (the described protruding region) by up to approximately 5 mm radially outward from the stent frame thereby providing enhanced sealing in highly calcified annuli, where the paravalvular leak sites are large. In some embodiments, the expandable skirts herein advantageously allow rapid expansion thereby significantly improved sealing of calcified annulus by completion of TAVI implantation procedure or other similar surgical procedures when compared with traditional tissue skirt with TAVI devices. Another advantage of the expandable skirts disclosed herein includes instantaneous compression characteristics that allow complete recapturability of the device. Additional advantage of the expandable skirts herein includes proven biocompatibility and biostability, and compatibility with sterilization/storage solution. Other advantages of the expandable skirts disclosed herein includes that it requires: no change to the valve design, including leaflet design, leaflet suturing method/procedure, attachment procedure/method of the valve to the stent frame; no change to the stent frame; no change to the loading procedures of the valve within the delivery catheter; no change to delivery of the valve and/or stent frame technique/procedure within the patient, conventional manufacturing techniques (standard suturing methods and materials) for assembling expandable skirts onto stent frame. In some embodiments, the expandable skirts herein also are advantageously capable of "bolting-on" to existing TAVI devices. In some embodiments, the expandable sealing skirts herein also allow controlled activation during deployment, require no increase in device profile i.e. can be adapted to the existing device profile, retains all features for long-term performance and accurate delivery of the TAVI devices, and demand no added time or steps to the TAVI device implantation procedure.

Skirts

In some embodiments, disclosed herein are expandable sealing skirts for use with endovascular prostheses such as TAVI devices. As used herein, the term "expandable sealing skirt" is synonymous with an expanded sealing skirt or deployed sealing skirt, skirt, or sealing skirt, and refers to skirt having the protruding region described throughout the specification herein in various and multiple described embodiments. Such expandable sealing skirt has a closed or collapsed configuration for delivery of the sealing skirt to the deployment site within a sheath, a catheter or any other device of similar function, and an expanded or deployed configuration where the protruding region extends radially beyond the outer radial wall of the stent frame adjacent to it. Foams as described herein are used to form the protruding cells of the protruding region, which themselves are collapsible and expandable and can even be reversibly collapsed from an expanded state. In some embodiments, the foams herein are pre-formed foams. In some embodiments, the foams herein are formed at the deployment site using foaming agent or liquid such as blood.

In some embodiments, the expandable sealing skirt is self-expandable once deployed. In some embodiments, the skirt is self-expandable once it is deployed out of the delivery catheter. In some embodiments, the sealing skirt is expanded to its expanded state once deployed.

In some embodiments, the sealing skirt does not deploy automatically once it is out of the catheter or sheath. In some embodiments, when the sealing skirt is out of the catheter or sheath, it still requires a mechanical activation for its deployment or expansion. In some embodiment, the mechanical activation includes removal of a restraining element of the sealing skirt. In some embodiments, the sealing skirt is not at its expanded state when it is deployed out of the delivery catheter or a device equivalent thereto as it is still compressed by an additional element that is part of the catheter or not part of catheter but can be housed within the catheter. For example, after the stealing skirt is moved out of the catheter or sheath, the sealing skirt may be compressed at its distal end by a restraining element. It can only be deployed to its expanded state after it the restraining element is removed from the distal end of the sealing skirt. In some embodiments, such controlled deployment mechanism is advantageous to ensure correct placement of the sealing skirt to the pre-determined location before it is expanded.

In some embodiments, the sealing skirts herein include a deployed state, or equivalently, an expanded state, an uncompressed state, or a delivered state. In some embodiments, the skirts herein include an undeployed state, or equivalently, a collapsed state, a compressed state, or sheathed state. In some embodiments, the sealing skirts herein include a resheathed state after expansion. In some embodiments, the sealing skirts herein are in a resheathed state for proper withdrawal from the patient, optionally with the delivery catheter. In some embodiments, the sealing skirts herein are compressed within a deliver catheter. In some embodiments, the sealing skirts herein are delivered to a pre-selected location within a human patient in a compressed state. In some embodiments, the sealing skirts herein are deployed at the pre-selected location with relative movement to the deliver catheter. In some embodiments, the sealing skirts herein are deployed at the pre-selected location with pressure using a balloon catheter.

In some embodiments, disclosed herein is a device assembly 100. In some embodiments, the device assembly includes one or more of: a stent frame 102, a valve 103, a native pericardial tissue skirt, an expandable skirt 101, and attachment element(s) 104 configured to be attached to one or more of the stent frame, the valve, and the pericardial tissue skirt, for example, by suturing via conventional suturing method with conventional suture material. In some embodiments, a skirt herein is sutured to the stent frame and/or the pericardial tissue skirt such that the attachment interface after suturing provides a hydrodynamic seal at the interface and the whole assembly in-turn provides a hydrodynamic seal at an annulus of a vessel wall.

In some embodiments, the device assembly comprises a stent frame, a valve, and an expandable skirt comprising a non-protruding region 101*a* and a protruding region 101*b*. In some embodiments, the protruding region and the non-protruding region overlap. In some embodiments, the at least a portion of the non-protruding region is proximal to a portion of the protruding region. In some embodiments, the protruding region includes connector regions 105*a* between protruding cells 105 of the protruding region. In some embodiments, the connector regions align with the shape of the stent frame, and are radially closer to the longitudinal axis of the stent frame at the adjacent aligned stent strut. The protruding region comprises at least one protruding foam cell 105, alternative and equivalently referred to herein as a foam cell or protruding cell made of a foam having a collapsed configuration (also called a resheathed configuration, a contracted configuration, at least) and a deployed configuration (also called a delivered configuration, an expanded configuration, at least). In some embodiments, the non-protruding region is also made from the foam described herein. In some embodiments the non-protruding region is attached to the foam of the protruding region chemically such as described in the examples provided herein, or mechanically (by suturing), or by another manner such as by using an adhesion material therebetween, or by heat adhesion.

Referring to FIGS. 1A-1E, FIGS. 1H-1J, FIGS. 1K-1M, FIGS. 1N-1P and/or FIGS. 1O-1W, in some embodiments, an expandable skirt 101 is shown in its deployed state or configuration. In some embodiments, the skirt is sutured at the attachment element 104 to the struts of the stent frame 102 and/or the artificial aortic valve 103 to be implanted or otherwise integrated to the stent frame and/or valve to be implanted into the patient. Referring to FIGS. 1E, 1J, 1M 1N-1P and/or 1O-1W, in some embodiments, the skirt 101 is sutured to the stent frame 102. In some embodiments, the suturing occurs at the top of the top layer of protruding foam cells 105. In some embodiments, the suturing occurs at the bottom of the bottom layer of protruding foam cells. In some embodiments, e.g., as shown in FIGS. 1B, 1I, 1L, and/or 1O, each protruding cell may be attached, (e.g., sutured) to the stent frame at least at part of its edges. As an example, the attachment may occur at two edges for the top layer of protruding cells and bottom layer of protruding cells for embodiments with at least two layers of protruding cells. In some embodiments, the suturing occurs at least in part at the connecting regions 105*a*. In some embodiments, the valve is also sutured 106 or otherwise integrated to the stent frame. In some embodiments, suturing or integration of the skirt is kept away from the "scallop" of the tissue and/or valve/valve leaflet for at least a predetermined distance so that does not interfere with the "scallop" of the tissue, valve/valve leaflet or affect their normal functionalities. In some embodiments, a skirt having diamond shaped foam cells, triangular shaped foam cells, chevron shaped foam cells, substantially chevron shaped foam cells, concave hexagonal shaped foam cells, partial hexagonal shaped foam cells, or hexagonal shaped foam cells conforming to at least a portion of the stent cells 102*a* of the stent frame is designed so that the attachment element 104 is secured using conventional sutures to the stent frame, or to at least one of edges, legs, arms, or struts of the cells 102*a* and/or to the native tissue skirt. In some embodiments, the suturing occurs prior to loading the stent frame in the delivery catheter. In some embodiments, the suturing occurs prior to loading the stent frame in the delivery catheter. In some embodiments, the skirt is connected or coupled to the stent prior to the stent frame and skirt being loaded into a delivery catheter. In some embodiments, the skirt is deployed into the stent frame following delivery of the stent frame in situ. In some embodiments, suturing of the skirt occurs following delivery of the stent frame to its target location. In some embodiments, all edges of the skirt cells can be secured using sutures or other equivalent attachment or fixation methods to the stent frame and/or native skirt. In some embodiment, the native tissue skirt is optionally not present in the device assembly disclosed herein. In some embodiments, at least one, two, three, or four, edges of the skirt cells are secured to the stent, valve, and/or native skirt.

As used herein, with respect to the expandable stent cells in the columnar region or conical region of the stent frame, at least, and/or the protruding cells, a "diamond" shape is synonymous with "substantially diamond" or "generally diamond" and refers to a shape having four legs (or alternatively called struts, or alternatively called arms, or alternatively called edges) and four inflections or vertices. In some embodiments, the diamond shape includes two sets of parallel legs, or two sets, wherein the shape may actually be kite shaped having a first set of adjacent, equally length legs connected by an inflection therebetween, and formed in a layer of repeating diamond shapes into a column around the stent frame's longitudinal axis to form the stent frame in its columnar region and a second set adjacent, equal length legs with a second inflection therebetween, wherein the first and second sets are connected by two additional inflections. The "diamond" shape, in some embodiments, does not have four sides that are equal in length. In some embodiments, the "diamond" shape has four sides are equal in length. In some embodiments, the "diamond" shape of the expandable stent cell forms a parallelogram or is a rhombus, or both. In some embodiments the diamond shape includes four legs and is convex kite-shaped, wherein any one of the following conditions is true: two disjoint pairs of adjacent sides are equal; and one diagonal is the perpendicular bisector of equal length, which are formed in the other diagonal. In some embodiments, the connecting legs extend from one inflection to the next inflection in a general direction that is parallel to its opposite parallel leg, but is curved rather than straight—when laid flat in the expanded deployed configuration. Thus, the shape formed by the four legs is referred to as substantially diamond shape or diamond shape herein. Substantially diamond shape or diamond shape may also refer to true diamond shapes having straight edges and two pairs of parallel edges or legs and within each pair there the edges or legs are parallel. The height of the stent cells from the proximal-most inflection to the distal-most inflection decreases gradually from the top portion (proximal) to the bottom portion (distal) of the stent frame.

As used herein, with respect to the expandable stent cells and/or the protruding cells, a "rectangular" shape is synonymous with "substantially rectangular" or "generally rectangular" and refers to a shape having four legs (or alternatively called struts, or alternatively called arms) and four inflections. The "rectangular" shape, in some embodiments, does not have four legs that are equal in length. In some embodiments, the "diamond" shape has two pair of legs and each pair of legs is equal in length. In some embodiments, a rectangular shape (or synonymously, a substantially rectangular shape) includes four legs (in two parallel pairs) that have inflections therebetween. In some embodiments, the connecting legs extend from one inflection to the next inflection in a general direction that is parallel to its parallel pair, but is curved rather than straight—when laid flat in the expanded deployed configuration, thus the shape formed by the four legs are referred to as substantially rectangular shape or rectangular shape herein. In some embodiments, the connecting legs extend from one inflection to the next inflection in a general direction that is parallel to its parallel pair, but the inflection connecting two legs can be curved so that it is not a right angle of 90 degrees when laid flat in the expanded deployed configuration, thus the shape formed by the four legs are referred to as substantially rectangular shape or rectangular shape herein. Substantially rectangular shape or rectangular shape may also refer to true rectangular shapes having straight edges and two pairs of edges or legs and within each pair there the edges or legs are parallel and the inflections are right angles of 90 degrees.

As used herein, with respect to the expandable stent cells and/or the protruding cells of the skirt, a "triangular" shape is synonymous with "substantially triangular" or "generally triangular" and refers to a shape having three legs (or alternatively called struts, or alternatively called arms) and three inflections, The "triangular" shape, in some embodiments, does not have three legs that are equal in length. In some embodiments, the "triangular" shape has three legs are equal in length. In some embodiments, a triangular shape (or synonymously, a substantially triangular shape) includes three legs that have inflections therebetween, with two of them being equal in length and identical in shape. In some embodiments, at least one, two or three legs are curved rather than straight—when laid flat in the expanded deployed configuration, thus the shape formed by the three legs are referred to as substantially triangular shape or triangular shape herein. Substantially triangular shape or triangular shape may also refer to true triangular shapes having straight edges.

In some embodiments, a skirt 101 herein includes a non-protruding region 101*a* and a protruding region 101*b*, e.g., as shown in FIGS. 1E, 1J, 1M, 1P-1R, and/or 1U. In some embodiments, the non-protruding region is at least partly within the stent frame, which means at least a portion of the non-protruding region is axially closer to the longitudinal axis of the stent frame (at the center of the annulus lumen) than the stent frame itself is. In some embodiments, the non-protruding region is sized to be collapsed within or substantially within the stent frame when the device assembly and the stent frame are in their collapsed delivery configuration, and abuts an interior surface of the stent frame and struts thereof when the device assembly and the stent frame are in their expanded deployed configuration. In some embodiments, the non-protruding region includes a foam mesh. In some embodiments, the foam mesh is a Polyethylene mesh or a Polyethylene Terephthalate (PET) mesh. In some embodiments, the non-protruding region is not expandable. In some embodiments, the non-protruding region is relatively flat along the circumference of the stent in the x-y plane.

In some embodiments, the non-protruding region 101*b* is integrated to the protruding regions via attachment means. In some embodiments, such attachment means provides enough support so that the integrated non-protruding regions and protruding regions do not fall apart during and after deployment, and during or after resheathing. In some embodiments, the attachment means may include gluing or any other methods that enable stable attachment, such as heat bond, glue, chemical bond, suturing, or co-formation, as noted in embodiment examples below. In some embodiments, the non-protruding region and/or the connection region prevent the protruding cells from pushing inward along at least the radial direction, away from the annulus wall, and/or toward the center of the annulus lumen. In some embodiments, the non-protruding region and/or the connection region and/or the connecting cells is made of at least one different material from the protruding cells so that such areas (connection region and protruding cells, and/or non-protruding region and protruding region and/or connecting cells and protruding cells) include different physical properties. Nevertheless, the non-protruding region and protruding region is configured to form a single body by the integration. In some embodiments, both regions are made of bio-compatible and bio-stable material(s). In some embodiments, the expandable skirt after 28 days in mice shows non-significant difference in tensile stress when compared to with traditional tissue skirt. In a particular embodiment, after subcutaneous implantation into mice, the expandable skirt enables cell infiltration and shows no sign of overt inflammation such in vivo toleration in long term study demonstrates the expandable skirt to be bio-stable and biocompatible. In some embodiments, all the protruding cells are integrated with the non-protruding region. In some embodiments, at least some of the protruding cells are integrated with the non-protruding region. Such protruding cells are distributed along the entire circumference of the annulus wall. In some embodiments, the non-protruding region extends longer in the longitudinal or z direction than the non-protruding region. In some embodiments, the non-protruding region extends longer than the non-protruding region toward the middle or top portion of the stent frame as in FIGS. 1E, 1J, 1M, 1P, 1U and/or 4O. In some embodiments, the non-protruding region extends longer than the protruding region toward the bottom portion of the stent frame, e.g., FIGS. 1Q-1R.

In some embodiments, the non-protruding region and the protruding region are relatively flat on the inside (the side facing the annulus lumen). In some embodiments, the skirt does not bulge inside after or during deployment to advantageously minimize extra mass in the skirt and/or minimize excessive profile of the skirt so that it can fit into a delivery catheter with a profile or mass limit. In some embodiments, the skirt remains flat and not bulging inside so that it does not impede blood flow within the annulus.

In some embodiments, the protruding region 101*b* comprises one or more protruding cells 105 comprising a shape appropriate for the stent design with which it is used. In some embodiments, the shape of the protruding cell(s) is pre-formed. In some embodiments, the protruding cells are casted into specific shapes so that mass of the skirt is used in regions that are needed. As nonlimiting examples, the protruding cells may be molded or 3D printed and then integrated with a flat backing. In some embodiments, the flat back when properly attached to a stent frame remains at least partly within the stent frame. In some embodiments, the flat back includes the non-protruding region. In some embodiments, the flat back includes the connection region. In some embodiments, the flat backing is integrated with the protruding region. In some embodiments, the flat back includes the connecting cells. In some embodiments, the flat backing is integrated with the protruding cells. In some embodiments, part of the skirt is configured to fit within a stent frame and the protruding cell 105 is configured to protrude from one or more cells of the stent frame of the stent frame away from the annulus cavity, along a radial direction 107, or toward the annulus wall. In some embodiments, each protruding cell of the skirt herein comprises a shape that enable its protrusion through a single cell of the stent frame outwardly along the radial direction when the skirt is deployed. In some embodiments, each protruding cell of the skirt may comprise a shape that enable its protrusion through two, three, four, five, or even more cells of the stent frame.

In some embodiments, the skirt has a three-dimensional shape that is selected from but not limited to: a conical, a reverse conical, a cylindrical, and a spherical shape. In some embodiments, the one or more protruding cells are arranged at least partly on the outside of the skirt so that the arrangement of the protruding cells includes a three dimensional shape which conforms to the shape of the skirt or differs from the shape of the skirt. In some embodiments, the three dimensional shape for arrangement of the protruding cells can be any geometrical shape, optionally closed or open. In some embodiments, the protruding cells are arranged along full circumference of the stent frame in the x-y plane and partially along the z-direction or longitudinal direction. In some embodiments, the protruding cells are arranged so that the protruding cells block blood flow in the z or longitudinal direction at or near the entire circumference of the stent frame. In other words, blood at or near the circumference of the stent frame or the annulus wall flowing in a longitudinal direction can be blocked by one or more protruding cells at different location along the longitudinal direction. In some embodiments, the protruding cells are arranged so that the protruding cells blocks blood in the z or longitudinal direction at or near almost entire circumference of the stent frame, only some stent struts may allow very limited blood flow along the z or longitudinal direction. In some embodiments, the protruding cells 105 are of a single layer arranged substantially evenly around the circumference of the circular, as shown FIGS. 1M-1N, and 1V, and FIGS. 4M-4P. In some embodiments, protruding cells 105 conform to the staggered pattern of stent cells, occupying at least a portion of each corresponding stent cell. In some embodiments, the two protruding cells of a single layer are separated by a distance that increases gradually along the longitudinal direction. In some embodiments, when only a single layer of protruding cells may not cover the entire circumference of the stent when viewed along a longitudinal direction. In some embodiments, the struts 113 of the stent frame may not be able to prevent blood leakage therefrom. Such level of leakage may not be clinically significant for certain patient. In FIGS. 1A-1E, FIGS. 1H-1J, FIGS. 1K-1M, FIG. 1P and/or in FIGS. 1Q, 1R, and 1W for non-limiting example, wherein two layers of protruding cells are stacked together along the z-direction, at least one protruding cells is placed adjacent to the struts 113 so that block leakage is effectively prevented. In some embodiments, the protruding cells 105 are arranged in a staggered shape while conforming to the staggered pattern of the stent cells, occupying at least a portion of each corresponding stent cell so that the protruding cells blocks blood flow in the z or longitudinal direction at or near almost entire circumference (e.g. at least 99.5%, 99%, 98%, 97%, 96%, 95%, 95%, 93%, 92%, 91%, 90%, etc.) of the stent frame, as shown in FIGS. 1P, 1Q-1R, 1U, 1W 4A, 4E, 4I, 5A, 5M, and/or 6A. In other words, the blood flow at or near the circumference of the stent frame (blood flow between the inner vessel wall and the protruding cells) can be blocked by one or more protruding cells. Thus, the protruding cells effectively seal the gap between the stent frame and the inner vessel wall and prevent blood leakage.

More layers of protruding cells 105 can be stacked along the z-direction to further improve sealing thus prevent leakage. To further support sealing, the stent frame may be further extended at its bottom, **102*b* as in FIG. 3A and/or FIGS. 3M-3P, at least, to include a protruding cell that conforms to the shape of the open-ended structures at the distal end of stent frame. Such additional protruding cells (e.g., FIGS. 1U, 1W) may be attached to the stent frame at one, two, three, or even more edges. In some embodiments, the protruding cells are arranged at least partial along circumference of the stent frame and at least partially along the z-direction or longitudinal direction. In some embodiments, the arrangement of the protruding cells includes a staggered arrangement. In some embodiments, one or more layers of protruding cells may include protruding cells with a bottom surface (the portion closest to the stent frame) that is substantially a triangle (e.g., FIGS. 1H, 1I, 1N-1O, 1Q-1R, and 1U), a square, an oval, a partial oval, a rhomboid, a random shape, a diamond (e.g., FIGS. 1B, 1E, and 1W), a partial diamond (e.g., FIGS. 1H, 1I, 1P, and 1U-1W), hexagonal, partially hexagonal, chevron, a pentagon, a hexagon, or a sloped shape comprising a narrower part toward a top end of skirt along the z-direction or longitudinal direction, and comprising a wider portion toward a bottom end of the skirt (e.g., FIGS. 1N-1R, and 1U, 1W), optionally if the stent frame were to be cut along the longitudinal direction and laid flat in two-dimensional plane. In some embodiments, the arrangement of the protruding cells includes a staggered shape. In some embodiments, each protruding cells may include a bottom surface (the surface closest to the stent frame) that is a triangle, a square, an oval, a partial oval, a rhomboid, a random shape, a diamond, a partial diamond, a pentagon, a hexagon, or a sloped shape comprising a narrower part toward a top end of skirt along the z-direction or longitudinal direction, and comprising a wider portion toward a bottom end of the skirt, optionally when the arrangement of the cells are projected onto a two dimensional plane. In some embodiments, each protruding cell may include a bottom surface (the surface closest to the stent frame) that is substantially triangle, substantially a portion of a substantial triangle, or substantially a trapezoid. In some embodiments, the protruding cells are shaped and sized to protrude from one or more cells of the stent frame radially away from the center of the annulus and toward the annulus wall. In some embodiments, the protruding cells are shaped and sized to align with one or more cells of the stent frame toward the annulus wall and protrude from one or more cells of the stent frame toward the annulus wall. In some embodiments, the shape of the protruding cells and/or arrangements of the cells are configured to provide low profile and/or low packing density leading to low profile of the TAVI device i.e. the arrangement/distribution of the protruding cells can be customized in order to achieve the minimum packing density leading to low/minimum profile. In some embodiments, the cell may be in configurations so that each individual cell can fit in the individual cells 102*a* of the stent frame. In some embodiments, each individual protruding cell includes a shape so that the bottom of the protruding cell (closest surface to the center of the stent frame along a radial direction) is similar to that of the cells of the stent frame. For example, as in FIGS. 1B, 1J, the protruding cells 105 have a bottom surface that is a diamond or is substantially a diamond. As another example, as in FIGS. 1I, 1M, 1K, 1N, 1Q, and 1W, the protruding cells 105 have a bottom surface that is a triangle or is substantially a triangle. As another example, as in FIG. 1L, the protruding cells 105** have a bottom surface that is a pentagon or is substantially a pentagon.

The protruding region may be trimmed after being formed, or during attachment to the stent frame, or not. In some embodiments, the protruding region is trimmed distal to the protruding cells, so as not to extend beyond the distal-most portions of the stent frame. In some embodiments, the protruding region is formed to sit below (i.e. distal to) the stent frame. In some embodiments, protruding cells are formed which are below (i.e. distal to) the stent frame. In some embodiments, the protruding cells that are below (i.e. distal to) the stent frame are not enclosed by or surrounded by any expandable stent cell. The protruding region is then attached to the stent frame of the device assembly such that the protruding cells are aligned with the expandable stent cells of the one or more layers of the stent frame and protrude therethrough when the device assembly is in its expanded deployed configuration. The attachments are described herein, such as by suturing with sutures.

In some embodiments, each protruding cell includes a protruding profile along the z or longitudinal direction when deployed freely without pressing the annulus wall. Such protruding profile along the z or longitudinal direction advantageously enable effective sealing for blood leakage in the z direction and facilitate efficient and easy loading and/or resheathing into catheter(s). Referring to FIGS. 1Q-1R, in particular embodiments, when cutting along a radial direction, the protruding profile 114 of the individual cells along a longitudinal direction may be a geometrical shape with a flat edge, for example, a rectangular shape, a substantially rectangular shape with zero, one, or more curved corners or inflections as shown in FIG. 1F. Referring to FIG. 1F, in some embodiments, when cutting along A-A' of FIG. 1E, 1J, 1M, or 1P the profile 114 of the individual cells along the longitudinal direction is shown. In this particular embodiment, the protruding profile includes a slope in the catheter loading direction (catheter moves relative to the stent and skirt in the loading direction) to prevent breakage of the expanded cells and facilitate loading/resheathing of the protruding cells. In this embodiment, the skirt can be properly deployed again after resheathing into the catheter. In some embodiments, the profile 114 may include a slope with an angle B which is about 1 degree to about 89 degrees. In some embodiments, the angle B is about 0.1 degree to about 75 degrees. In some embodiments, the angle B is in the range of 1 degree to 75 degrees. In some embodiments, the profile includes a maximal thickness along the radial direction when expanded. In some embodiments, the maximal thickness is in the range of about 1 mm to about 10 centimeters. In some embodiments, the maximal thickness is in the range of about 1 mm to about 3 centimeters. In some embodiments, the maximal thickness is in the range of about 3 mm to about 2 centimeters. In some embodiments, the maximal thickness is in the range of 1 mm to 10 centimeters. In some embodiments, the maximal thickness is in the range of 1 mm to 3 centimeters. In some embodiments, the maximal thickness is in the range Cof 3 mm to 2 centimeters. In some embodiments, the maximal thickness is about 3 mm, about 4 mm, about 5 mm, about 6 mm, about 7 mm, about 8 mm, about 9 mm, or about 1 cm. In some embodiments, the maximal thickness is 3 mm, 4 mm, 5 mm, 6 mm, 7 mm, 8 mm, 9 mm, or 1 cm. In some embodiments, the maximal thickness is about 11 mm, about 12 mm, about 13 mm, about 14 mm, about 15 mm, about 16 mm, about 17 mm, about 18 mm, about 19 mm, or about 2 cm. In some embodiments, the maximal thickness is 11 mm, 12 mm, 13 mm, 14 mm, 15 mm, 16 mm, 17 mm, 18 mm, 19 mm, or 2 cm. In some embodiments, the maximal thickness is about 21 mm, about 22 mm, about 23 mm, about 24 mm, about 25 mm, about 26 mm, about 27 mm, about 28 mm, about 29 mm, or about 3 cm. In some embodiments, the maximal thickness is 21 mm, 22 mm, 23 mm, 24 mm, 25 mm, 26 mm, 27 mm, 28 mm, 29 mm, or 3 cm.

In some embodiments, a protruding cell includes a maximal length along the longitudinal direction or z direction which is about the same as the length of the corresponding cell of the stent frame when expanded. In some embodiments, the maximal length is in the range of about 1 mm to about 10 centimeters. In some embodiments, the maximal length is in the range of about 1 mm to about 3 centimeters. In some embodiments, the maximal length is in the range of about 3 mm to about 2 centimeters. In some embodiments, the maximal length is in the range of 1 mm to 10 centimeters. In some embodiments, the maximal length is in the range of 1 mm to 3 centimeters. In some embodiments, the maximal length is in the range of 3 mm to 2 centimeters. In some embodiments, the maximal length is about 3 mm, about 4 mm, about 5 mm, about 6 mm, about 7 mm, about 8 mm, about 9 mm, or about 1 cm. In some embodiments, the maximal length is 3 mm, 4 mm, 5 mm, 6 mm, 7 mm, 8 mm, 9 mm, or 1 cm. In some embodiments, the maximal length is about 11 mm, about 12 mm, about 13 mm, about 14 mm, about 15 mm, about 16 mm, about 17 mm, about 18 mm, about 19 mm, or about 2 cm. In some embodiments, the maximal length is 11 mm, 12 mm, 13 mm, 14 mm, 15 mm, 16 mm, 17 mm, 18 mm, 19 mm, or 2 cm. In some embodiments, the maximal length is about 21 mm, about 22 mm, about 23 mm, about 24 mm, about 25 mm, about 26 mm, about 27 mm, about 28 mm, about 29 mm, or about 3 cm. In some embodiments, the maximal length is 21 mm, 22 mm, 23 mm, 24 mm, 25 mm, 26 mm, 27 mm, 28 mm, 29 mm, or 3 cm.

Figure 1E:
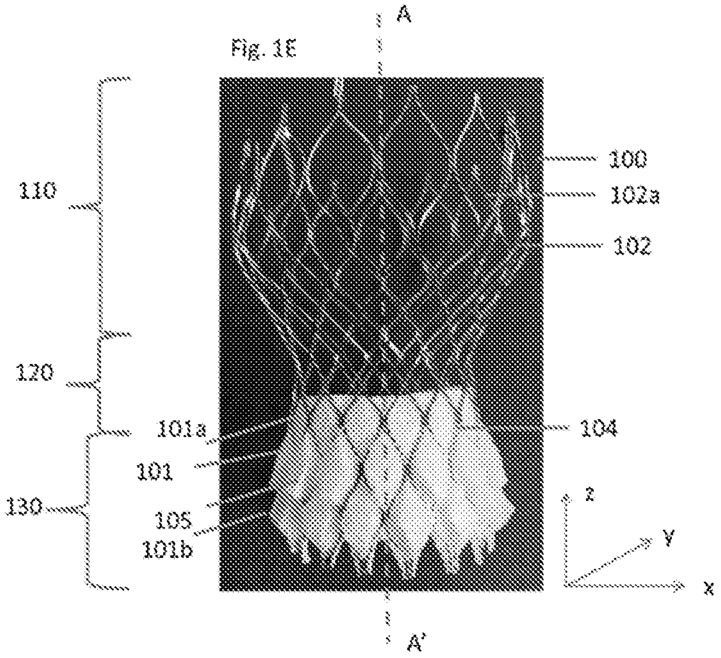
FIG. 1E shows a non-limiting exemplary embodiment of the expandable sealing skirt in a deployed state with a COREVALVE® stent frame.
Figure 1F:
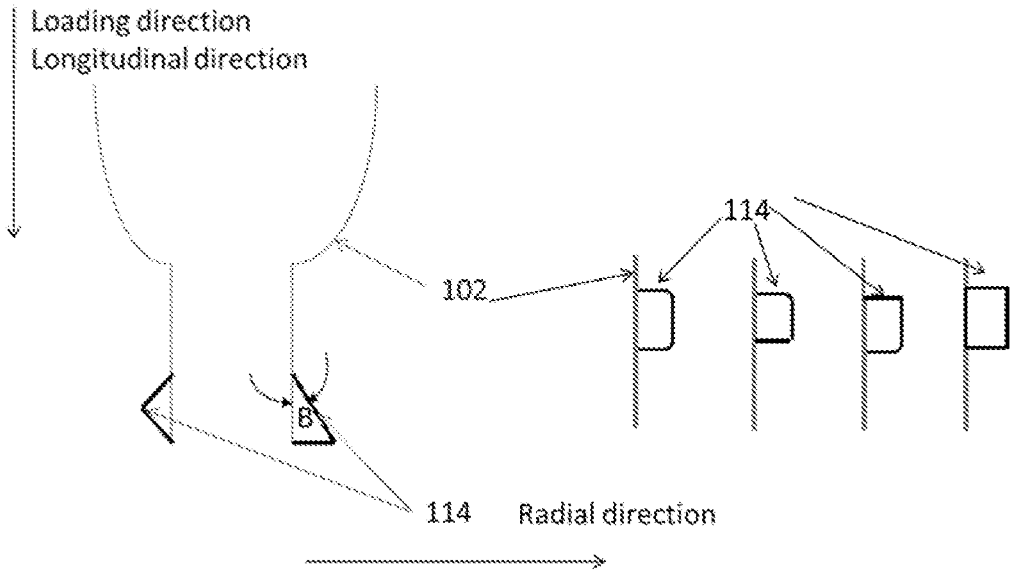
FIG. 1F shows a schematic with non-limiting exemplary embodiments of the profiles or cross-sections of the individual expandable cells or protrusions of the expandable sealing skirt in a deployed state in reference to the stent frame.
Figure 1G:
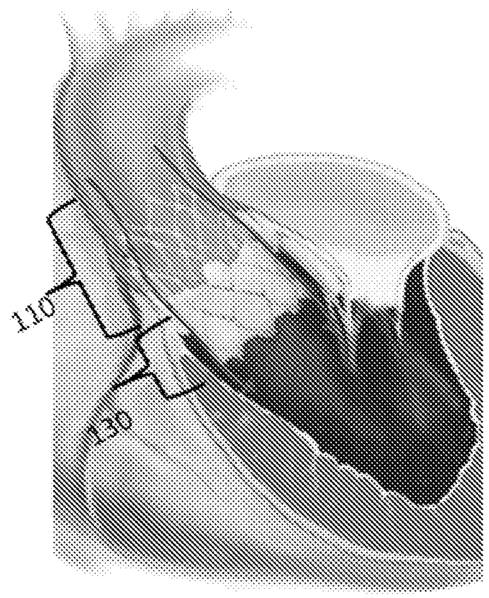
FIG. 1G shows a non-limiting exemplary embodiment of the expandable sealing skirt in a deployed state with a the stent frame in a patient's heart.
Figure 1H:
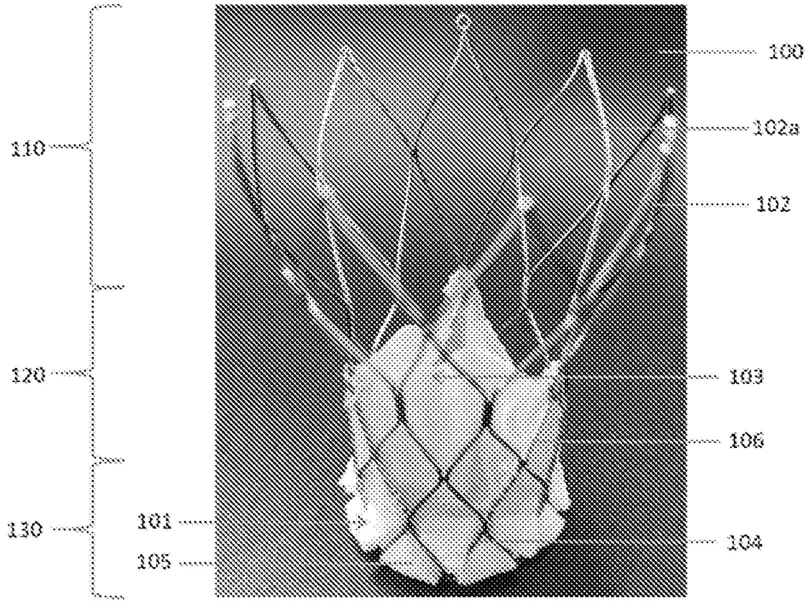
FIG. 1H-1I show non-limiting exemplary embodiments of the expandable sealing skirt in a deployed state (alternatively referred to herein as an expanded sealing skirt or deployed sealing skirt, or sealing skirt) with a PORTICO® stent frame and valve.
Figure 1I:
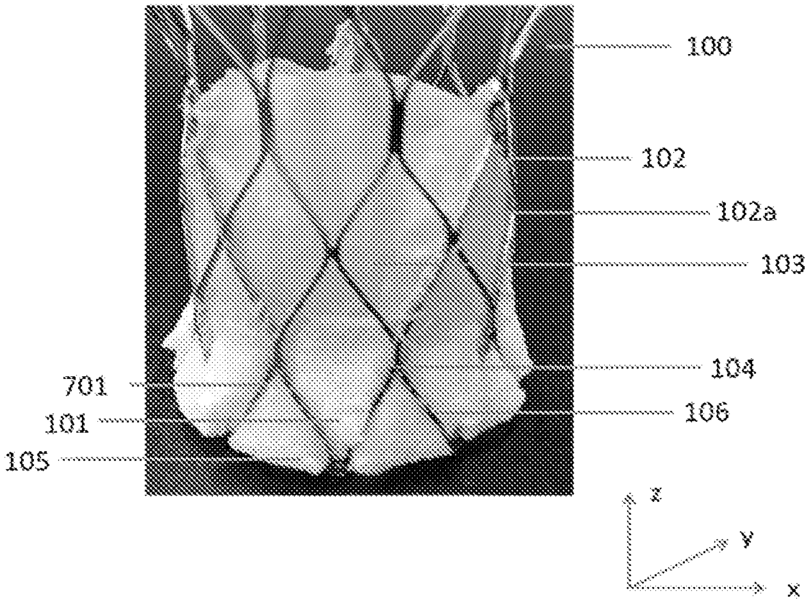
Figure 1J:
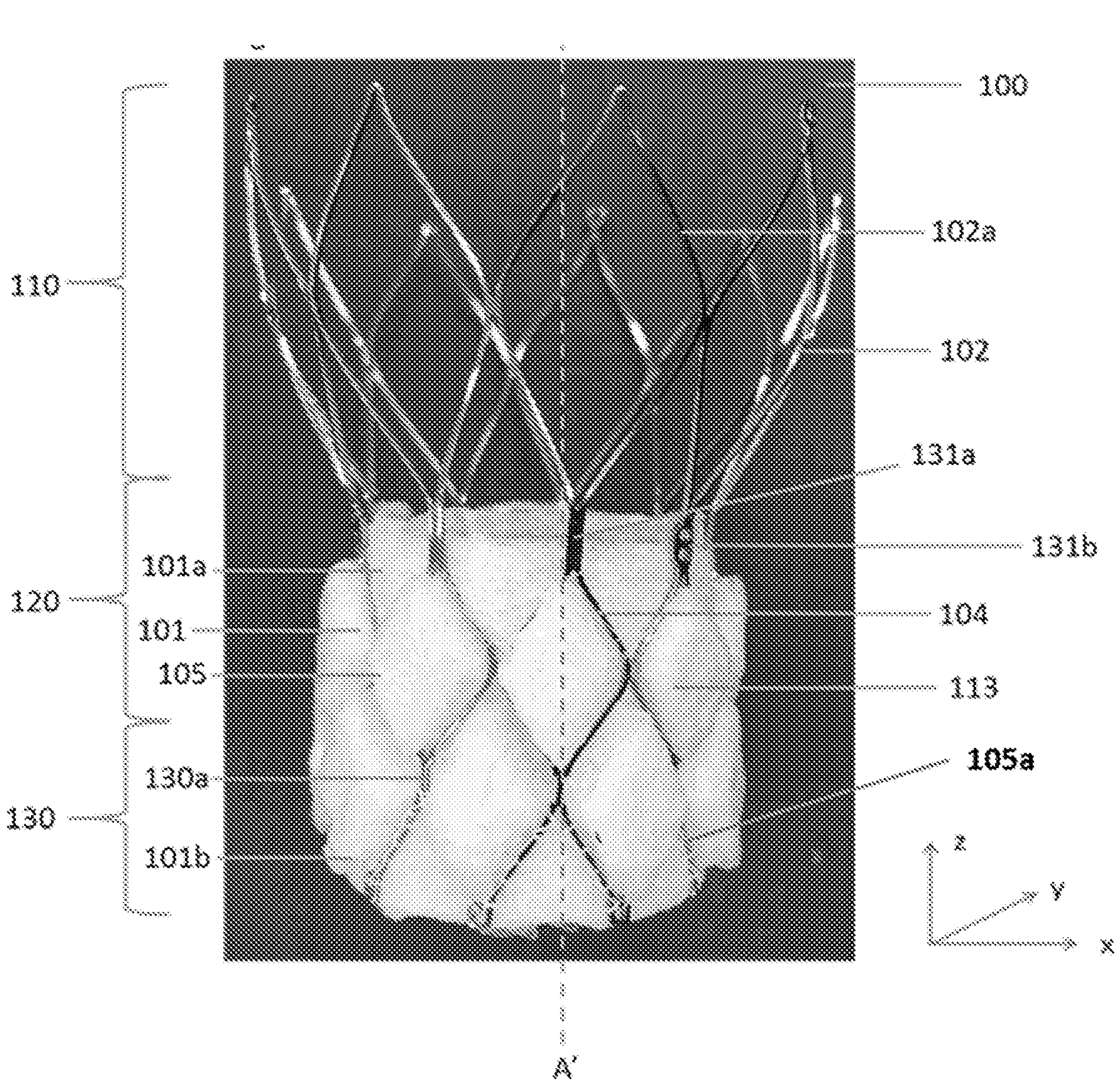
FIG. 1J shows a non-limiting exemplary embodiment of the expandable sealing skirt in a deployed state with a PORTICO® stent frame.
Figure 1K:
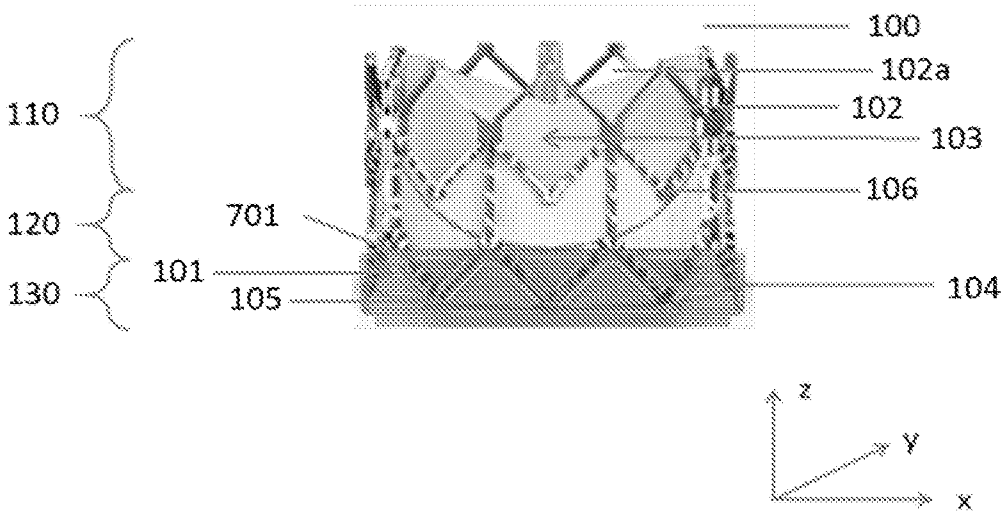
FIG. 1K-1M show non-limiting exemplary embodiments of the expandable sealing skirt in a deployed state (alternatively referred to herein as an expanded sealing skirt or deployed sealing skirt, or sealing skirt) with a SAPIEN® stent frame and valve.
Figure 1L:
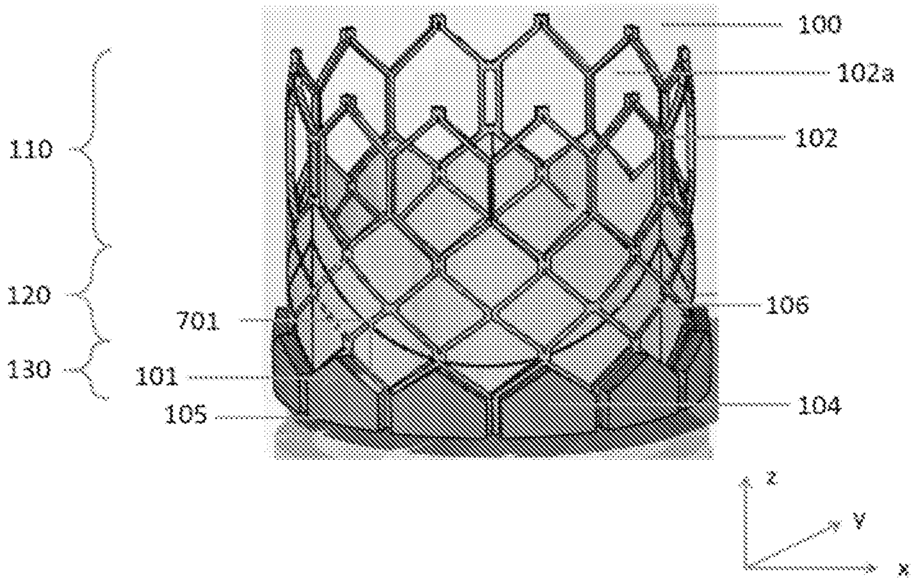
Figure 1M:
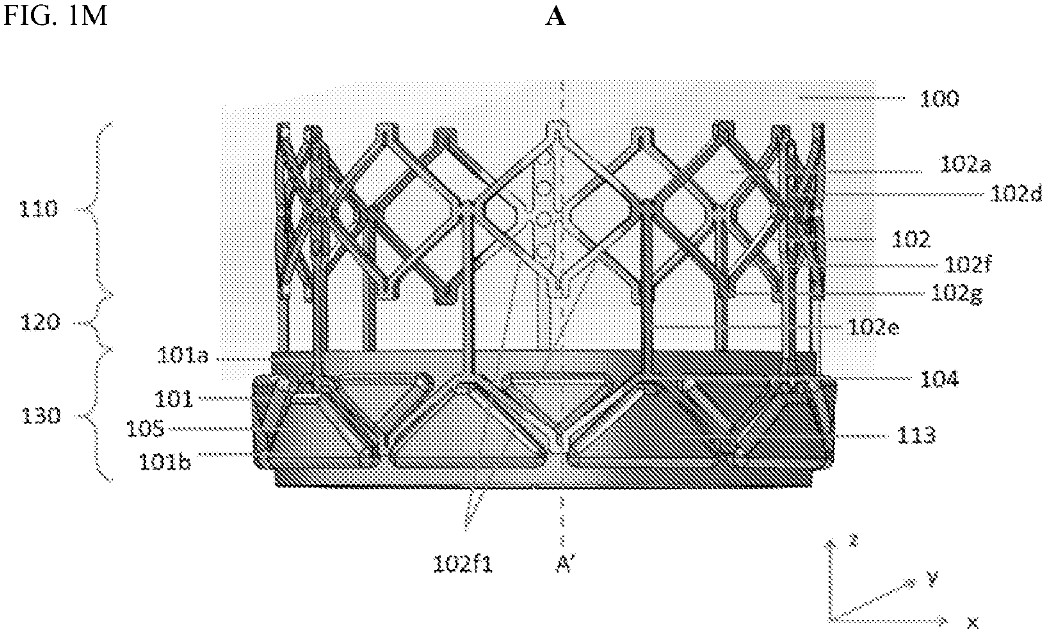
Figure 1M:
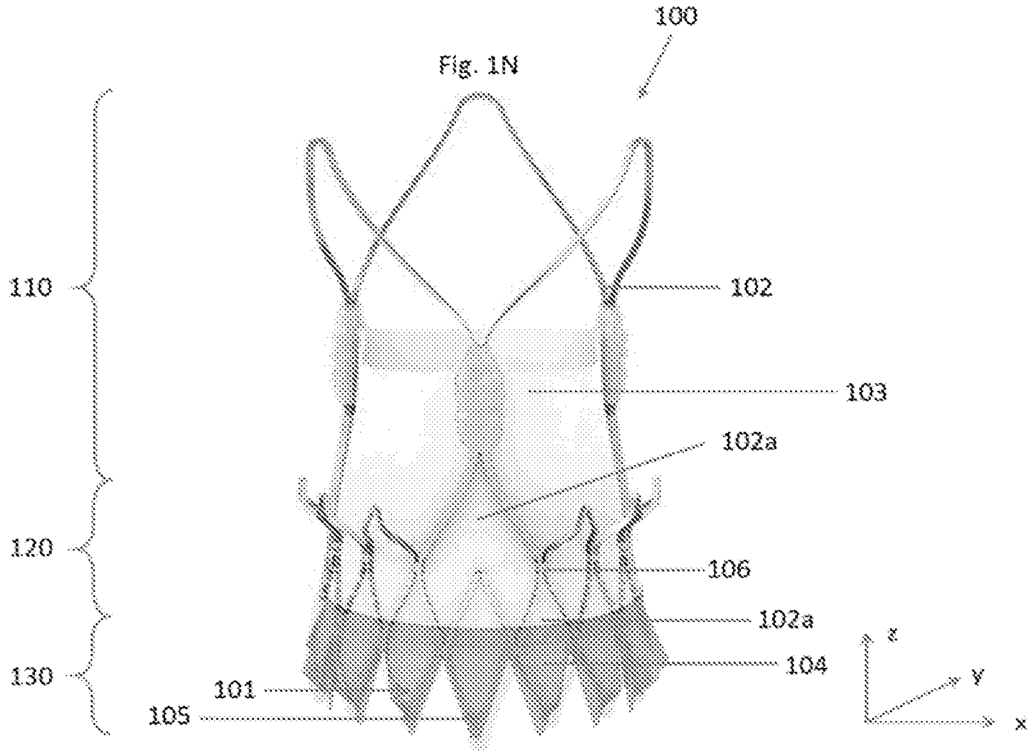
Figure 10:
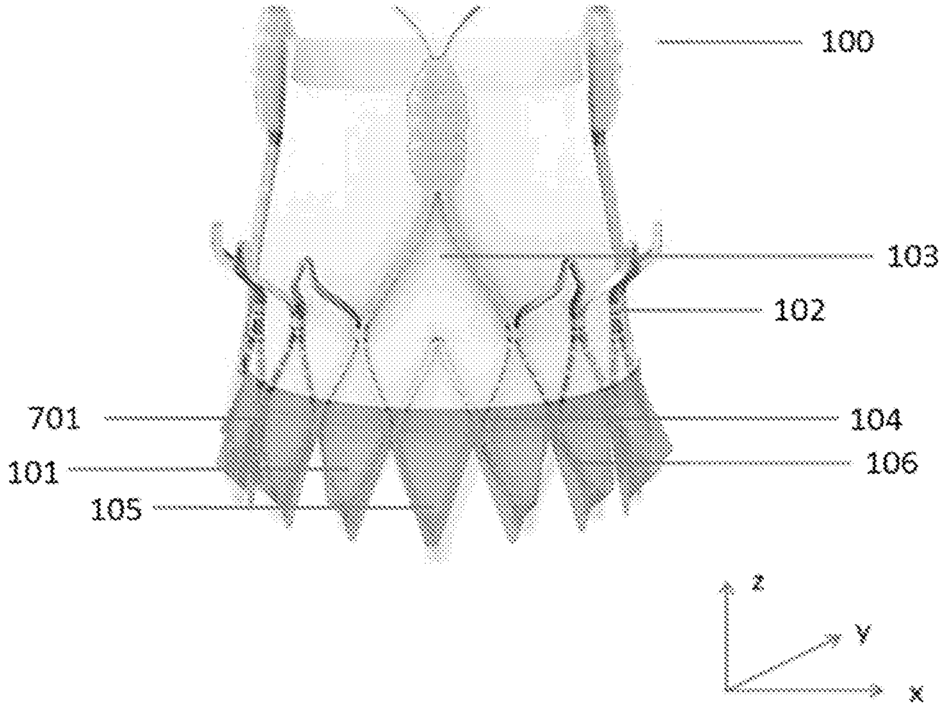
Figure 1P:
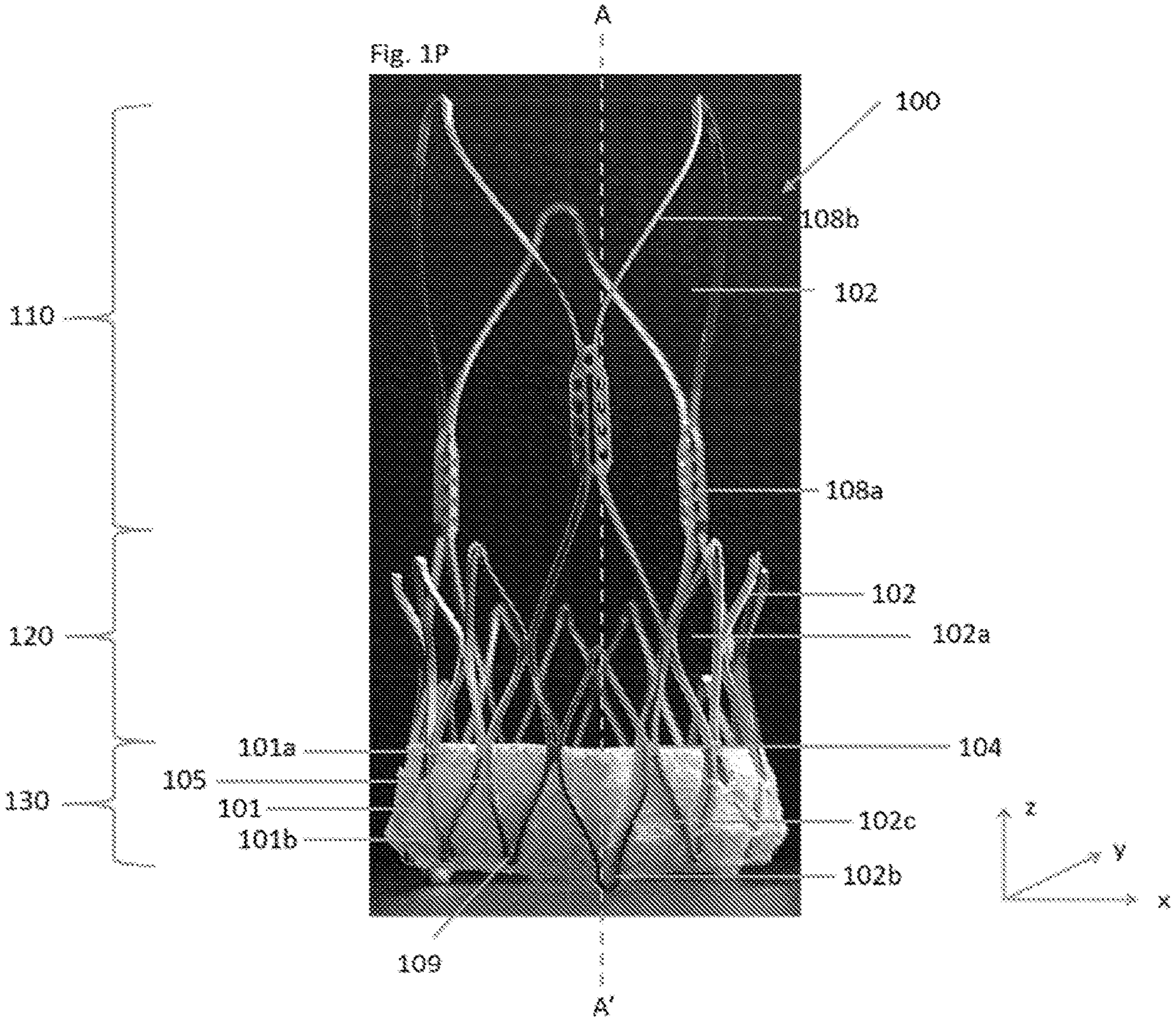
Figures 2A, 2B, 2C, 2D:
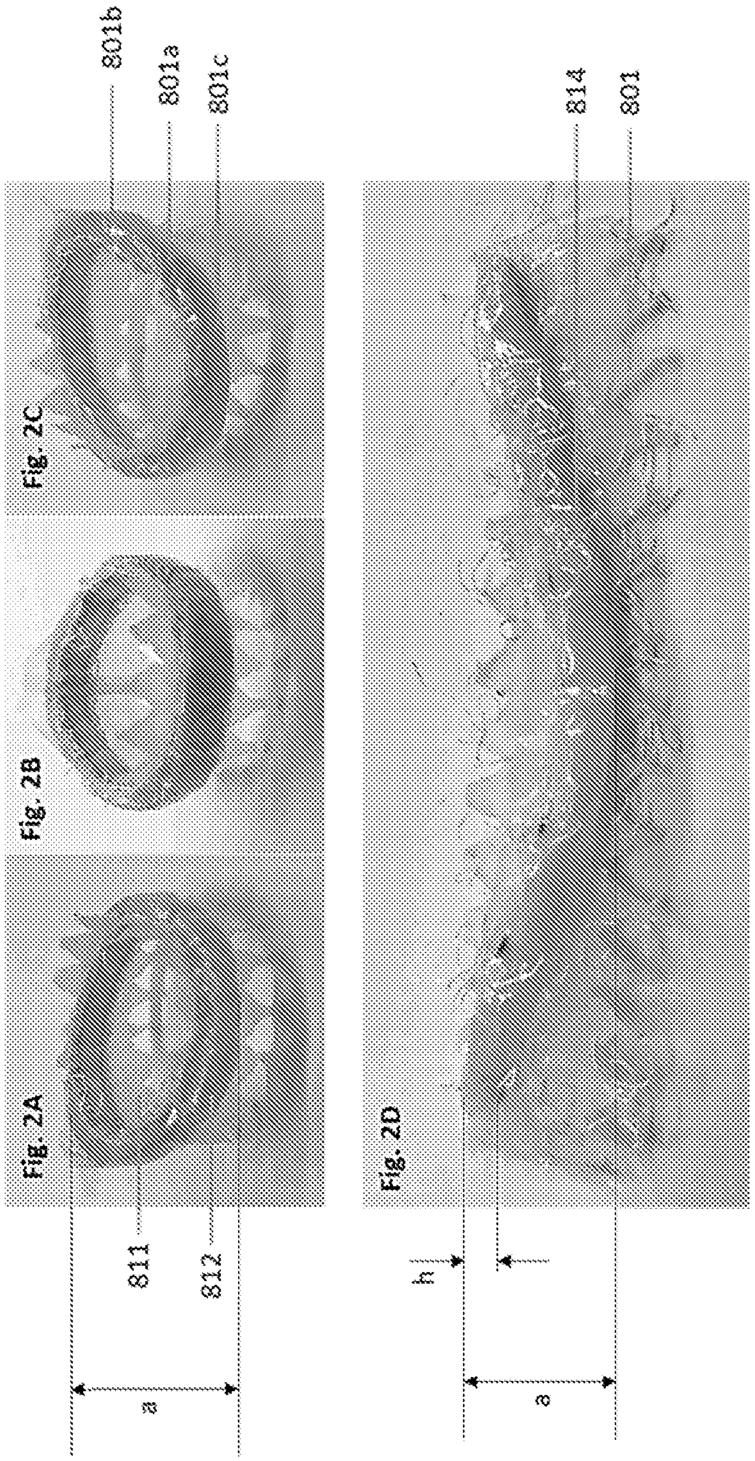
FIGS. 2A-2D show a non-limiting exemplary embodiment of the expandable sealing skirt; in this case, the expandable skirt with an expandable band/ring.

In some embodiments, the skirt may include a ring as its protruding region with a backing as the non-protruding region disclosed herein—FIGS. 2A-2B. The ring may not include more than one protruding cell, or may include two or more protruding cells arranged longitudinally as rings around the circumference of the skirt which rings expand outwardly (radially away from the longitudinal axis of the stent frame) as a whole. The protruding region may include one or more layers of protruding foam cells. The ring expands through the cells of the stent frame to form protruding cells. In some embodiments, the ring is positioned inside the stent frame before its expansion to expand outwardly through the cells of the stent frame. In some embodiments, the ring is positioned outside of the stent frame before its expansion. The skirt may have shapes other than a ring. For example, the skirt may be conical, reverse conical, or any three dimensional shapes depending on the specific deployed shape of the stent frame. In some embodiments, such skirt without individual protruding cells may not compress effectively toward the annulus wall, along the radial direction. In some embodiments, the skirt includes one or more multiple protruding cells 105 that protrude outwardly in the radial direction from the cells of the stent frame as can be seen in FIGS. 1A-1E, 1H-1J, 1K-1M, 1N-1P, and/or 1Q-1W when the skirt is in the deployed configuration. In some embodiments, the protruding cells 105 are formed by deployment of the skirt, due to the skirt protruding region 101*b* pushing against the stent frame and expanding radially out of the cells of the stent frame. In some embodiments, a skirt herein is configured such that the protruding cells protrude outward radially from the center of the stent frame along the radial direction 107. In some embodiments, the protruding cells, form various shapes (e.g., diamond, triangle, etc) having a taper and/or slant in the direction (e.g., z direction, equivalent herein to a longitudinal direction) in which the catheter is pushed during the loading process while loading the device within the catheter. In some embodiments, the taper contour could be in any direction or combination of directions to assist in conformation to any clinical anatomy and/or to adapt to any device/stent platform. For example, the protrusion level of individual cells gradually increases/decreases along the z-direction in which the catheter is pushed during loading of the device within the catheter so that pushing the catheter does not cut or tear the protruding cells.

In some embodiments, the skirt includes a protruding region 101*b* without multiple protruding cells. In some embodiments, a skirt herein is designed so that the protruding (protruding outward radially from the center of the stent frame along radial direction 107, cells (e.g. diamond shaped cells) have a taper/slant in the direction (e.g., z direction, equivalent herein to a longitudinal direction) in which the catheter is pushed during the loading process while loading the device within the catheter. In some embodiments, the taper contour could be in any direction or combination of directions to assist in conformation to any clinical anatomy and/or to adapt to any device/stent platform. For example, the protruding contour along the z direction may be approximately linearly decrease/increase along the z-direction in which the catheter is pushed during loading of the device within the catheter so that pushing the catheter does not cut or tear the protruding cells.

Figure 1Q:
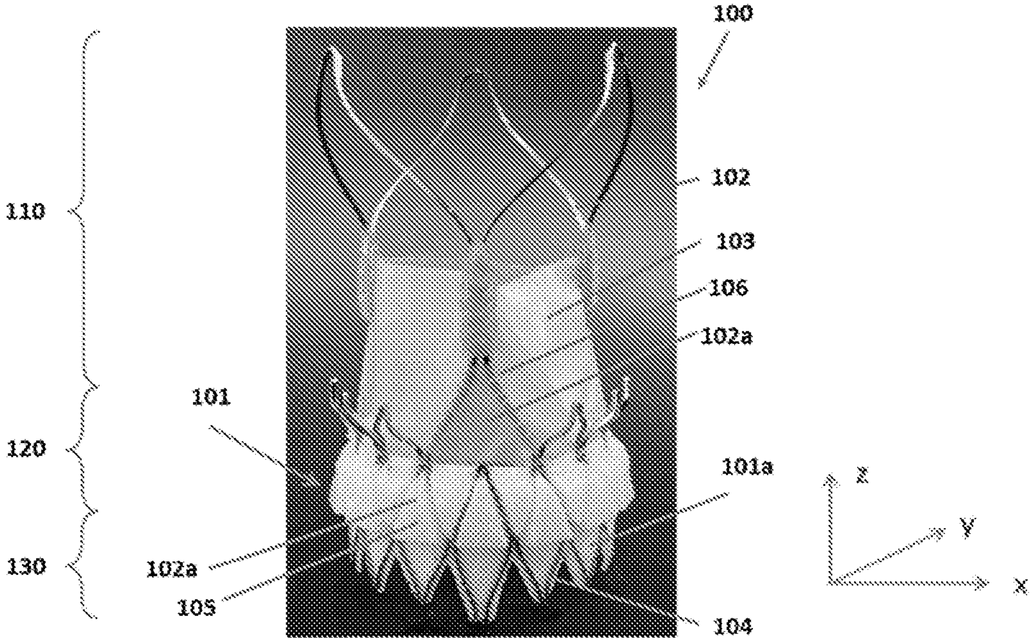
FIGS. 1Q-1T show non-limiting exemplary embodiments of the expandable sealing skirt in a deployed state (alternatively referred to herein as an expanded sealing skirt or deployed sealing skirt, or sealing skirt) with a ACURATE® stent frame and valve.
Figure 1R:
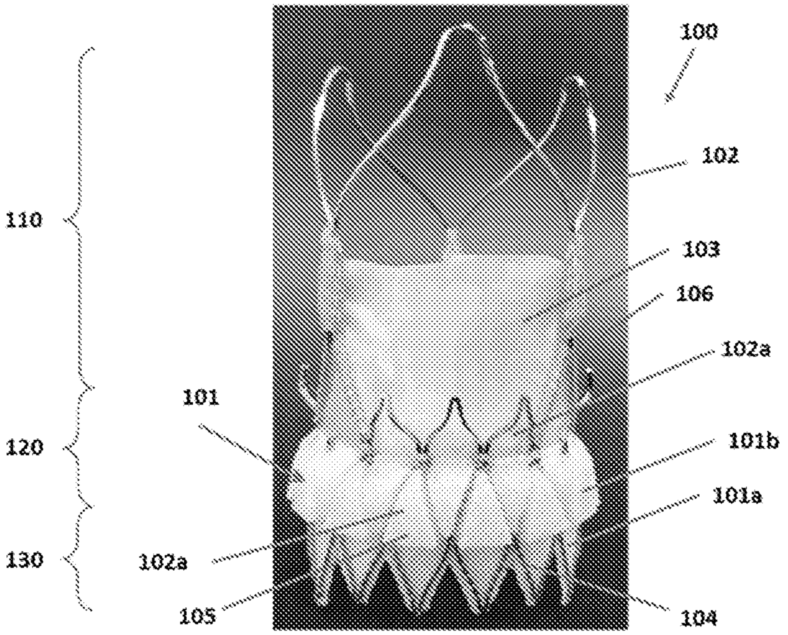
Figures 1S, 1T:
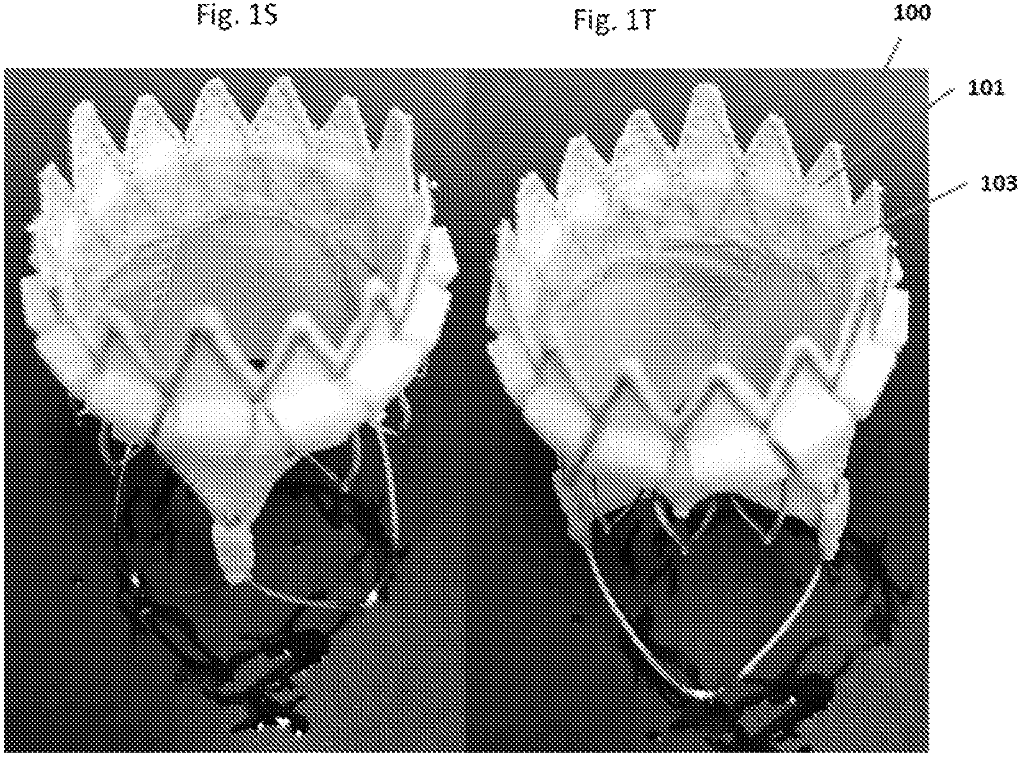

In some embodiments, the protruding region 101*b* of the skirt 101 comprises one or more layers of protruding cells 105, wherein the layers are offset in a z-direction (as shown in FIG. 1E, FIG. 1J, FIG. 1M, and/or in FIGS. 1P-1Q for non-limiting examples). In some embodiments, the protruding region 101*b* of the skirt 101 comprises one or more layers of protruding cells 105, wherein the layers are offset by less than a length of a cell as measured in the z-direction (as shown in FIG. 1E, FIG. 1J, FIG. 1M and/or in FIGS. 1P-1Q, for non-limiting examples). In some embodiments, the protruding region 101*b* of the skirt 101 comprises one or more layers of protruding cells 105, wherein the layers are offset by less than a length of a layer as measured in the z-direction (as shown in FIG. 1E, FIG. 1J, FIG. 1M and/or in FIGS. 1P-1Q, for non-limiting examples). In some embodiments, the protruding cells 105 of adjacent layers are staggered such that a center of a first protruding cell of a first layer falls between the center of a second protruding cell and the center of a third protruding layer adjacent the second protruding cell of a second layer. In some embodiments, the protruding cells 105 of adjacent layers are formed by conforming to the shape of the stent frame or at least a portion of the shape of the stent frame.

In some embodiments, the protrusion dimensions can be varied depending on the application (how far outward the protrusion extends). In some embodiments, for applications other than the transcatheter valve application, the protrusions can be in both luminal and vessel wall directions (inner and outer wall). In some embodiments, the maximal protrusion thickness (along the radial direction 107) when expanded is about 10%, about 50%, about 80%, about 90%, about 100%, about 110%, about 120%, about 130%, about 140%, about 150%, about 160%, about 170%, about 180%, about 190%, about 200%, about 300%, about 400%, about 500%, about 600%, about 700%, about 800%, about 1000%, about 1200%, about 1500%, about 1800%, about 2000%, about 2200%, about 2500%, or about 3000% of the thickness in non-protruding regions or the connection region or the connecting cells of the skirt. In some embodiments, the maximal protrusion thickness (along the radial direction 107) can range from about 10% to about 3000% of the thickness in non-protruding regions of the skirt. In some embodiments, the maximal protrusion thickness (along the radial direction 107) can range from about 1000% to about 3000% of the thickness in non-protruding regions of the skirt. In some embodiments, the maximal protrusion thickness (along the radial direction 107) can range from about 2000% to about 3000% of the thickness in non-protruding regions of the skirt. In some embodiments, the protrusion is in the range of about 50% to about 3500% of the thickness in non-protruding regions of the skirt. For example, if the non-protruding region has a thickness of about 0.066 mm, the maximal protrusion of 3000% is about 2 mm. In some embodiments, the maximal protrusion thickness (along the radial direction 107) can range from about 10% to about 3000% of the thickness in connection region or the connecting cells of the skirt. In some embodiments, the maximal protrusion thickness (along the radial direction 107) can range from about 1000% to about 3000% of the thickness in connection region or the connecting cells of the skirt. In some embodiments, the maximal protrusion thickness (along the radial direction 107) can range from about 2000% to about 3000% of the thickness in connection region or the connecting cells of the skirt. In some embodiments, the protrusion is in the range of about 50% to about 3500% of the thickness in connection region or the connecting cells of the skirt. In some embodiments, the maximal protrusion thickness (along the radial direction 107) is about 0.1 mm to about 10 mm. In some embodiments, the maximal protrusion thickness (along the radial direction 107) is about 1 mm to about 5 mm. In some embodiments, the maximal protrusion thickness (along the radial direction 107) is 10%, 50%, 80%, 90%, 100%, 110%, 120%, 130%, 140%, 150%, 160%, 170%, 180%, 190%, 200%, 300%, 400%, 500%, 600%, 700%, 800%, 1000%, 1200%, 1500%, 1800%, 2000%, 2200%, 2500%, or 3000% of the thickness in non-protruding regions or connection regions or connecting cells of the skirt. In some embodiments, the maximal protrusion thickness (along the radial direction 107) can range from 10% to 3000% of the thickness in non-protruding regions of the skirt. In some embodiments, the maximal protrusion thickness (along the radial direction 107) can range from 1000% to 3000% of the thickness in non-protruding regions of the skirt. In some embodiments, the maximal protrusion thickness (along the radial direction 107) can range from 2000% to 3000% of the thickness in non-protruding regions of the skirt. In some embodiments, the protrusion is in the range of 50% to about 3500% of the thickness in non-protruding regions of the skirt. For example, if the non-protruding region has a thickness of 0.066 mm, the maximal protrusion of 3000% is about 2 mm. In some embodiments, the maximal protrusion thickness (along the radial direction 107) is 0.1 mm to 10 mm. In some embodiments, the maximal protrusion thickness (along the radial direction 107) is 1 mm to 5 mm. In some embodiments, the maximal protrusion thickness (along the radial direction 107) can range from 10% to 3000% of the thickness in connection region or the connecting cells of the skirt. In some embodiments, the maximal protrusion thickness (along the radial direction 107) can range from 1000% to 3000% of the thickness in connection region or the connecting cells of the skirt. In some embodiments, the maximal protrusion thickness (along the radial direction 107) can range from 2000% to 3000% of the thickness in connection region or the connecting cells of the skirt. In some embodiments, the protrusion is in the range of 50% to about 3500% of the thickness in connection region or the connecting cells of the skirt.

In some embodiments, a skirt here includes a non-protruding region 101*b*. The non-protruding region is connected to protruding region and thus to the protruding cells 105. In some embodiments, the non-protruding region includes a portion that is located above or below the protruding cells along the z direction. In some embodiments, the non-protruding region includes a portion that is overlapping with the protruding cells along the z direction. In some embodiments, the non-protruding region is enclosed within the stent frame and is not protruding out of the stent frame as in FIG. 1E, FIG. 1J, FIG. 1M, FIGS. 1P-1Q and/or in FIG. 1U. In some embodiments, the connection region is enclosed within the stent frame and is not protruding out of the stent frame. In some embodiments, the connection cell is enclosed within the stent frame and is not protruding out of the stent frame.

In some embodiments, the skirt disclosed herein, after deployment with the stent frame, can be made in any three-dimensional geometrical shape. In some embodiments, the skirt disclosed herein, after deployment with the stent frame, is substantially a hollow cylinder (FIGS. 1P and 1U), a substantially donut shape, a substantially ring shape (FIGS. 1W and 5O), a substantially hollow conical shape, a substantially hollow reverse conical shape, or a combination thereof. Nonlimiting examples include: conical, reverse conical, cylindrical, and spherical shapes. Nonlimiting examples of the geometrical shape is in FIGS. 1A-1E, 1H-1J, 1K-1M, 1N-1W, 4O, and/or 5O. In some embodiments, the skirt herein designed for the transcatheter valve application is that the e inner (luminal) wall of the skirt is relatively flat (along z direction and/or along x, y, x-y direction) and the portion against the vessel wall is protruded. In some embodiments, the skirt herein designed for the transcatheter valve application is that the inner (luminal) wall 111 of the skirt is relatively flat (at least along the z direction and/or along the x-z, y-z directions) and the portion against the vessel wall (outer wall of the skirt 112) is protruded (along the radial direction, x direction, y direction, or x-y direction). In some embodiments, the portion against the calcification (outer wall of the skirt 112) is protruded. In some embodiments, the protrusion is when the skirt is in a deployed state. In some embodiments, the skirt has a deployed diameter (along x, y, or radial direction) of about 4 to about 10 mm. In some embodiments, the skirt has a deployed height (along z direction) of about 6-18 mm. In some embodiments, the skirt has a maximal or minimal cell size of about 0.1 $mm^2$ to about 10 $mm^2$. In some embodiments, the skirt has a maximal or minimal cell size of about 1 $mm^2$ to about 5 $mm^2$. In some embodiments, the skirt has a deployed diameter (along x, y, or radial direction) of 4 to 10 mm. In some embodiments, the skirt has a deployed height (along z direction) of 6-18 mm. In some embodiments, the skirt has a maximal or minimal cell size of 0.1 $mm^2$ to 10 $mm^2$. In some embodiments, the skirt has a maximal or minimal cell size of 1 $mm^2$ to 5 $mm^2$.

In some embodiments, the expandable skirt includes the foam cells 105 that can be arranged in various patterns. Nonlimiting exemplary arrangement patterns are shown in FIGS. 7A-7D, which shows a skirt 101 laid flat in a single plane, wherein the patterns constitute two or more rows or layers of protruding regions, or foam cells, 101*b* as shown by the first row (first layer) with cells d1, d3, d5 . . . dn (conforming to at least a part of the shape determined by the open ends and adjacent struts at the distal end, e.g., triangular protruding cells) and the second row (second layer) with cells d2, d4, d6 . . . dn+1 (fitting at least a portion of the most distal layer of closed stent cells, e.g., diamond cells or substantially diamond cells). Adjacent cells in this embodiment may be separated by a small gap, e.g., G in FIG. 6B. In some embodiments, the gap may be in the range of 0.1 mm to 1 mm. The non-protruding region 101*a* is not constituted by the protruding region. The gap may alternatively be called the connection region herein.

As used herein, with respect to the expandable stent cells and/or the protruding cells, a "hexagon" shape is synonymous with "substantially hexagon," "approximately hexagon," or "generally hexagon" and refers to a shape having six legs (or alternatively called struts, or alternatively called arms) and six inflections (some or all of them may be of a U-shape). In some embodiments, the one or more legs are straight. In some embodiments, the one or more legs are not straight but curved. The "hexagon" shape, in some embodiments, does not have six legs that are equal in length. In some embodiments, the "hexagon" shape has six legs are equal in length. In some embodiments, the "hexagon" shape has four legs are equal in length and the other two legs that are equal to each other but of a different length.

In some embodiments, the hexagon shape herein is a concave hexagon as shown in FIG. 1P at least, with at least one vertex or inflection pointing inward. In some embodiments, the concave hexagon shares the same property of the "hexagon" shape herein with at least one vertex or inflection pointing inward.

As used herein, with respect to the expandable stent cells and/or the protruding cells, a "pentagon" shape is synonymous with "substantially pentagon," "approximately pentagon," or "generally pentagon" and refers to a shape having five legs (or alternatively called struts, or alternatively called arms) and five inflections (some of them or all of them may be of a U-shape). In some embodiments, the one or more legs are straight. In some embodiments, the one or more legs are not straight but curved. The "pentagon" shape, in some embodiments, does not have five legs that are equal in length. In some embodiments, the "pentagon" shape has five legs are equal in length. In some embodiments, the "pentagon" shape has two legs are equal in length and the other two legs that are equal to each other but of a different length.

As used herein, with respect to the expandable stent cells and/or the protruding cells, a "partial-hexagon" shape is synonymous with "partially hexagonal," "substantially partially-hexagon" or "generally partially hexagon" and refers to a shape approximating a hexagon that has been cut off such that it forms a 5-sided shape having two edges of equal length, or 4 sides of equal length, and one longer having no other edge of equal length to it (edges are alternatively called struts, or alternatively called arms, or alternatively called legs) and five inflections (some of them may be of a U-shape). A half-hexagonal shape, or half-hexagon shape is one in which a hexagon shape, as defined herein, has been cut into two portions of equal area. An embodiment of partially hexagonal shape is shown in the protruding cells of FIG. 1L, for nonlimiting example.

As used herein, with respect to the expandable stent cells and/or the protruding cells, a "chevron" shape is synonymous with "substantially chevron" or "v-shaped" and refers to a shape approximating a chevron and/or "v" pointing distally and having (when laid flat) two parallel edges (usually of equal length) which extend longitudinally substantially parallel or parallel to the longitudinal central axis of the stent, and a first set of edges of equal length connected to each other by an inflection pointing distally and connected to the parallel edges by inflections, forming an "M" shape, and also includes a second set of edges of equal length connected to each other by an inflection which forms the distalmost portion of the chevron, wherein each of edges of the second set of edges connects at inflections to the parallel edges at opposite ends of the parallel edges as compared to the ends connected to the first set of edges, completing the chevron shape. An embodiment of a chevron shape stent cell is FIG. 3O in the mid portion 120 of the stent, for nonlimiting example. The chevron shape may also be referred to as a concave hexagon shape or concave hexagonal shape or substantially concave hexagon shape herein.

In some embodiments, the expandable skirt only have a single row of cells e.g. row d1, d3, d5 . . . dn, or row d2, d4, d6 . . . dn+1. In some embodiments, the skirt can randomly distributed cells in one or two rows, e.g. d1, d2, d3, d4 only, or d1, d2, d5, d6 only, and the rest of the skirt that is not occupied by the cells are the non-protruding region 101*a*.

Figure 6A:
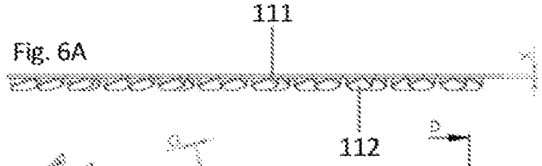
FIGS. 6A-6E show a non-limiting exemplary embodiment of the expandable sealing skirt; in this case, the expandable skirt in different views before and after assembling on to the stent.
Figure 6B:
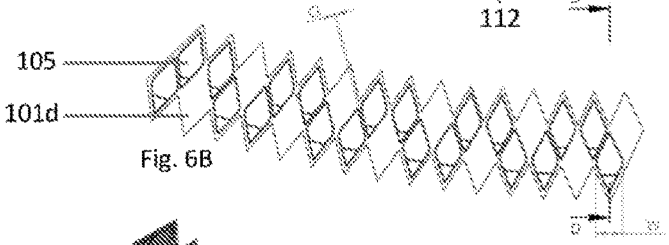
Figure 6D:
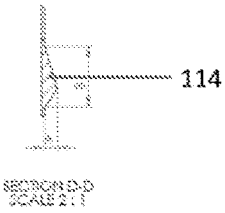
Figure 6C:
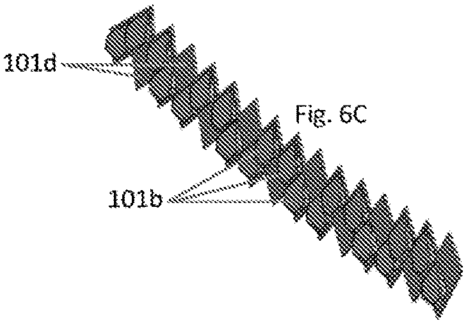
Figure 6E:
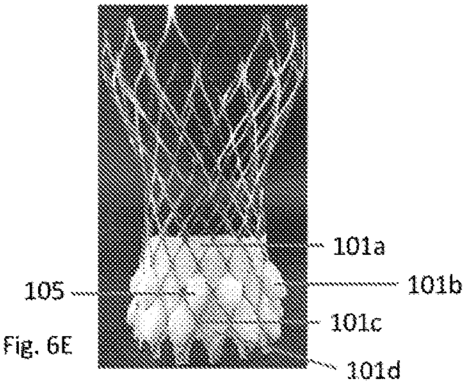
Figure 7A:
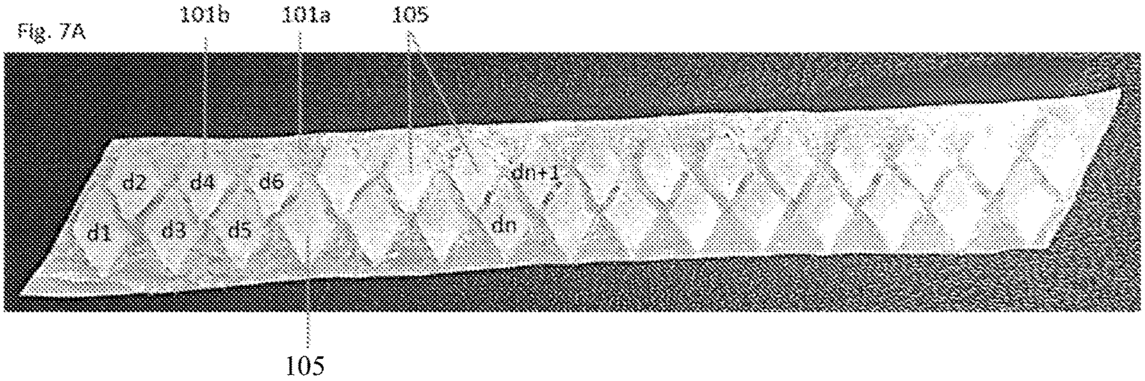
FIG. 7A-7D shows a non-limiting exemplary embodiment of the expandable sealing skirt; in this case, the cell arrangement in the expandable skirt before assembling on to the stent.
Figure 7B:
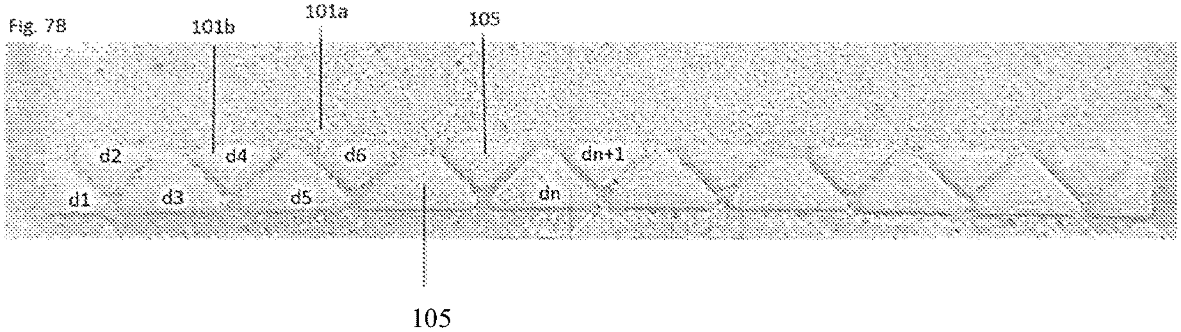
Figure 7C:
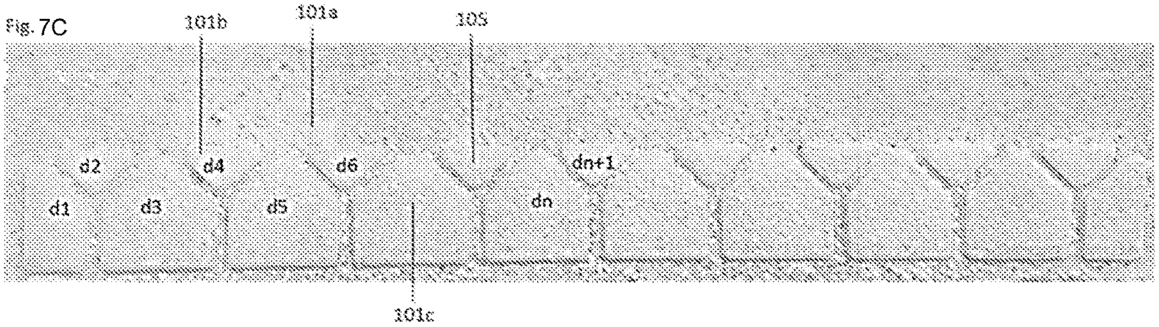
Figure 7D:
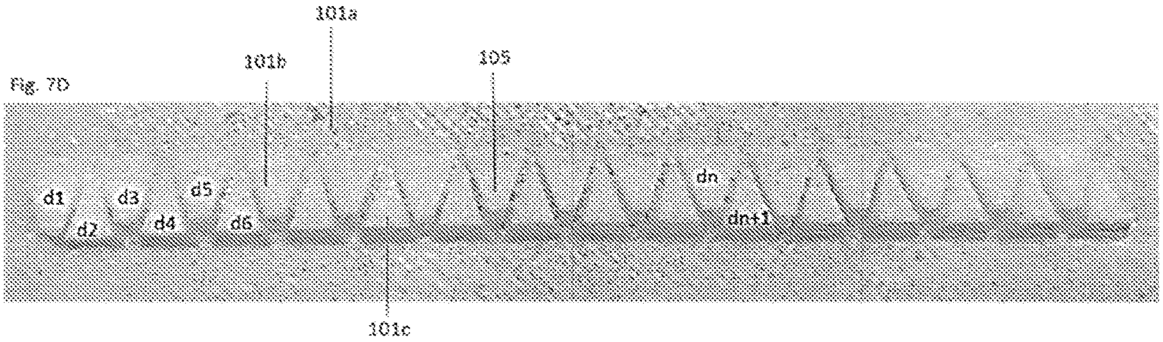
Figure 8A:
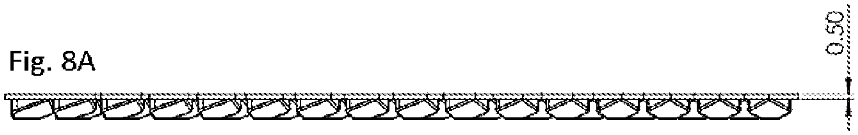
FIGS. 8A-8D show a non-limiting exemplary embodiment of the expandable sealing skirt; in this case, the expandable skirt in different views before assembling on to the COREVALVE® stent.
Figure 8B:
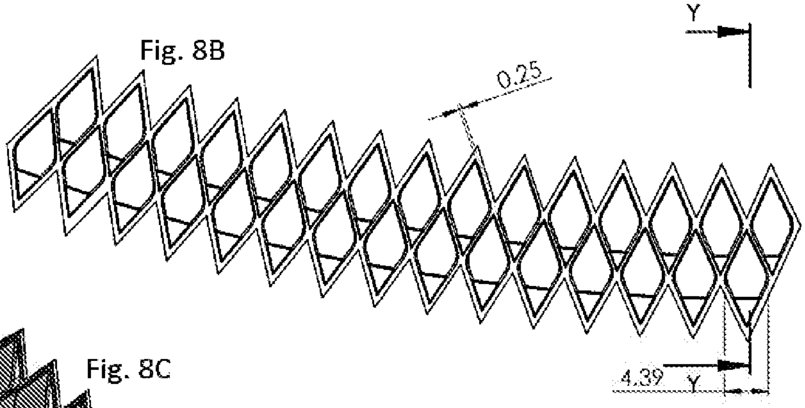
Figure 8C:
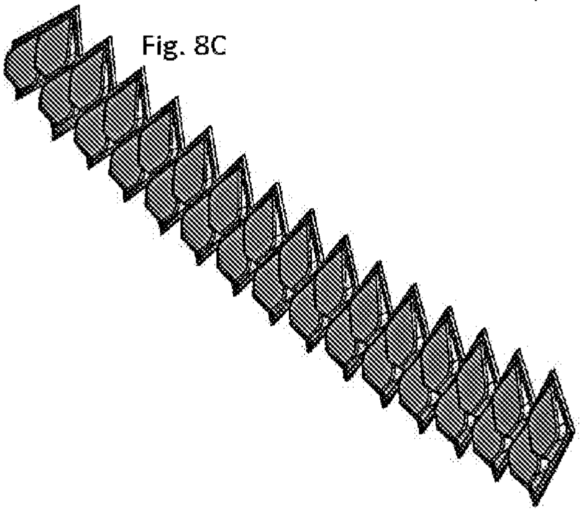
Figure 8D:
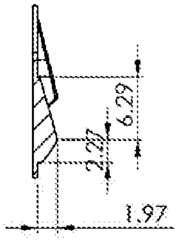
Figure 8E:
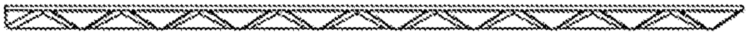
FIGS. 8E-8H show a non-limiting exemplary embodiment of the expandable sealing skirt; in this case, the expandable skirt in different views before assembling on to the PORTICO® stent.
Figure 8F:
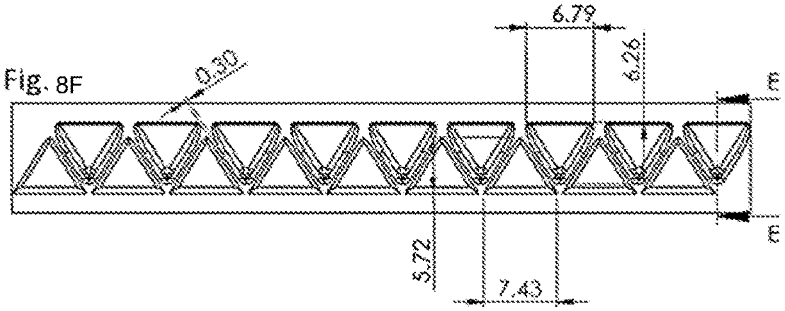
Figure 8H:
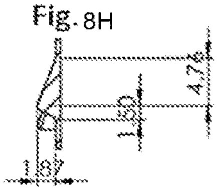
Figure 8G:
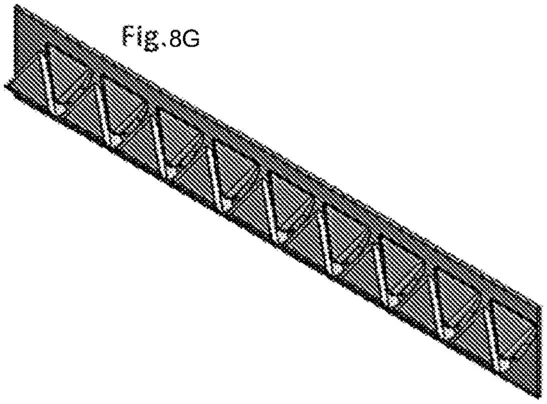
Figure 8I:
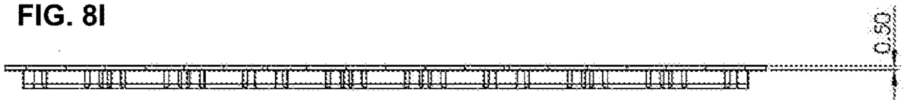
FIGS. 8I-8L show a non-limiting exemplary embodiment of the expandable sealing skirt; in this case, the expandable skirt in different views before assembling on to the SAPIEN® stent.
Figure 8J:
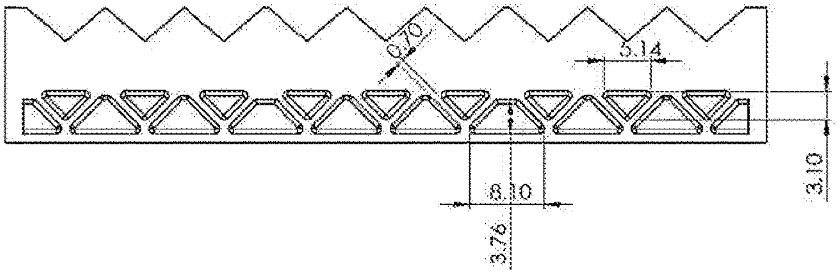
Figure 8L:
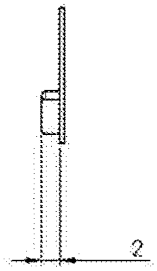
Figure 8K:
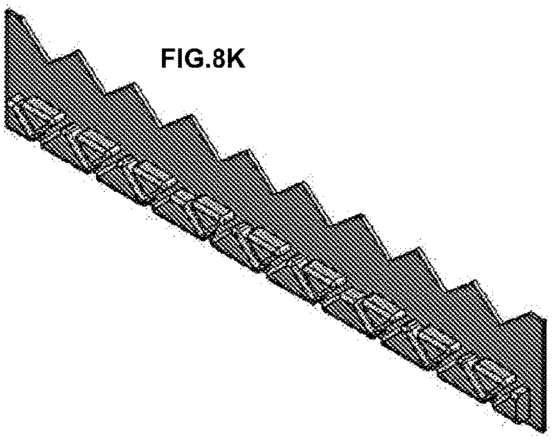
Figure 8M:
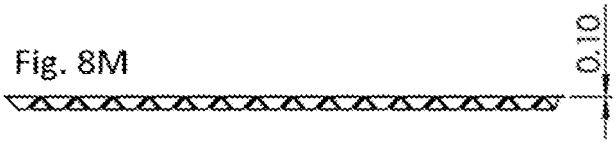
FIGS. 8M-8P show a non-limiting exemplary embodiment of the expandable sealing skirt; in this case, the expandable skirt in different views before assembling on to the ACURATE® stent.
Figure 8N:
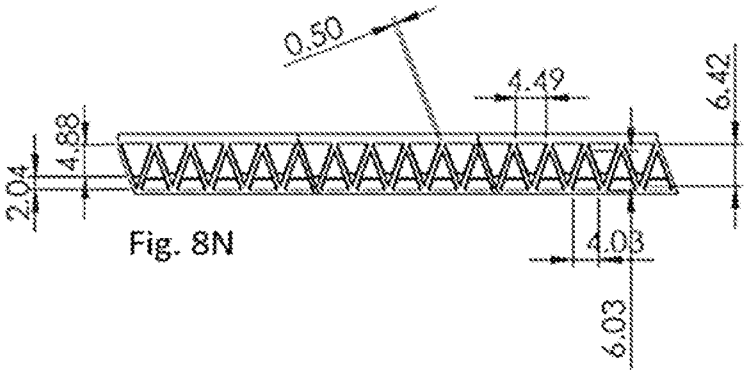
Figure 8P:
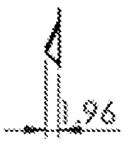
Figure 8O:
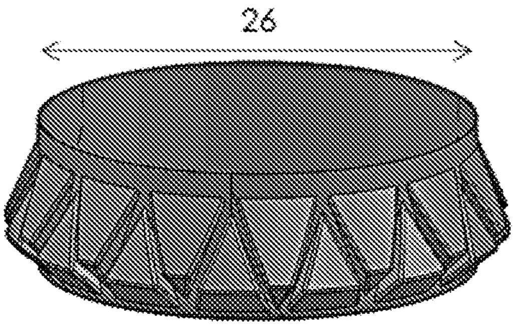

In some embodiments, the expandable skirt herein includes the foam cells 105 that arranged in an alternate or staggered pattern. An exemplary alternate or staggered pattern is shown in FIGS. 6A-6E. An exemplary alternate or staggered pattern is shown in FIG. 1M. In some embodiments, the arrangement of cells corresponds to the pattern including cells d1, d2, d4, d5, d6, d8, d9 . . . as shown in FIG. 6A, in which the alternate odd numbers are omitted—d3, d7, etc. As shown therein the protruding region 101*b* includes protruding cells 105, connection regions (or gaps G), and connection cells 101*d*. In this embodiment, the arrangement allows for achieving even lower crimping profile due to the reduction of mass density across the longitudinal sections/planes of the device without affecting the performance of leak-prevention. In such embodiments, there are protruding cells extending radially beyond (farther from the longitudinal axis of the stent frame) the stent frame adjacent thereto for the entire circumference of the device assembly, despite each layer of the stent cells having protruding cells not having protruding cells through each stent cell of such layer. In some embodiments, the cells 105 can optionally have a skin 101*c* on the outer surface 112 of the skirt—the skin can have a thickness ranging from a few nanometers to microns, or even thicker. In some embodiments, the skin can be of the same or different material to the skirt and can be attached using chemical means, physical means e.g. adhesive, etc. or heat or dip coating, among others. In this embodiment, a cross section (D-D of FIG. 6B) of each individual cell is shown in FIG. 6D. In some embodiments, the pattern of protruding cells and connecting cells corresponds to the pattern shown in FIGS. 6A-6C while the shape of the protruding cell and/or the shape of the connecting cell correspond to the shape(s) shown in FIG. 6D.

Figures 5A, 5B, 5C, 5D:
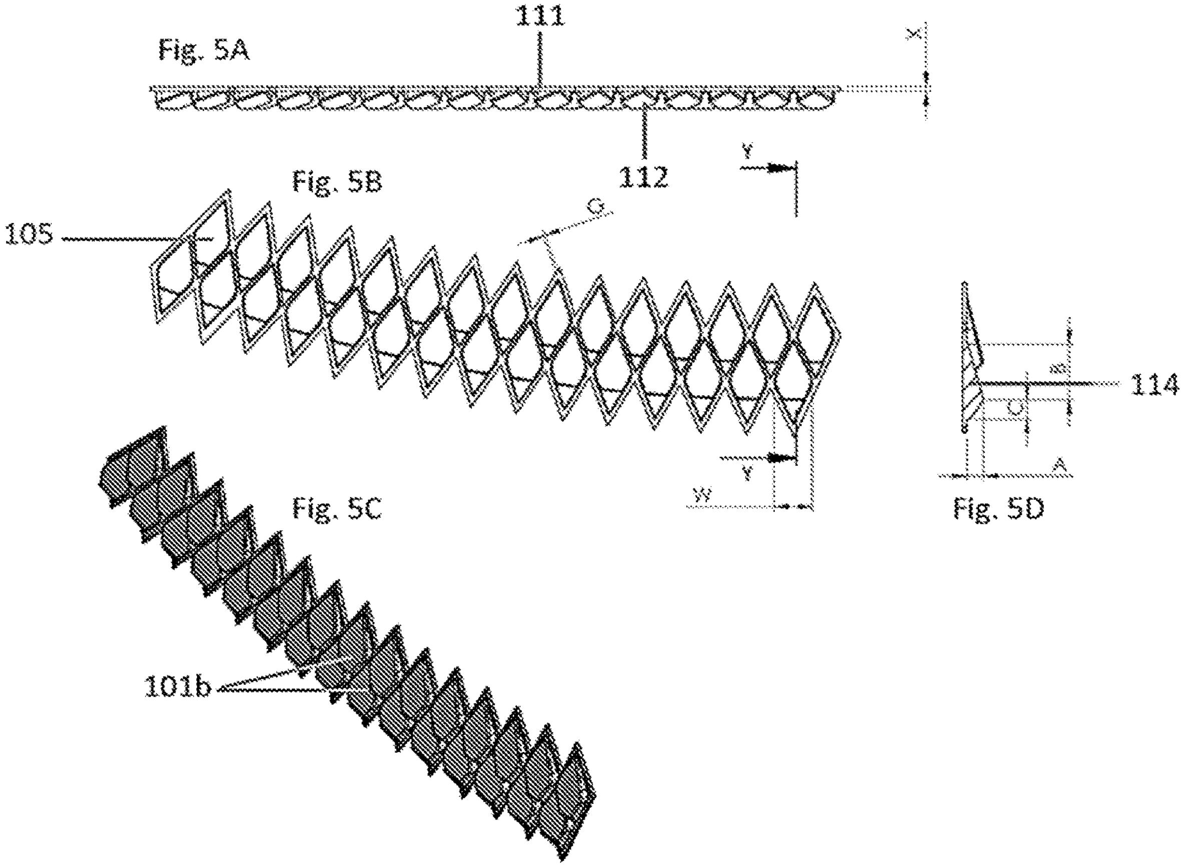
FIGS. 5A-5D show a non-limiting exemplary embodiment of the expandable sealing skirt; in this case, the expandable skirt in different views before assembling on to the COREVALVE® stent.

FIGS. 7A-7D show exemplary embodiments of pattern for foam cells when the expandable skirt is cut at the circumference and laid flat. In this embodiment, the foam cells 105 of the protruding region 101*b* are arranged in an alternate or staggered pattern. In this embodiment, the arrangement of cells corresponds to the pattern including cells d1, d2, d4, d5, d6 . . . dn, dn+1 . . . . In some embodiments, adjacent protruding cells are not of the same area, e.g., d2 and d3, d3 and d4. In some embodiments, the bottom layer of protruding cells, i.e., d1, d3, d5, . . . dn, are larger than the adjacent layer of cells, i.e., d2, d4, d6, . . . dn+1, which even numbered protruding cells are located more toward the top (proximal) portion of the assembly. An embodiment cross section of a protruding region including two protruding cells (FIG. 7A) is shown in FIG. 5D. An embodiment cross section of FIG. 7B of a protruding region including two protruding cells is shown in FIG. 5H. An embodiment cross section of FIG. 7C of a protruding region including two protruding cells is shown in FIG. 5L. An embodiment cross section of FIG. 7D of a protruding region including two protruding cells is shown in FIG. 5M.

Figures 4A, 4B, 4C, 4D:
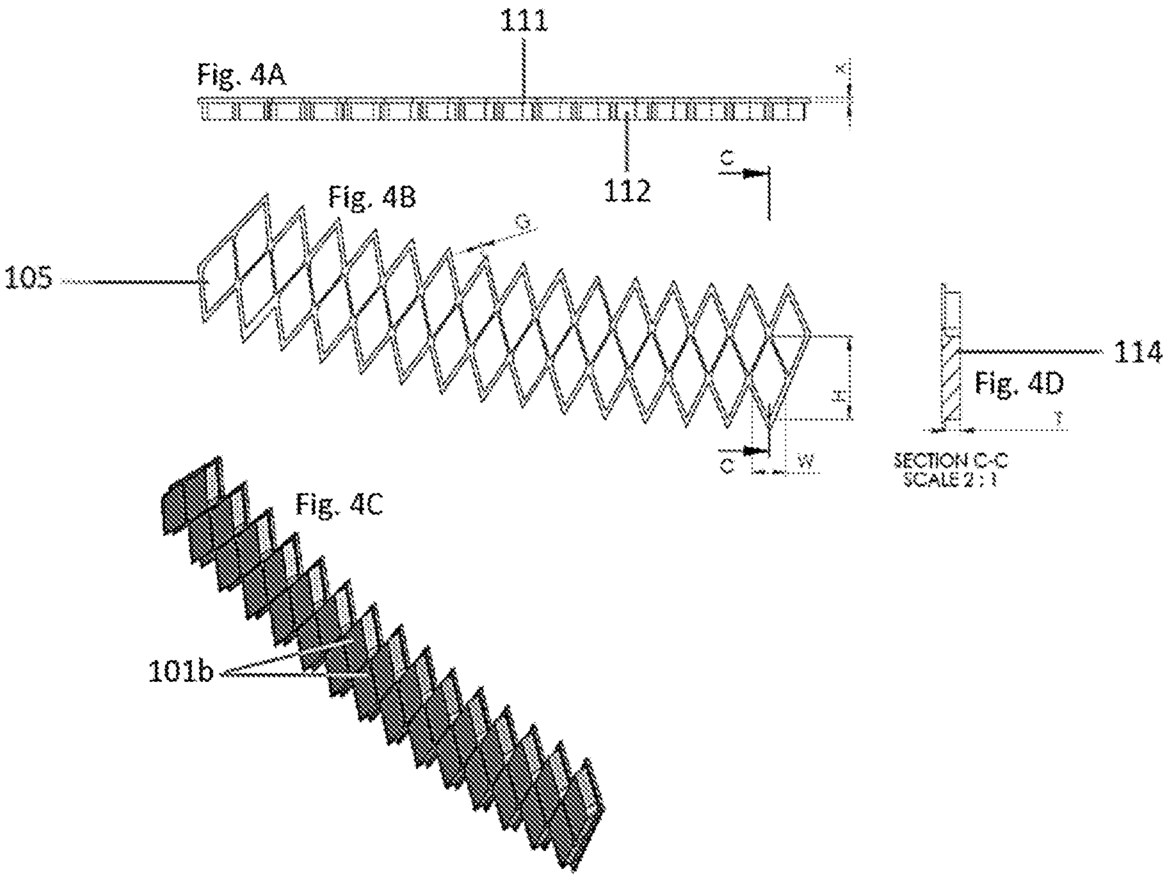
FIGS. 4A-4D show a non-limiting exemplary embodiment of the expandable sealing skirt; in this case, the expandable skirt in different views before assembling on to the COREVALVE® stent.

In some embodiments, the expandable skirt includes the foam cells 105 that can be arranged in a uniform pattern where the cells have a cross section (section C-C) profile of an approximate rectangle 114, as shown in FIG. 4D and FIG. 1F. The thickness, or dimension in the radial direction is T. In this particular embodiment, thickness T can have a range from about 50 microns to about 5 millimeter. In some embodiments, the thickness T is from 10 um to about 8 mm. In some embodiments, the thickness T is from 10 um to about 100 um. In some embodiments, the thickness T is from 30 um to about 200 um. In some embodiments, the thickness T is from 30 um to about 400 um. In some embodiments, the thickness T is from 50 um to about 1 mm. In some embodiments, the thickness T is from 100 um to about 3 mm. In some embodiments, the thickness T is from 200 um to about 6 mm.

In some embodiments, the expandable skirt includes the foam cells 105 that can be arranged in a non-uniform pattern along the longitudinal direction (as in FIG. 4I-4K) where the cells have a cross section along the radial direction of an approximate rectangle 114, as shown in FIG. 4L. In the particular embodiment shown in FIGS. 4I-4K, the protruding foam cells are arranged in two layers that conform to the arrangement of the most distal layer of stent cells and the distal open ends that are more distal to them. In this embodiment, the more proximal layer of foam cells is smaller and of a substantially triangular shape, the more distal layer of foam cells are much larger and are of a hexagon or pentagon shape. In some embodiments, the more proximal layer of foam cells only occupies a part of the stents cells that the protruding cells protrude from as shown in FIG. 1M. In some embodiments, the stents cells that the protruding cells protrude from are open stent cells. In some embodiments, the stents cells that the protruding cells protrude from are open stent cells formed by the distalmost struts and vertices of the distal layer of stent cells. In some embodiments, the stents cells that the protruding cells protrude from are open stent cells formed by the distalmost struts and vertices of the distal layer of stent cells and extending legs extending from the distalmost struts and/or vertices of the distal layer of stent cells. In some embodiments, the stents cells that the top layer of foam cells protrudes from are substantially hexagon, or pentagon. The thickness of a foam cell in the radial direction is A. The non-protruding region 101*a* extends more proximally than the protruding region 101*b*. The proximal edge of the non-protruding region can have a zig-zag profile as shown in FIG. 4J, or other profiles that are flat or curved as shown in FIG. 1M, for nonlimiting example. In the example of FIG. 4J, thickness A can have a range from about 50 microns to about 5 millimeter. In some embodiments, the thickness A is from 10 um to about 8 mm. In some embodiments, the thickness A is from 10 um to about 100 um. In some embodiments, the thickness A is from 30 um to about 200 um. In some embodiments, the thickness A is from 30 um to about 400 um. In some embodiments, the thickness A is from 50 um to about 1 mm. In some embodiments, the thickness A is from 100 um to about 3 mm. In some embodiments, the thickness A is from 200 um to about 6 mm.

FIGS. 4I-4L show an exemplary embodiments of the expandable skirt with uniform pattern and exemplary dimensions wherein, the thickness, A is 2 mm, the maximal width of an individual cell, S, or M, are about 5.18 mm or 7.60 mm, respectively. The height of an individual cell T or N is about 8.16 or 3.10 mm, respectively.

In some embodiments, the expandable skirt includes the foam cells 105 that can be arranged in a substantially uniform pattern in the protruding region 101*b* where the cells have a cross section along the radial direction of a triangle or substantially a triangle 114, as shown in FIG. 4H, or a rectangle or substantially rectangle as shown in FIG. 1F. The thickness, or dimension in the radial direction ranges from about 0 to A. The foam cell, in this embodiment, includes a height of C and a width of B. In this particular embodiment, A, B, and/or C can have a range from about 50 microns to about 5 millimeter. In some embodiments, A, B, and/or C is from 10 um to about 8 mm. In some embodiments, A, B, and/or C is from 10 um to about 100 um. In some embodiments, A, B, and/or C is from 30 um to about 200 um. In some embodiments, A, B, and/or C is from 30 um to about 400 um. In some embodiments, A, B, and/or C is from 50 um to about 1 mm. In some embodiments, A, B, and/or C is from 100 um to about 3 mm. In some embodiments, A, B, and/or C is from 200 um to about 6 mm.

Figure 1U:
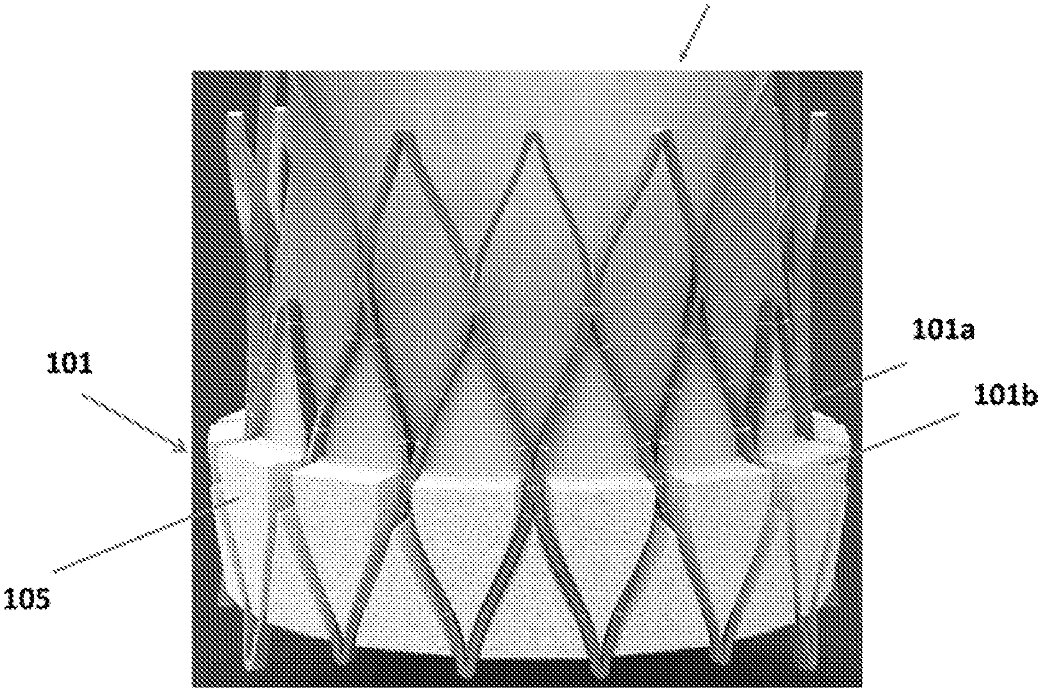
FIGS. 1U-1W show non-limiting exemplary embodiments of the expandable sealing skirt in a deployed state (alternatively referred to herein as an expanded sealing skirt or deployed sealing skirt, or sealing skirt) with a ACURATE® stent frame and valve.
Figure 1V:
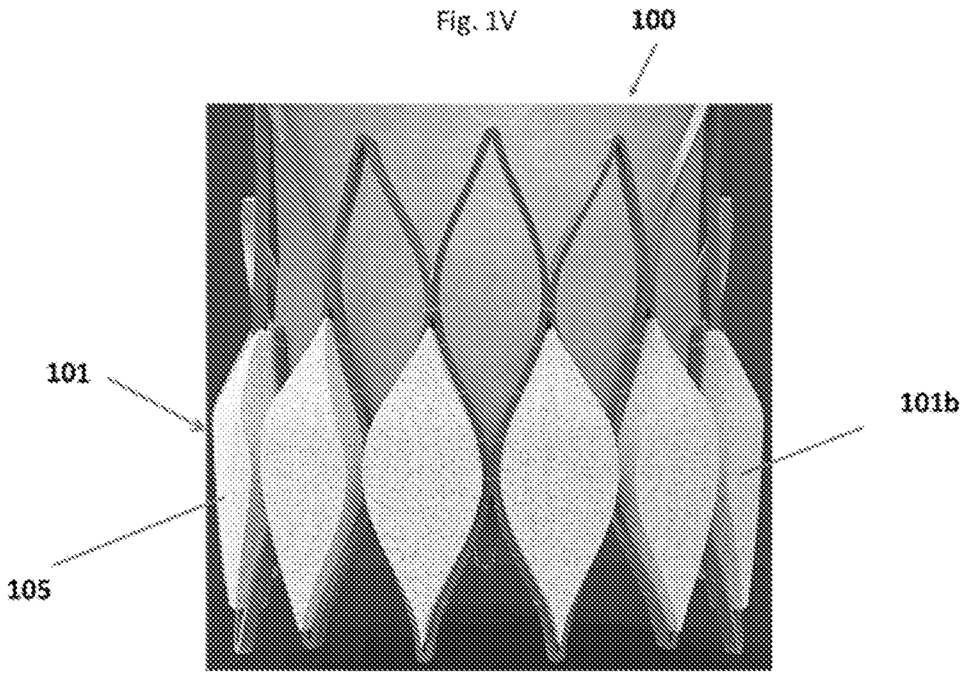
Figure 1W:
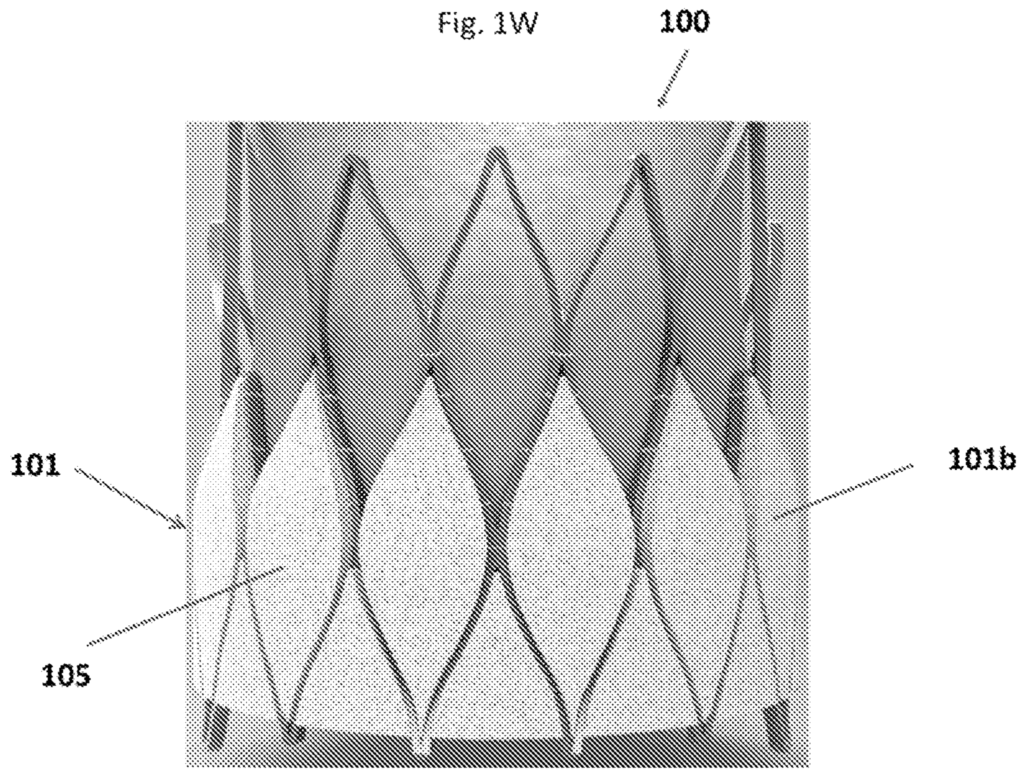

FIGS. 1Q-1W show exemplary embodiments of the expendable skirt with one or two layers or rings of protruding cells. Referring to FIG. 1V, the non-protruding region 101*b* has a single layer of protruding cells which are attached to the non-protruding region 101*a*. Each protruding cell includes a shape that is substantially diamond as its bottom surface if the stent were to cut along the longitudinal direction and laid flat and expanded. Referring to FIGS. 1Q, 1U, and IW, the non-protruding region 101*b* has two layer of protruding cells which are attached to the non-protruding region 101*a*. One or two layers of protruding cell includes a shape that is substantially triangular as its bottom surface if the stent were to cut along the longitudinal direction and laid flat and expanded. The substantially triangular shape may include a one or two sides that are slighted curved. In some embodiments, each layer or ring of protruding cells may include a uniform pattern, shape, or size as shown in FIG. 1Q. In some embodiments, one layer or ring of protruding cells may include a different size or shape as compared to another layer or ring of protruding cells. In this particular embodiment in FIG. 1U, the area of the bottom surface of the first layer of protruding cells toward the top portion is larger than the area of the bottom surface of the second layer of protruding cells. In the particular embodiment in FIG. 1W, both the area and the shape of the bottom surface of the first layer of protruding cells toward the top portion is different than those of the bottom surface of the second layer of protruding cells toward the bottom portion. The first layer of protruding cells can have a substantially diamond bottom surface and the second layer of protruding cells can have a substantially triangular bottom surface.

In the particular embodiment in FIGS. 1Q-1U, the protruding cell of one or more layers has approximately identical dimensions as the protruding cells in FIGS. 4M-4P.

In some embodiments, the expandable skirt includes the foam cells 105 that can be arranged in a non-uniform pattern along the longitudinal direction (as in FIG. 5J-5K) where the cells have a cross section along the radial direction of an approximate rectangle 114, as shown in FIG. 5L. In the particular embodiment shown in FIGS. 5I-5L, the protruding foam cells are arranged in two layers of substantially triangles (or substantially trapezoids) that conform to the stent cell arrangement. In this embodiment, the more proximal layer of cells is smaller and the distal layer of cells is much larger (in width and/or height). The thickness of a foam cell in the radial direction is A. The non-protruding region 101*a* extends more proximally than the protruding region 101*b*. The proximal edge of the non-protruding region can have a zig-zag profile as shown in FIG. 5J, or other profiles that are flat or curved. The thickness, or dimension in the z-direction/radial direction is A, which can have a range from 50 microns to 5 millimeter.

FIGS. 4M-4P shows an exemplary embodiment of the expendable skirt of uniform pattern. In this embodiment, the non-protruding region 101*b* has a single layer of protruding cells which are attached to the non-protruding region 101*a*. Each protruding cell includes a shape that is substantially a portion of a diamond with the distal tip (e.g., a small triangular tip) removed as its bottom surface if the stent were to cut along the longitudinal direction and laid flat and expanded. The bottom surface (when the skirt is cut along the longitudinal direction and laid flat, the surface touching the backing) is substantially triangular. In other embodiments, the bottom surface is substantially trapezoid.

In this embodiment, the gap, G, is about 1.11 mm, the thickness, A (FIG. 4P) is 2 mm, the width, M, of cells is about 4.49 mm, the inner wall 111 thickness (or thickness of the non-protruding region) is about 0.5-2.5 mm. The height of an individual cell N along the longitudinal direction is 6.42 mm at its bottom surface. The height of the backing supporting each individual cell along the longitudinal is 6.92 mm. In some embodiments, as shown in FIGS. 4M-4P, the height Q, 4.37 mm, is greater than R, 2.05 mm, while in some embodiments it is vice versa. The diameter D of the cross section in x-y plane is 26 mm.

FIGS. 5M-5P shows an exemplary embodiment of the expendable skirt of uniform pattern and exemplary dimensions of that are shown in FIGS. 8A-8D. In this embodiment, the non-protruding region 101*b* has two layers of protruding cells which are attached to the non-protruding region 101*a*. Each protruding cell of the most proximal layer includes a shape that is substantially a portion of a diamond with the distal tip (e.g., a small triangular tip) removed. Each protruding cell of the most distal layer includes a shape that is substantially a diamond. The bottom surface (when the skirt is cut along the longitudinal direction and laid flat, the surface touching the backing) is substantially triangular. In other embodiments, the bottom surface is substantially a trapezoid.

In this embodiment, the gap, G, is about 0.5 mm, the thickness, A (FIG. 8M) is 1.96 mm, the width, M, of cells of the most proximal layer is about 4.49 mm, the inner wall 111 thickness (or thickness of the non-protruding region) is about 0.5-2.5 mm. At the most proximal layer, the height of an individual cell N at the bottom surface along the longitudinal direction is 6.42 mm. The height of the backing supporting each individual cell along the longitudinal is 6.92 mm. In some embodiments, as shown in FIGS. 8M-8P, the height Q, 4.88 mm, is greater than R, 2.04 mm, while in some embodiments it is vice versa. At the most distal layer, the width S of each cell is about 4.03 mm, the height T at the bottom surface is about 6.03 mm, which is smaller than that of cells proximal to it. The diameter D of the cross section in x-y plane is 26 mm.

As shown in FIG. 5O, the protruding region includes two layers of protruding cells 105 that are offset from each other so that the most proximal vertex from one layer do not align with any proximal vertex from the other layer. The profile 114 of the protruding cells can be sloped (e.g., FIG. 5P). The profile 114 of the protruding cells can be flat. In some embodiments, the protruding cells has a shape that is smaller than that of the stent cell thus it only protrudes from a part of the stent cells (e.g., FIG. 1P, the stent cells are substantially diamond, but the foam cells are triangular shapes at its bottom surface that does not cover the proximal portion of the stent cells).

As used herein, with respect to the expandable stent cells and/or the protruding cells, a "triangular" shape is synonymous with "substantially triangular," "approximately triangular," or "generally triangular" and refers to a shape having three legs (or alternatively called struts, or alternatively called arms) and three inflections connecting the three legs. The "triangular" shape, in some embodiments, does not have three sides that are equal in length. In some embodiments, the "triangular" shape has two or three sides are equal in length.

As used herein, with respect to the expandable stent cells and/or the protruding cells, a "trapezoid" shape is synonymous with "substantially trapezoid," "approximately trapezoid," or "generally trapezoid" and refers to a shape having four legs (or alternatively called struts, or alternatively called arms) and four inflections. The "trapezoid" shape, in some embodiments, does not have three sides that are equal in length. In some embodiments, the "trapezoid" shape has two sides are equal in length.

FIGS. 8I-8L shows an exemplary embodiment of the expandable skirt with uniform pattern and exemplary dimensions of that shown in FIGS. 5I-5L. In this embodiment, the gap, G, is about 0.7 mm, the thickness A is about 2 mm, the maximal width of an individual cell, M, or S, is about 5.14 mm or 8.10 mm, respectively, the inner wall 111 thickness X is about 0.50 mm. The height of an individual cell N or T is about 3.10 or 3.76 mm, respectively.

In some embodiments, such as embodiment shown in FIGS. 1B, 1E, 1H, 1I, 1K, 1M, 4C, 4K-6C, the protruding region includes two layers of protruding cells 105 that offset from each other. The profile 114 of the protruding cells can be flat (e.g., FIGS. 4D-5D) or sloped. In some embodiments, the protruding cells share substantially the same shape of the stent cells each of them protrudes from. In some embodiments, the protruding cells has a shape that is smaller than that of the stent cell thus it only protrudes from a part of the stent cells, for example, as shown in FIGS. 1M and 4K, at least, in which the stent cells are pentagon shaped, but the foam cells are triangular shapes that only cover the distal tip of the stent cell.

FIGS. 4E-4G shows an expandable skirt with one layer of foam cells in a top view, a side view, and a perspective view, respectively. In this embodiment, the skirt is cut at the circumference and laid flat. In this embodiment, the layers of cells have a cross section 114 along the radial direction 107 shown FIG. 4H.

In some embodiments, the expandable skirt includes the foam cells 105 that can be arranged in a uniform pattern where the cells have a cross section (section Y-Y) profile of a diamond, 114, as shown in FIGS. 5A-5D. The thickness, or dimension in the z-direction/radial direction is A, which can have a range from 50 microns to 5 millimeter.

In some embodiments, the expandable skirt includes more than one layer of foam cells 105 that can be arranged in a uniform pattern in the protruding region 101*b*. FIGS. 5A-5P show embodiments of an expandable skirt with one to several layers of foam cells in a top view, a side view, and a perspective view, respectively. In such embodiments, the skirt is cut at the circumference and laid flat. In some embodiments, the layers of cells have a cross section 114 (section E-E) along the radial direction (Y-Y) profile of a diamond, 114, as shown FIGS. 5D and/or 5H, at least. In this and other embodiments, for each foam cell, either on the top layer or the bottom layer, the maximal thickness of radial cross section 114 occurs at a location more toward the bottom of each foam cell or the expandable skirt.

In some embodiments, the expandable skirt includes 2, 3, 4, 5, 6, or even more layers of foam cells. In some embodiments, the number of layers of foam cell is less than the number of layers of stent cells of the assemblies herein. The thickness, or dimension in the radial direction is A, which can have a range from 50 microns to 5 millimeter. The foam cell, in this embodiment, includes a height of M or T and a width of S or N. In this particular embodiment, A, M, N, S, and/or T can have a range from about 50 microns to about 5 millimeter. In some embodiments, A, M, N, S, and/or T is from 10 um to about 8 mm. In some embodiments, A, M, N, S, and/or T is from 10 um to about 100 um. In some embodiments, A, M, N, S, and/or T is from 30 um to about 200 um. In some embodiments, A, M, N, S, and/or T is from 30 um to about 400 um. In some embodiments, A, M, N, S, and/or T is from 50 um to about 1 mm. In some embodiments, A, M, N, S, and/or T is from 100 um to about 3 mm. In some embodiments, A, M, N, S, and/or T is from 200 um to about 6 mm. In some embodiments, the inner wall thickness is about 0.1 mm to about 1 mm. In some embodiments, the inner wall thickness is about 0.3 mm to about 0.6 mm. In some embodiments, the distance B or C from the point of maximal height A to the edge of the foam cell is in the range of about 10 um to about 8 mm. In some embodiments, the distance B or C is from 10 um to about 100 um. In some embodiments, the distance B or C is from 30 um to about 200 um. In some embodiments, the distance B or C is from 30 um to about 400 um. In some embodiments, the distance B or C is from 50 um to about 1 mm. In some embodiments, the distance B or C is from 100 um to about 3 mm. In some embodiments, the distance B or C is from 200 um to about 6 mm.

FIGS. 8A-8D shows an exemplary embodiment of the expandable skirt with uniform pattern and exemplary dimensions of that shown in FIGS. 5A-5D. In this embodiment, the gap, G, is about 0.25 mm, the thickness, A (FIG. 5D) is 1.97 mm, the width, Y, is about 4.39 mm, the inner wall 111 thickness is about 0.50 mm. The height of an individual cell along Y-Y is about 6.29 mm.

FIGS. 8E-8H shows an exemplary embodiment of the expandable skirt with uniform pattern and exemplary dimensions of that shown in FIGS. 5E-5H. In this embodiment, the gap, G, is about 0.3 mm, the maximal thickness, A (FIG. 5H) is 1.87 mm, the width, S, is about 6.79 mm for the top layer of cells and the width, N, is about 7.43 for the bottom layer of cells. The height of an individual cell along E-E is about 6.26 mm for the top layer of cells, and 5.72 for the bottom layer of cells.

FIG. 8M-8P shows an exemplary embodiment of the expandable skirt with uniform pattern and exemplary dimensions of that shown in FIG. 5M-5P. In this embodiment, the gap, G, is about 0.25 mm, the thickness, A (FIG. 5P) is 1.97 mm, the width, Y, is about 4.39 mm, the inner wall 111 thickness is about 0.50 mm. The height of an individual cell along Y-Y is about 6.29 mm.

As shown in FIGS. 4C and 5C, the protruding region includes two layers of protruding cells 105 that offset from each other so that the most proximal vertex from one layer do not align with any proximal vertex from the other layer. The profile 114 of the protruding cells can be flat (e.g., FIG. 4D) or sloped (e.g., FIG. 5D). In some embodiments, the protruding cells share substantially the same shape of the stent cells each of them protrudes from, e.g., diamond in FIG. 4C. In some embodiments, the protruding cells has a shape that is smaller than that of the stent cell thus it only protrudes from a part of the stent cells (e.g., FIG. 5C, the stent cells are diamond, but the foam cells are pentagon shapes that does not cover the distal tip of the stent cell).

As shown in FIG. 4G, the protruding region includes only one layer of protruding cells at the distal end of the stent frame, this layer of foam cells does not protrude from any layer of stent cells, but instead from the shape at least partly defined by the distal open ends of the stent frame. The nonprotruding region may include a flat proximal edge and a flat distal edge. As shown in FIGS. 1H and 5G, two layers of protruding cells 105 are arranged with offset. The profile 114 of the protruding cells can be flat or sloped (e.g., FIG. 5H). In some embodiments, the protruding cells share substantially the same shape of the stent cells each of them protrudes from. In some embodiments, the protruding cells has a shape that is smaller than that of the stent cell thus each cell only protrudes from a part of the stent cell (e.g., FIG. 5G, the stent cells are diamond, but the foam cells are triangle shapes that does not cover the proximal half of the stent cell).

In some embodiments, a skirt herein is sutured to the native pericardial tissue skirt in and/or native graft material (Polyethylene Terephthalate (PET)) skirt) using a "lap joint" such that it provides a hydrodynamic seal. In some embodiments, the compression force of expandable skirt is much less than the radial force of stent, as a result of which the complete expansion, and hence the radial force, of the stent is not affected. When the device with the expandable sealing skirt is deployed in an annulus against a portion that has no calcification, the lower compression force of the skirt compared to the outward radial force of the stent won't allow the stent to be pushed inward and ensure no reduction in the geometric or effective orifice area of the valve, or for example, 10 times, 20 times, 30 times, 40 times, 50 times, 60 times, 70 times, 80 times, 100 time, 200 times, 500 times, 1000, 1200 time, 1500 times, 1800 times, 2000 times, 2200 times, 2500 times, 2800 times, or 3000 times smaller, or 10 times, 20 times, 30 times, 40 times, 50 times, 60 times, 70 times, 80 times, 100 time, 200 times, 500 times, 1000, 1200 time, 1500 times, 1800 times, 2000 times, 2200 times, 2500 times, 2800 times, or 3000 times smaller. In some embodiments, the skirt includes materials with instantaneous compression characteristics thereby allowing complete recapturability of skirt along with other elements of the device assembly for withdrawal from the patient. In some embodiments, the skirt is compressible instantaneously within a time period of about 0.001 second to about 60 seconds. In some embodiments, the skirt is compressible instantaneously within a time period of about 0.01 second to about 10 seconds. In some embodiments, the skirt is compressible instantaneously within a time period of about 0.05 second to about 1 second. In some embodiments, the skirt is compressible instantaneously within a time period of about 0.05 second to about 0.5 seconds. In some embodiments, the skirt is compressible instantaneously within a time period of about 0.01 second to about 0.12 seconds. In some embodiments, the skirt is compressible instantaneously in a time period with a maximal time of about 0.04 seconds, about 0.05 seconds, about 0.06 seconds, about 0.08 seconds, about 0.1 seconds, about 0.15 seconds, about 0.2 seconds, or about 0.25 seconds. In some embodiments, the compression of the skirt is perceptively instantaneous. That is, the compression happens so quickly that it is effectively instantaneous in the ranges or timing disclosed herein. Thus, compression of the skirt occurs within the timing disclosed herein.

In some embodiments, the skirt is compressible instantaneously within a time period of 0.001 second to 60 seconds. In some embodiments, the skirt is compressible instantaneously within a time period of 0.01 second to 10 seconds. In some embodiments, the skirt is compressible instantaneously within a time period of 0.05 second to 1 second. In some embodiments, the skirt is compressible instantaneously within a time period of 0.05 second to 0.5 seconds. In some embodiments, the skirt is compressible instantaneously within a time period of 0.01 second to 0.12 seconds. In some embodiments, the skirt is compressible instantaneously in a time period with a maximal time of 0.04 seconds, 0.05 seconds, 0.06 seconds, 0.08 seconds, 0.09 seconds, 0.1 seconds, 0.12 seconds, 0.15 seconds, 0.2 seconds, or 0.25 seconds.

In some embodiments, the skirt is expandable, e.g., self-expansion or controlled expansion, when in the deployed configuration, within a time period of about 0.001 second to about 60 seconds. In some embodiments, the skirt is expandable within a time period of about 0.01 second to about 10 seconds. In some embodiments, the skirt is expandable within a time period of about 0.01 second to about 5 seconds. In some embodiments, the skirt is expandable within a time period with a maximal time of about 0.05 seconds, about 0.1 seconds, about 0.15 seconds, about 0.2 seconds, about 0.3 seconds, about 0.4 seconds, about 0.5 seconds, about 0.6 seconds, about 0.8 seconds, about 1 second, about 1.2 second, about 1.5 second, about 1.8 seconds, about 2 seconds, about 2.5 seconds, about 2.8 seconds, about 3 seconds, about 4 seconds, or about 5 seconds.

In some embodiments, the skirt is expandable, e.g., self-expansion or controlled expansion, when in the deployed configuration, within a time period of about 0.001 second to about 60 seconds. In some embodiments, the skirt is expandable within a time period of about 0.01 second to about 10 seconds. In some embodiments, the skirt is expandable within a time period of about 0.01 second to about 5 seconds. In some embodiments, the skirt is expandable within a time period with a maximal time of about 0.05 seconds, about 0.1 seconds, about 0.15 seconds, about 0.2 seconds, about 0.3 seconds, about 0.4 seconds, about 0.5 seconds, about 0.6 seconds, about 0.8 seconds, about 1 second, about 1.2 second, about 1.5 second, about 1.8 seconds, about 2 seconds, about 2.5 seconds, about 2.8 seconds, about 3 seconds, about 4 seconds, or about 5 seconds.

In some cases, the expandable skirts disclosed herein requires no change to the valve design, including leaflet design, leaflet suturing method/procedure, and/or attachment procedure/method of the valve to the stent frame. In some cases, the expandable skirts disclosed herein require no change to the stent frame. In some cases, the expandable skirts disclosed herein requires no change to delivery of the valve and/or stent frame technique/procedure within the patient and conventional manufacturing techniques (standard suturing) for assembling expandable skirts onto stent frame. In some embodiments, a skirt herein is compatible with conventional surgical sutures. In some embodiments, the expandable skirts herein are configured to "bolt-on" to existing TAVI devices.

In some embodiments, the skirt is a foam skirt. The materials used for the skirt can include but is not limited to the following biocompatible and biostable materials, such as, PET, silicones, polyurethanes, PEEK, PTFE, nylon, PP, PE (LD/HDPE), polyamide, polyester, among others [need help with preparing exhaustive list, if deemed necessary]. In some embodiments, the skirt includes foam or other porous and/or expandable materials. In some embodiments, the skirt can be designed to have reinforced materials 108. Such reinforcement materials can include PET membrane or other meshes/membranes that may be fully integrated with the foam skirt, for example, on the luminal wall 111. In some embodiments, the reinforcement materials can be used to achieve any desired functionality such as increased tensile strength, and/or compatibility with suturing (increased tear strength).

In some embodiments, skirt can be integrated with the stent such that there is no suturing necessary. In some embodiments, radio-opaque markers can be included/integrated as part of the skirt, optionally as part of the protruding materials of the skirt.

In some embodiments, the relative position of the skirt to the stent frame, valve, and/or native skirt may be altered for different applications. In some embodiments, the skirt may be positioned at the top 110, middle 120, or bottom 130 portion of the stent frame along the z direction. In some embodiments, the middle portion includes the region with the smallest cross section in the x-y plane. In some embodiments, the top portion 110 is or includes the flared section of the stent frame. In some embodiments, the bottom portion 130 is or includes the substantially columnar section (as shown in FIG. 1H), conical section or generally conical section (as shown in FIG. 1A) of the stent frame. In some embodiments, the middle portion 120 is or includes a constricted region of the stent frame. In some embodiments, the flared section and the substantially columnar section are connected without a constricted region therebetween (as shown in FIG. 1H). In some embodiments, connectors (e.g., 131*a*, 131*b* in FIG. 1J) herein are in the constricted region or between the flared section and the substantially columnar section. In some embodiments, the connectors (e.g., 130*a* in FIG. 1J) are in the substantially columnar section and/or the constricted region of the stent frame. In some embodiments, the skirt could be either positioned above or below the tissue/native skirt, to suit transfemoral or transapical delivery of the device assembly. The skirt can be attached solely to the stent, solely to the native skirt, solely to the valve, or to a combination thereof. In some embodiments, the contours of the skirt are designed such that during loading the stent struts do not cut/damage the protruding cells of the skirt.

In some embodiments, the stent along with the skirt can be used as an independent cuff that is used as a sealing dock for other valves (or other endovascular devices such as stent grafts). In some embodiments, this cuff has a "temporary valve" that functions for sufficient cycle until another valve is deployed within.

In some embodiments, the skirt can have growth factors induced to allow for tissue in-growth (optionally between the vessel wall and the skirt) when against the vessel wall thereby achieving enhanced sealing over a period of time. In some embodiments, the surfaces of the skirt are made non-thrombogenic by providing a non-thrombogenic coating (using plasma, etc.).

In some embodiments, the expansion rate of the foam of the skirt can be controlled. In some embodiments, the expansion rate of the foam of the skirt can be controlled by using expandable material(s) with desired expansion rate. In some embodiments, the skirt is fully expanded after moving out of the enclosing catheter in the range of about 0.1 s to about 3 hours. In some embodiments, the skirt is fully expanded after moving out of the enclosing catheter in the range of about 1 s to about 30 minutes. In some embodiments, the expansion of the skirt is perceptively instantaneous. That is, the expansion happens so quickly that it is effectively instantaneous within the ranges or timing disclosed herein. Thus, expansion of the skirt occurs within the timing disclosed herein. In some embodiments, the expansion level of the skirt may be variable when it is properly deployed or fully expanded. For example, the skirt may be compressed by a local calcification spot so that the expansion level of the skirt against the calcification is lower than that against the flat inner vessel wall—the expansion level of the skirt will be higher where there are gaps due to the non-conformance of the stent to the annulus while the expansion level will be low or nil when the skirt is butted against a calcification or against the section of the annulus where there is no calcification. In some embodiments, the expandable skirts herein advantageously allows up to 30× volumetric expansion capability (expanded vs. compressed state) and enable crimping conventional valve sizes (e.g. 20, 23, 26, up to 30 mm) within 18F (or lower) profile and effective sealing of highly calcified annulus. In some embodiments, such high volumetric expansion capability allows for outward extension of the skirt (the described protruding region) by up to approximately 5 mm radially outward from the stent frame thereby providing enhanced sealing in highly calcified annuli, where the paravalvular leak sites are large.

In some embodiments, the luminal layer 111 of the skirt is assembled (using sutures) such that it remains "taut" after the deployment of the valve in the annulus thereby minimizing any inward extension/folding of the skirt and therefore maximizing the effective orifice area.

In some embodiments, the assembly of the skirt on the valve may be performed in a manner such that the skirt is undersized during assembly—in other words, the skirt may be pre-stretched during the assembly process. In order to do this, material with some degree of elasticity may be used to be integrated within the foam (e.g. a replacement for the PET graft material).

Referring to FIGS. 2A-2D, in a particular embodiment, the expandable skirt 101 includes the foam is in the form of a strip 814. The strip may be segmented along its length (x-y direction). In this embodiment, the strip has an amplitude along the longitudinal direction, as shown in FIG. 2D as a. In some embodiments, a can be 0 mm, in which case the strip is lying in a single x-y plane. In some embodiments, the amplitude can be anywhere from 0 mm to 20 mm. The spreading along the longitudinal length of the device, that gives the skirt a "wave" like pattern/shape as shown in FIG. 2D, allows for minimizing device profile by reducing the mass density across the longitudinal section/plane of the device. The height of the skirt is h, as shown in FIG. 2D. As can be seen from FIG. 2A-2C, the protruding region 801*b* spans in the longitudinal direction across the amplitude a. In some embodiments, there is an additional skin 801*c* to further encapsulate the 801*b* protruding region with a thickness (along the radial direction) of 1 nanometer to 10 micrometers to increase the structural integrity of the foam expandable skirt, minimize any risk with thrombosis. The non-protruding section of the skirt 801*a* is attached to the exterior of the stent, or both. In some embodiments, the exterior of the stent includes the surface of the stent adjacent to the vessel wall. In some embodiments, the luminal/inner wall of the skirt 811 is attached to the outer wall of the stent, and the outer wall of the skirt 812 opposes the vessel wall. In this embodiment, the height of the strip is shown by h in FIG. 2D. In some embodiments, such height ranges from 50 micrometer to 15 millimeters—preferably in the range of 0.5 millimeter to 5 millimeters. In some embodiments, the protruding portion of the skirt 814 can have a range of cross section profiles 114 (e.g. such as cross section C-C in FIG. 4D, and/or cross section D-D in FIG. 6D), including but not limited to a triangle, a square, an oval, a trapezoid, a partial oval, a rhomboid, a random shape, a diamond, a partial diamond, a hexagonal, a partially hexagonal, a concave hexagonal, or a sloped shape comprising a narrower portion of the protruding cell toward a top end (proximal) of skirt along the z-direction or longitudinal direction, and comprising a wider portion of the protruding cell toward a bottom end (distal). In some embodiments, the strip includes segments along its length. In some embodiments, the strip is segmented into a number of cells along its length, to potentially allow for easier loading and deployment purposes. In this particular embodiment in FIGS. 2A-2D, the non-protruding section of the skirt 801*a* is attached to the luminal portion of the stent. In some embodiments, the expansion rate of the foam strip or the skirt can be controlled to be in a specified range. In some embodiments, the expansion rate of the foam strip or the skirt and can vary from less than a second to up to 30 minutes.

In Vitro Hydrodynamic Testing Results

In some embodiments, in vitro hydrodynamic testing is performed with the expandable skirt as disclosed herein. In a particular embodiment, the testing is at a mean arterial pressure (MAP) of 100 mm Hg with a heart rate of 72 beat per minute to simulate an in vivo condition of the skirt within a patient. In this embodiment, the test is averaged over 100 cycles. In this particular embodiment, regurgitation fraction of the valve in non-calcified annulus, with pericardial tissue skirt is about 17.4% which increases to 31.9% with calcified annulus. In the same embodiment, regurgitation fraction of the valve in calcified annulus, with the expandable skirt herein is about 18.1%, which is significantly lower than that with the pericardial tissue skirt. The significant reduction in regurgitation fraction may indicate a significantly improved sealing of the annulus of the vessel with the expandable skirt herein than the tissue skirt. The expandable skirt can have the potential to restore the hydrodynamic performance, regurgitation fraction, in particular, of a valve in a heavily calcified annulus to that of a valve with a pericardial tissue skirt as in a non-calcified annulus. In this embodiment, the calcified annulus has a cross-section simulating commissural calcification.

In some embodiments, the expandable skirt 101 herein seals the annulus with calcification by virtue of expansion and in effect pressing its outer wall 112 against the inner wall of the vessel. In the same embodiment, the tissue skirt does not effectively seal the annulus to a same degree as the expandable skirt herein.

In some embodiments, the expandable skirt 101 herein effectively seals the annulus with different levels and different distributions of calcification by expansion pressing its outer wall 112 against the inner vessel wall thereby preventing blood leakage along the longitudinal or z direction. In the same embodiments, the traditional tissue skirt without the expandable sealing skirt does not effectively seal the annulus to a same degree as the expandable skirt herein.

In some embodiments, in vitro hydrostatic testing is performed with the expandable skirt as disclosed herein. In a particular embodiment, the testing is at a mean back pressure of 100 mmHg that simulates a mean aortic pressure of 100 mmHg. In this embodiment, the regurgitation fraction of the valve in four calcified annuli with different calcification levels is examined. In this embodiment, the expandable skirt disclosed herein enables a much smaller regurgitation volume in all four test models with different calcification levels when compared with traditional tissue skirt. In this embodiment, the regurgitant volume is significantly decreased from 20.3 ml to 8.8 ml, from 16.0 ml to 7.8 ml, from 15.6 ml to 8.0 ml, and from 21.1 ml to 9.6 ml in these four different test models. In particular embodiments, the results demonstrate the potential that using the expandable skirt technology can normalize the hydrodynamic performance, regurgitation fraction in particular, across a wide range of patients having varied calcification, and make it equivalent to the baseline case i.e. a valve within a clean, non-calcified annulus.

In some embodiments, the expandable skirt disclosed herein has a similar recapturability as traditional pericardial tissue skirt. In some embodiments, the maximal reloading force required to recapture the expandable skirt is similar to the conventional loading forces experienced in a catheter of size 16 French inner diameter. In some embodiment, a catheter that has an inner diameter of a little less than 16 French is used.

In some embodiments, the expandable skirt disclosed herein has a similar migration force to a traditional pericardial tissue skirt. In a particular embodiment, the migration force of the device with the expandable skirt is similar to the device with a pericardial tissue skirt when tested under similar operating conditions that are clinically relevant ($p=0.31$).

In some embodiments, the expandable skirt disclosed herein provides compatibility with chemical sterilization and storage in glutaraldehyde solution. In a particular embodiment, there has been statistically significant change in the strength (e.g., maximal force) of the foam samples for making the expandable skirt herein up to two months when stored in glutaraldehyde solution—their strength remains at par with samples stored in phosphate buffered saline (PBS) demonstrating compatibility with glutaraldehyde solution. In some embodiments, the expandable skirt is compatible with other sterilization means, such as radiation sterilization and ethylene oxide sterilization.

Stents

Disclosed herein, in certain embodiments, are expandable stent frames 102 that the expandable skirt can be attached thereto. In some embodiments, the stent frame provides a scaffold for the expandable sealing skirt herein. In some embodiments, the stent frame includes one or more cells formed by its intersecting struts (alternatively called legs or edges or arms herein), the struts optionally zig-zag or intersect. In some embodiments, the cells are contoured and closed by the struts. In some embodiments, each closed or contoured stent cell include four vertices (alternatively referred to as inflections or inflection points). In some embodiments, adjacent stent cells share one or two vertices (alternatively referred to as inflections or inflection points). In some embodiments, two struts are attached at a vertex. In some embodiments, the attached struts remain attached when properly compressed or deployed. In some embodiments, the protruding cells of the expandable skirt has pre-formed shapes and sizes that conforms with the shapes and sizes of stent cells so that each protruding cells can protrude through a stent cell radially toward a vessel wall when the expandable skirt is deployed.

General Example

In some embodiments, the stent frame herein includes a distal end (bottom end) and a proximal end (top end) and two or three portioned therebetween. The two or three portions can include a top portion near the top end, and a bottom portion near the bottom end. There may be another middle portion connecting the top and bottom portions. One or more portions may be conical, cylindrical, reverse conical, flare or restricted along the longitudinal direction. In some embodiments, the stent frame has multiple struts that form one or more layers of stent cells stacked along the longitudinal direction, optionally in a staggered pattern. In some embodiments, the stent frame includes one, two, three, four, five, or even more layers of stent cells. In some embodiments, each layer of stent cells includes a uniform cell shape. In some embodiments, each layer includes at least two, or three different cell types. In some embodiments, the stent cells are of various shapes when laid flat in a two dimensional plane. Nonlimiting examples of the shapes include: substantially triangle, substantially diamond, substantially cubical, substantially rectangular, substantially pentagon, substantially hexagon, substantially concave hexagon, substantially chevron, substantially trapezoid, substantially oval, substantially circular, or substantially part of the geometrical shapes mentioned herein. In some embodiments, one or more stent cells herein include more than vertices (inflections) or otherwise connections between two connection struts. In some embodiments, such connections may be of a substantially U-shape or any other various shapes. In some embodiments, such connections remain connected in both the expanded deployed configuration and contracted delivery configuration.

In some embodiments, each stent cell includes a height, when deployed and laid flat, in the range of 5 mm to about 20 mm. In some embodiments, each stent cell includes a height, when deployed and laid flat, in the range of 20 mm to about 45 mm. In some embodiments, each stent cell includes a height, when deployed and laid flat, in the range of 10 mm to about 30 mm. In some embodiments, each stent cell includes a height, when deployed and laid flat, in the range of 5 mm to about 15 mm. In some embodiments, each stent cell includes a height, when deployed and laid flat, in the range of 15 mm to about 25 mm. In some embodiments, each stent cell includes a height, when deployed and laid flat, in the range of 25 mm to about 35 mm. In some embodiments, each stent cell includes a height, when deployed and laid flat, in the range of 35 mm to about 45 mm.

In some embodiments, the stent frame includes a height, when deployed and laid flat, in the range of 15 mm to about 40 mm. In some embodiments, the stent frame includes a height, when deployed and laid flat, in the range of 40 mm to about 80 mm. In some embodiments, the stent frame includes a height, when deployed and laid flat, in the range of 15 mm to about 40 mm. In some embodiments, the stent frame includes a height, when deployed and laid flat, in the range of 15 mm to about 35 mm. In some embodiments, the stent frame includes a height, when deployed and laid flat, in the range of 20 mm to about 30 mm. In some embodiments, the stent frame includes a height, when deployed and laid flat, in the range of 20 mm to about 35 mm. In some embodiments, the stent frame includes a height, when deployed and laid flat, in the range of 20 mm to about 40 mm. In some embodiments, the stent frame includes a height, when deployed and laid flat, in the range of 25 mm to about 35 mm. In some embodiments, the stent frame includes a height, when deployed and laid flat, in the range of 25 mm to about 40 mm. In some embodiments, the stent frame includes a height, when deployed and laid flat, in the range of 30 mm to about 40 mm. In some embodiments, the stent frame includes a height, when deployed and laid flat, in the range of 30 mm to about 50 mm. In some embodiments, the stent frame includes a height, when deployed and laid flat, in the range of 30 mm to about 60 mm. In some embodiments, the stent frame includes a height, when deployed and laid flat, in the range of 40 mm to about 60 mm.

In some embodiments, the stent frame includes a diameter, when deployed and laid flat, in the range of 15 mm to about 45 mm. In some embodiments, the stent frame includes a diameter, when deployed and laid flat, in the range of 20 mm to about 40 mm. In some embodiments, the stent frame includes a diameter, when deployed and laid flat, in the range of 15 mm to about 40 mm. In some embodiments, the stent frame includes a diameter, when deployed and laid flat, in the range of 20 mm to about 45 mm.

In some embodiments, the stent frame may include some supporting beam or connectors within or between different layers or different portions of the stent cells. In some embodiments, such supporting beams or connectors may be longitudinally extending and straight. In some embodiments, the supporting beams or connectors may include attachment structures such as loops or holes for allowing attachment of the valve and/or skirt to the stent frame. In some embodiments, such supporting beams or connectors are not expandable, thus are of a fixed length in the longitudinal direction. In some embodiments, such supporting beams or connectors are not expandable and are not as flexible as the rest of the stent frame. In some embodiments, such supporting beams or connectors are rigid.

In some embodiments, the stent frame includes open ends distal to the most distal layer of stent cells. For example, the open ends may extend from one or more distalmost vertices of the stent cells at the most distal layer and further extend distally, optionally in the longitudinal direction. In some embodiments, the open ends may be optional, and may be added to any existing stent frame with or without existing open ends. Similarly, the stent frame may include open ends to the most proximal layer of stent cells in similar manner as the distal end.

In some embodiments, such open ends may form at least partly geometrical shapes distal to the most distal layer of stent cells. Such shapes may be different or identical to the shape(s) of the stent cells. Nonlimiting examples of the shapes that may be formed at least partly by the open ends include: substantially triangle and substantially pentagon. In some embodiments, the expandable sealing skirt may include expandable foam cells that conform to at least part of the shapes that formed at least partly by such open ends.

Figures 3A, 3B, 3C, 3D:
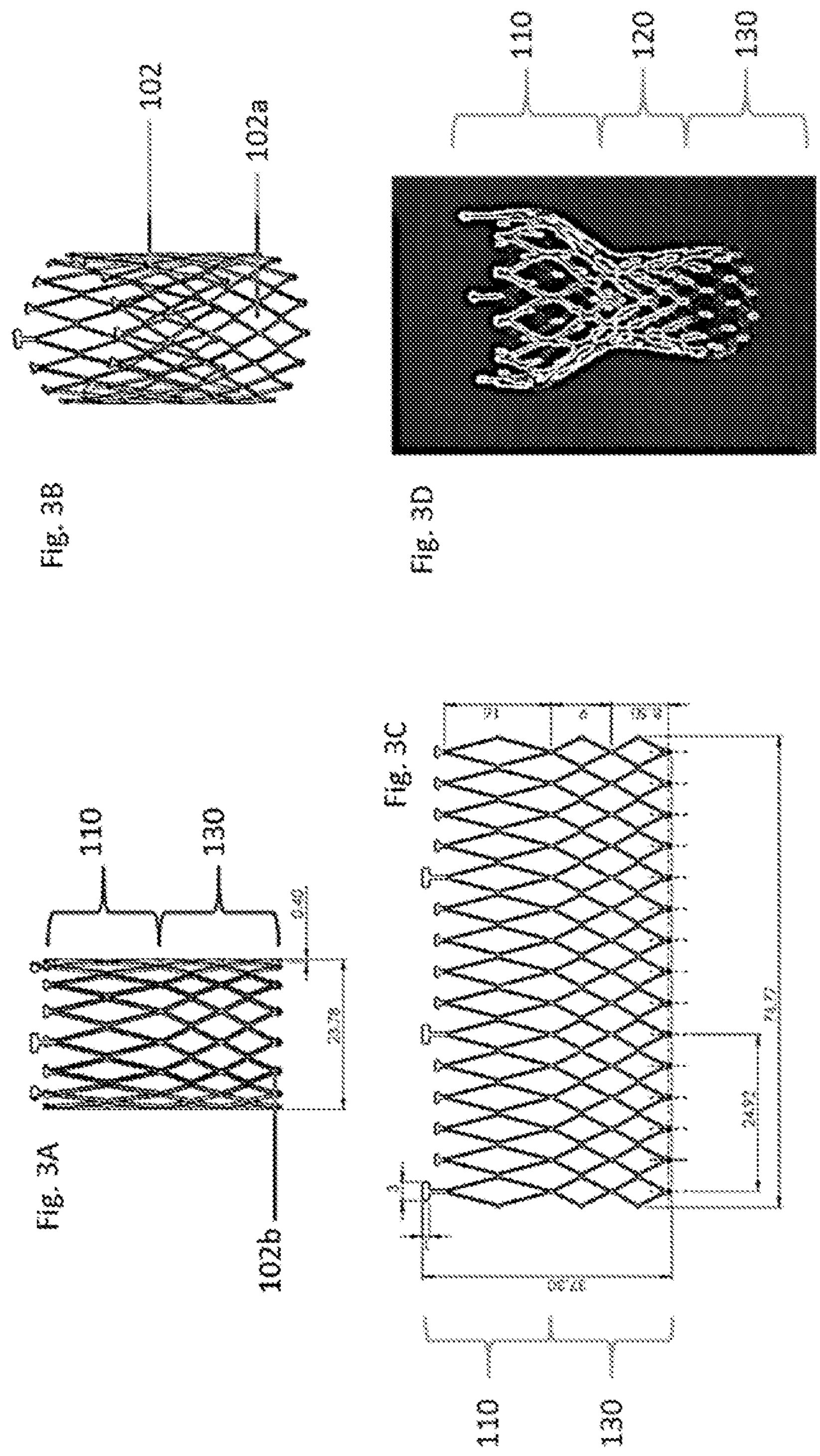
FIGS. 3A-3D show a non-limiting exemplary embodiment of the COREVALVE® stent shown in different views that can be used with the expandable sealing skirt.

COREVALVE® Example:

FIGS. 3A to 3D show nonlimiting exemplary embodiments of the stent frame herein with different views when the stent frame is expanded. In some embodiments, the stent includes one or more portions along the longitudinal direction or z axis. FIG. 3A shows the stent frame with the top 110 and bottom 130 portions. FIG. 3D shows the stent frame with the top 110, mid 120, and 130 bottom portions. Referring to FIG. 1G, in some embodiments, the top portion 110 is the most proximal portion while the bottom portion 130 is the most distal portion when the stent frame is properly implanted. In some embodiments, the distal portion is closer to the ventricle than the proximal portion. In some embodiments, the top portion 110 is or includes the flared section. In some embodiments, the bottom portion 130 is or includes the conical section or the generally conical section. In some embodiments, the bottom portion 120 includes the constricted region.

In some embodiments, the stent frame 102 includes one or more layers of stent cells 102*a* stacking along the longitudinal axis or z axis. In some embodiments, the stent cells on the same layer can be identical or different to each other in shape in the deployed configuration. In some embodiments, adjacent stent cells of the same layer share one or only one vertex (alternatively called inflections or inflection points). In some embodiments, adjacent stent cells of the same layer share two or only two vertices (alternatively called inflections or inflection points). In some embodiments, adjacent stent cells of the same layer share one vertex (alternatively called inflection or inflection point) and an edge (alternatively called a strut or leg herein). In some embodiments, adjacent stent cells of two different adjacent layers share two vertices and an edge.

In some embodiments, the adjacent stent cells shares at least a vertex or an edge. In some embodiments, the adjacent cells are not separated by any other stent cells therebetween. In some embodiments, the adjacent cells are separated by struts that are not part of the adjacent stent cells. In some embodiments, the adjacent layers are layers of the stent cells and the stent cells from adjacent layers share at least a vertex or an edge. In some embodiments, the adjacent layers are separated by struts that are not part of stent cells of the adjacent layers. In some embodiments, the stent cell is of various geometrical shapes. In addition to the closed or contoured cells, in some embodiments, the stent frame includes a layer of open ends proximal to the most proximal layer of closed stent cells. In some embodiments, the stent frame includes a layer of open ends distal to the most distal layer of closed stent cells. When connecting two adjacent open ends, a shape may be formed with the struts from the struts of adjacent stent cells. In some embodiments, this shape is different from that of the closed or contoured stent cells. Referring to FIGS. 3A-3C, the stent frame includes 5 layers of closed stent cells and the stent cells are of a substantially diamond shape. In some embodiments, the substantially diamond shape includes four legs (in two parallel pairs) that have inflections therebetween. The connecting legs extend from one inflection to the next inflection in a general direction that is parallel to its parallel pair, but is curved rather than straight—when laid flat in the expanded deployed configuration, thus the shape formed by the four legs are referred to as substantially diamond shape or diamond shape herein. Substantially diamond shape or diamond shape may also refer to true diamond shapes having straight edges and two pairs of edges or legs and within each pair there the edges or legs are parallel. The height of the stent cells from the proximal-most inflection to the distal-most inflection decreases gradually from the top portion (proximal) to the bottom portion (distal) of the stent frame. In some embodiments, the stent frame has a height of about 37.3 mm, the top layer of stent cells has a height of about 16 mm, and the bottom layer of stem cells includes a height of about 8.5 mm. The diameter of the stent cross section (perpendicular to z axis or longitudinal direction) is about 23.78 mm, and the strut includes a thickness of about 0.4 mm along the radial direction.

In some embodiments, the dimensions of the stent frame 102 and stent cells 102*a* are when the stent frame is in the deployed configuration. In some embodiments, the stent frame includes a height in the range of about 35 to 70 mm. In some embodiments, the stent frame includes a height in the range of about 30 to 65. In some embodiments, the stent frame includes a height in the range of about 25 to 65 mm or 25 to 65 mm. In some embodiments, the stent frame includes a height in the range of about 30 to 40 mm or 25 to 65 mm. In some embodiments, the stent includes a cross section (perpendicular to z axis or longitudinal direction) with a diameter of about 20 mm to about 30 mm. In some embodiments, the stent includes a cross section (perpendicular to z axis or longitudinal direction) with a diameter of about 25 mm to about 35 mm in an expanded deployed configuration, optionally measured at the distal end of the stent frame or proximal end of the stent frame. In some embodiments, the stent includes a cross section (perpendicular to z axis or longitudinal direction) with a diameter of about 25 mm to about 40 mm in an expanded deployed configuration, optionally measured at the distal end of the stent frame or proximal end of the stent frame. In some embodiments, the stent frame includes a cross section that is larger at the top portion than that at the bottom or mid portions, as shown in FIG. 3D. In some embodiments, the stent frame includes an approximately cylindrical shape as shown in FIGS. 3A-3B. In some embodiments, each stent cell includes a height of about 5 mm to about 20 mm in an expanded deployed configuration. In some embodiments, each stent cell includes a height of about 6 mm to about 9 mm in an expanded deployed configuration. In some embodiments, each stent cell includes a height of about 8 mm to about 10 mm in an expanded deployed configuration. In some embodiments, each stent cell includes a height of about 14 mm to about 18 mm in an expanded deployed configuration.

In some embodiments, the stent frame includes a collapsed delivery configuration and an expanded deployed configuration, wherein the stent frame comprises a conical section (or a generally conical section), a flared section, and a constriction region between the conical section and the flared section. In some embodiments, the stent frame comprises multiple stent cells which have a cell pattern defined by unequal length zig-zagging struts that connect in closed cells at inflection points to adjacent zig-zagging struts. The inflection points may not be true connections but may be laser cut to form this pattern of legs and inflections forming substantially diamond shaped cells. In some embodiments, one, two, or more layers of stent cells are of a substantially diamond shape. In some embodiments, the conical section or generally conical section is more distal to the flared section.

In some embodiments, the stent frame includes a collapsed delivery configuration and an expanded deployed configuration, wherein the stent frame comprises a conical section (or generally conical section). In some embodiments, the stent frame includes a generally conical section and a flared section which are connected to each other. In some embodiments, the generally conical section is more distal to the flared section.

Figure 3E:
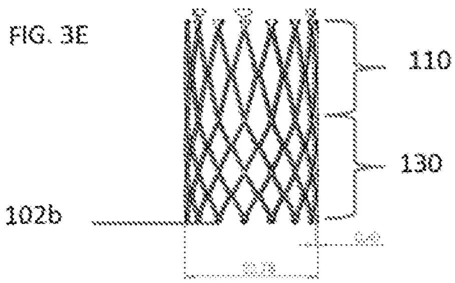
FIGS. 3E-3J show a non-limiting exemplary embodiment of the PORTICO® stent shown in different views that can be used with the expandable sealing skirt.
Figure 3F:
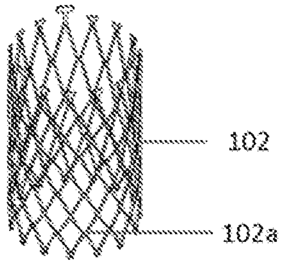
Figure 3G:
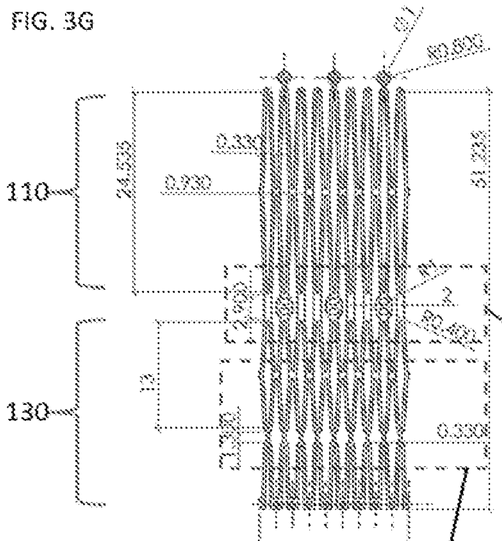
Figure 3H:
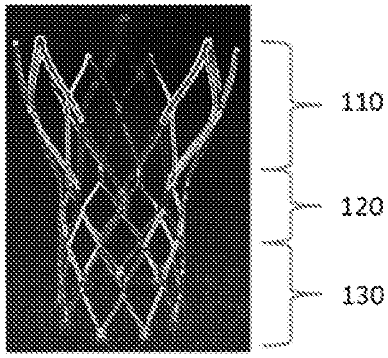
Figure 3I:
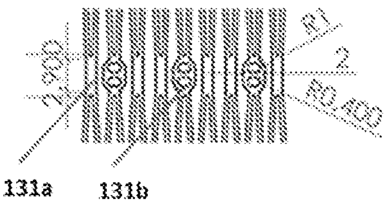
Figure 3J:
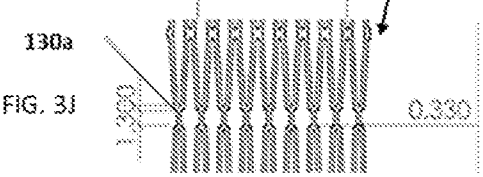
Figure 3K:
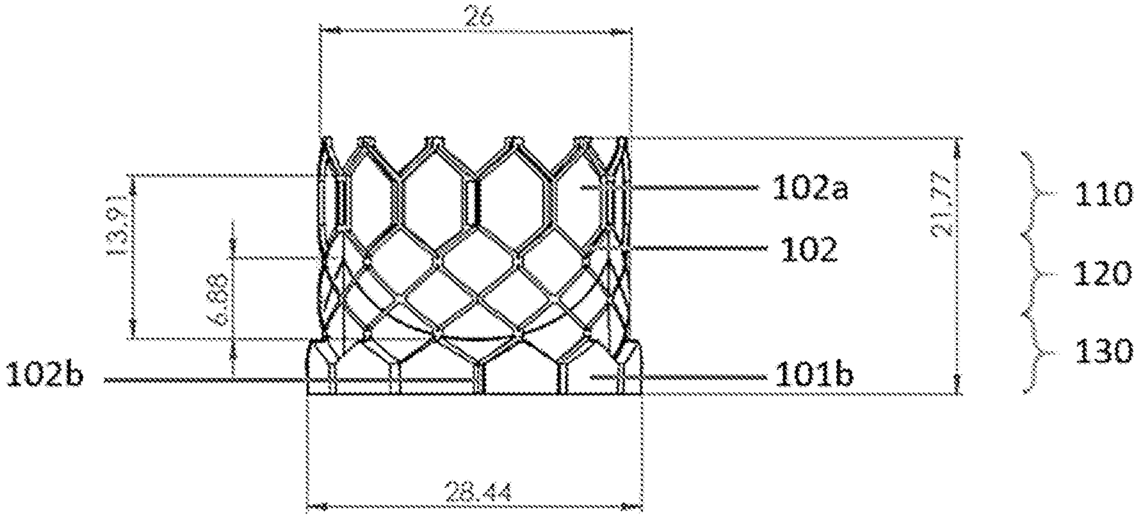
FIGS. 3K-3L show a non-limiting exemplary embodiment of a SAPIEN® stent frame along with an expandable sealing skirt assembled thereon in a side view (FIG. 3K) and a top view (FIG. 3L)
Figure 3L:
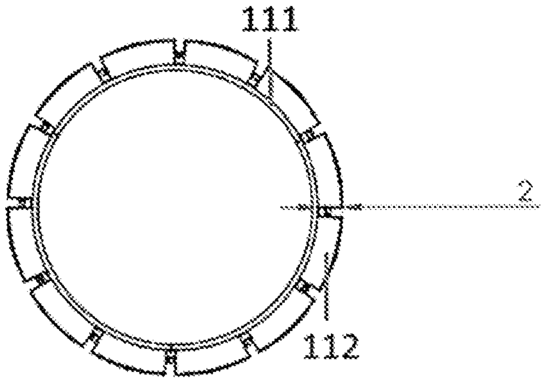

PORTICO® Example:

FIGS. 3E to 3J show nonlimiting exemplary embodiments of the stent frame herein with different views when the stent frame is expanded. In some embodiments, the stent includes one or more portions along the longitudinal direction or z axis. FIGS. 3E-3G show the stent frame with the top 110 and bottom 130 portions either connected to each other directly (FIG. 3A) or connected to each other view connectors 131*a*, 131*b* (FIG. 3I). In some embodiments, the top portion is flared. In some embodiments, the bottom portion is substantially columnar. In some embodiments, the connector may be one or more struts connecting the most distal end of the top portion at the distal vertices of the most distal layer of stent cells in the top portion 131*a* and the most proximal end of the bottom portion at the proximal vertices of the most proximal layer of stent cells in the bottom portion. In some embodiments, the strut(s) may be straight, curved, or their combinations. In some embodiments, the height of the connector 131*a*, 131*b* is much less than the height of the top portion or the bottom portion. In some embodiments, the connector is different from the attachment between two vertices within a single portion of the stent frame. Referring to FIGS. 3G and 3I, in a particular embodiment, the connector has a height of about 2.9 mm. In this embodiment, the connector includes not only straight struts 131*a* but also struts with loop and hole structures 131*b*. Also in this embodiment, the bottom portion include a second connector 130*a* in the form of a straight strut connecting two vertices, each vertex from a different stent cell as shown in FIG. 3J, thus, these two vertices from two adjacent layers are not connected or attached directly to each other. Although FIGS. 3G, 3E-3J show the stent frame in a deployed or undeployed state only, the connections and attachments of the struts, vertices remain unaltered when the stent frame is compressed or deployed. In some embodiments, the connector enables attachment of the skirt and/or valve to the stent frame (FIGS. 1I and 1J).

In some embodiments, the top and bottom FIG. 3H shows the stent frame with the top 110, mid 120, and 130 bottom portions. Referring to FIG. 1G, in some embodiments, the top portion 110 is the most proximal portion while the bottom portion 130 is the most distal portion when the stent frame is properly implanted. In some embodiments, the distal portion is closer to the ventricle than the proximal portion.

In some embodiments, the stent frame 102 includes one or more layers of stent cells 102*a* stacking along the longitudinal axis or z axis. In some embodiments, the stent frame includes 2, 3, 4, 5, 6, or even more layers of closed stent cells. In some embodiments, the stent frame includes 1 or 2 layers of open stent cells at the distal and/or proximal end. In some embodiments, the stent cells on the same layer can be identical or different in shape, size, or both to each other. In some embodiments, the stent cell is of various geometrical shapes at different layers. In some embodiments, adjacent stent cells of the same layer share one or only one vertex. In some embodiments, adjacent stent cells of the same layer share two or only two vertices. In some embodiments, adjacent stent cells of the same layer share one vertex and an edge. In some embodiments, adjacent stent cells of two different adjacent layers share two vertices and an edge.

In some embodiments, the adjacent stent cells shares at least a vertex or an edge. In some embodiments, the adjacent cells are not separated by any other stent cells therebetween. In some embodiments, the adjacent cells are separated by struts that are not part of the adjacent stent cells. In some embodiments, the adjacent layers are layers that the stent cells from them shares at least a vertex or an edge. In some embodiments, the adjacent layers are separated by struts that are not part of stent cells of the adjacent layers. In some embodiments, the stent cell is of various geometrical shapes. In addition to the closed or contoured cells, in some embodiments, the stent frame includes a layer of open ends proximal to the most proximal layer of closed stent cells. In some embodiments, the stent frame includes a layer of open ends distal to the most distal layer of closed stent cells. When connecting two adjacent open ends, a shape may be formed with the struts from the struts of adjacent stent cells. In some embodiments, this shape is different from that of the closed or contoured stent cells. Referring to FIGS. 3E-3H, the stent frame includes 4 or 5 layers of stent cells. In this embodiment, the height of the stent cells decreases gradually from the top portion to the bottom portion of the stent frame. In some embodiments, the stent frame has a height of about 51 mm, the top layer of stent cell has a height of about 24.5 mm while the bottom layer of stem cells includes a height of about 20 mm. The diameter of the stent cross section (perpendicular to z axis or longitudinal direction) is about 23.78 mm or 18.8 mm, and the strut includes a thickness of about 0.4 mm along the radial direction. In this embodiment, a stent cell in the bottom portion has a height of about 13 mm while the stent cell of the most proximal layer has a height of about 24.5 mm. In some embodiments, the stent cells are of an approximate diamond shape. In some embodiments, the stent cells are of an approximate hexagon shape (FIG. 3G). In some embodiments, the approximate or substantially diamond shape includes curved edge(s) instead of straight edges but still include two pairs of edges that each pair are substantially parallel. In some embodiments, the approximate or substantially hexagon shape includes curved edge(s) instead of straight edge(s). In some embodiments, the approximate or substantially triangular shape includes curved edge(s) instead of straight edges. The adjacent open ends at the most proximal and most distal location of the stent frame when connected and connected with adjacent struts form an approximate triangular shape. In this embodiment, the height of the stent cells increase gradually from the proximal end to the distal end. In some embodiments, the top portion 110 is or includes the flared section. In some embodiments, the bottom portion 130 is or includes the substantially columnar section. In some embodiments, the bottom portion 120 includes the constricted region.

In some embodiments, the dimensions of the stent frame 102 and stent cells 102*a* are when the stent frame is properly deployed or expanded. In some embodiments, the stent frame includes a height in the range of about 25 to 60 mm. In some embodiments, the stent frame includes a height in the range of about 30 to 55 mm. In some embodiments, the stent frame includes a height in the range of about 35 to 50 mm. In some embodiments, the stent includes a cross section (perpendicular to z axis or longitudinal direction) with a diameter of about 15 mm to about 30 mm. In some embodiments, the stent includes a cross section (perpendicular to z axis or longitudinal direction) with a diameter of about 15 mm to about 35 mm. In some embodiments, the stent frame includes a cross section that is larger at the top portion than that at the bottom or mid portions, as shown in FIG. 3H. In some embodiments, the stent frame includes an approximately cylindrical shape as shown in FIGS. 3E-3F. In some embodiments, each stent cell includes a height of about 5 mm to about 25 mm. In some embodiments, each stent cell includes a height of about 6 mm to about 9 mm. In some embodiments, each stent cell includes a height of about 8 mm to about 18 mm. In some embodiments, each stent cell includes a height of about 10 mm to about 18 mm.

In some embodiments, the stent frame herein includes a plurality of expandable stent cells arranged in more than one layer and stacked in a longitudinal direction. In some embodiments, the stent frame comprising a collapsed delivery configuration and an expanded deployed configuration. In some embodiments, the stent frame comprises a substantially columnar section, and a flared section, wherein two or more layers of stent cells are of a substantially diamond shape, and wherein the stent frame comprises non-expandable connectors positioned between the substantially columnar section and the flared section. In some embodiments, the connectors include one or more straight struts and/or one or more struts forming loops. In some embodiments, the connectors are much shorter than the stents in the longitudinal or z direction. In some embodiments, the loops and holes enclosed thereby are for allowing attachment of the expandable skirt, the valve, and/or the tissue skirt. In some embodiments, each of the connectors connects two stent cells that do not share any vertices or edges with each other. In some embodiments, each of the connectors connects a most distal vertex of a first stent cell to a most proximal vertex of a second stent cell that is more distal to the first stent cell.

In some embodiments, additional connectors are included within the substantially columnar section of the stent frame as shown in FIG. 3J.

Figures 3M, 3N, 3O, 3P:
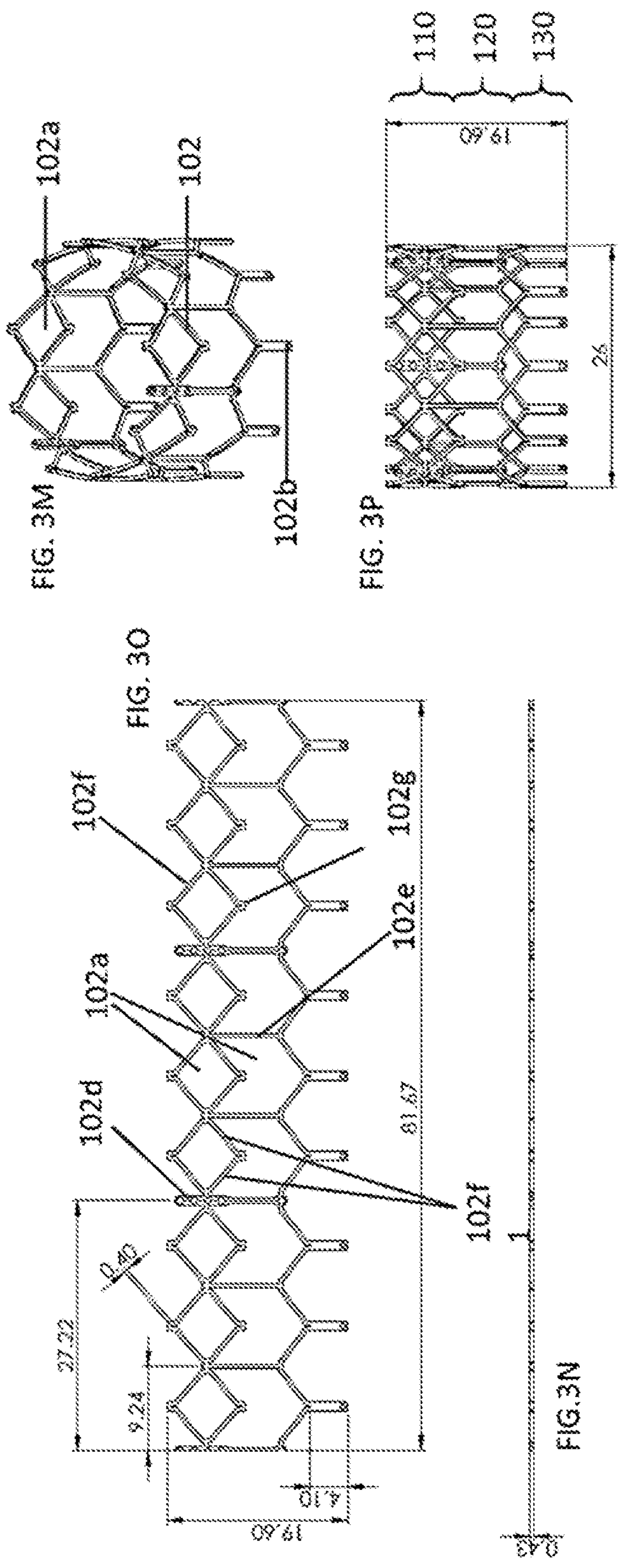
FIGS. 3M-3P show a non-limiting exemplary embodiments of the SAPIEN® stent shown in different views that can be used with the expandable sealing skirt.

SAPIEN® and/or SAPIEN XT® Examples:

FIGS. 3M to 3P show nonlimiting exemplary embodiments of the stent frame herein with different views when the stent frame is properly expanded. In some embodiments, the stent includes one or more portions along the longitudinal direction or z axis. FIGS. 3M and 3P show the stent frame in the perspective view and side view, respectively. FIG. 3P shows the stent frame with the top 110, mid 120, and 130 bottom portions. Referring to FIG. 1G, in some embodiments, the top portion 110 is the most proximal portion while the bottom portion 130 is the most distal portion when the stent frame is properly implanted. In some embodiments, the distal portion is closer to the ventricle than the proximal portion. FIGS. 3N-3O show different views of the stent frame in FIGS. 3M to 3P with the stent frame cut along the longitudinal direction and laid flat as deployed. In this particular embodiment, the stent frame has a diameter of its cross section of about 26 mm when in an expanded configuration, and a height of about 19.66 mm along the longitudinal or z direction. The thickness of the stent frame along the radial direction is about 0.43 mm. In some embodiments, the thickness is the average thickness or the maximal thickness. In some embodiments, the diameter, height, and/or other size determining parameters of the stent frame may be customized to fit for different patients. In this particular embodiment, the strut has a width of about 0.40 mm. The most proximal layer of stent cells has a width of about 9.24 mm for each cell. The most distal struts extending along the longitudinal direction have a height of about 4.10 mm. In this particular embodiment, the stent frame had two layers of stent cells. each cell of the most proximal layer are of a substantially diamond shape as shown in FIG. 3O and sharing one vertex with each of its adjacent cell of the same layer, while each cell of the most distal layer has a hexagon shape and shares two vertices (alternatively referred to as inflections or inflection points) and an edge with each of its adjacent cell of the same layer. The adjacent cells from two layers shares either 2 edges and 2 vertices or only one vertex.

In some embodiments, the vertices or the edges of the distalmost layer of stent cells are coupled or connected to extending legs that extend distally in a direction parallel to the longitudinal axis of the stent, such as is shown in FIGS. 2A-2B. In some embodiments, the vertices or the edges of the distalmost layer of stent cells are coupled or connected to extending legs that extend distally in a direction non-parallel to the longitudinal axis of the stent. In some embodiments, the vertices or the edges of the distalmost layer of stent cells are coupled or connected to extending legs that extend distally in a direction non-parallel to the longitudinal axis of the stent. In some embodiments, the extending legs extend distally beyond the stent layer distalmost vertex or edge. In some embodiments, the stent frame 102 includes one or more layers of stent cells 102*a* stacking along the longitudinal axis or z axis. In some embodiments, the stent cells on the same layer can be identical or different to each other in shape when in the deployed configuration. In some embodiments, adjacent stent cells of the same layer share one or only one vertex (alternatively referred to as inflection or inflection point). In some embodiments, adjacent stent cells of the same layer share two or only two vertices (alternatively referred to as inflections or inflection points). In some embodiments, adjacent stent cells of the same layer share one vertex (alternatively referred to as inflections or inflection points) and an edge. In some embodiments, adjacent stent cells of two different adjacent layers share two vertices (alternatively referred to as inflections or inflection points) and an edge.

In some embodiments, the adjacent stent cells shares at least a vertex or an edge. In some embodiments, the adjacent cells are not separated by any other stent cells therebetween. In some embodiments, the adjacent cells are separated by struts that are not part of the adjacent stent cells. In some embodiments, the adjacent layers are layers that the stent cells from them shares at least a vertex or an edge. In some embodiments, the adjacent layers are separated by struts that are not part of stent cells of the adjacent layers. In some embodiments, the stent cell is of various geometrical shapes. In addition to the closed or contoured cells, in some embodiments, the stent frame includes a layer of open ends proximal to the most proximal layer of closed stent cells. In some embodiments, the stent frame includes a layer of open ends distal to the most distal layer of closed stent cells. When connecting two adjacent open ends, a shape may be formed with the struts from the struts of adjacent stent cells. In some embodiments, this shape is different from that of the closed or contoured stent cells. Referring to FIGS. 3M to 3O, the stent frame includes 2 layers of closed stent cells and one layer of the stent cells are of an approximate or substantially diamond shape. In some embodiments, the approximate or substantially diamond shape includes curved edge(s) instead of straight edges but still include two pairs of edges that each pair are substantially parallel. In some embodiments, the substantially diamond shape includes four legs (in two parallel pairs or non-parallel pairs) that have inflections therebetween. The connecting legs extend from one inflection to the next inflection in a general direction that is parallel to its parallel pair, but is curved rather than straight—when laid flat in the expanded deployed configuration, thus the shape formed by the four legs are referred to as substantially diamond shape or diamond shape herein. Substantially diamond shape or diamond shape may also refer to true diamond shapes having straight edges and two pairs of edges or legs and within each pair there the edges or legs are parallel. The height of the stent cells from the proximal-most inflection to the distal-most inflection decreases gradually from the top portion (proximal) to the bottom portion (distal) of the stent frame. In some embodiments, the approximate or substantially triangular shape includes curved edge(s) or legs instead of straight edges or legs. In some embodiments, the approximate or substantially triangular shape includes an inflection or vertex therebetween connecting two legs; open ends at the most proximal and most distal location of the stent frame when connected and connected with adjacent struts can form an approximate triangular shape or pentagon shape. In this embodiment, the height of the stent cells increase gradually from the proximal end to the distal end.

In some embodiments, the dimensions of the stent frame 102 and stent cells 102*a* are when the stent frame is in the deployed or expanded configuration. In some embodiments, the stent frame includes a height in the range of about 15 to 45 mm. In some embodiments, the stent frame includes a height in the range of about 18 to 40. In some embodiments, the stent frame includes a height in the range of about 18 to 30. In some embodiments, the stent includes a cross section (perpendicular to z axis or longitudinal direction) with a diameter of about 20 mm to about 30 mm in an expanded deployed configuration. In some embodiments, the stent includes a cross section (perpendicular to z axis or longitudinal direction) with a diameter of about 25 mm to about 35 mm.

In some embodiments, the stent frame includes a cross section that is substantially consistent along the longitudinal direction, as shown in FIG. 3P. In some embodiments, the stent frame includes an approximately cylindrical shape as shown in FIGS. 3M-3N. In some embodiments, each stent cell includes a height of about 5 mm to about 20 mm in an expanded deployed configuration. In some embodiments, each stent cell includes a height of about 6 mm to about 9 mm in an expanded deployed configuration. In some embodiments, each stent cell includes a height of about 8 mm to about 10 mm in an expanded deployed configuration. In some embodiments, each stent cell includes a height of about 14 mm to about 18 mm in an expanded deployed configuration.

Referring to FIGS. 1K, 1M and FIGS. 3M-3P, in particular embodiments, the stent frame 102 is tubular. In some embodiments, the stent frame has a circular cross section (orthogonal to the longitudinal or z direction) in the expanded deployed configuration. In some embodiments, the stent frame has a plurality of angularly spaced longitudinal commissure attachment posts 102*d*, a plurality of stent cells 102*a* formed by a plurality of longitudinal struts 102*e* and rows of circumferential struts 102*f* extending between and interconnecting the plurality of longitudinal struts. In some embodiments, the longitudinally struts 102*e* are rigid beams of fixed length. In some embodiments, the rows of circumferential struts 102*f* form annularly spaced expandable web-like portions extending and connected between the support beams. In some embodiments, a valve is attached to the plurality of commissure attachment posts 102*d*. In these embodiments, an expandable sealing skirt 101 is annular and coupled to the stent frame at or near a distal end of the stent frame, the expandable sealing skirt comprising a protruding region 101*a* configured to expand radially past the plurality of stent cells 102*a* of the stent frame when the device assembly is in the expanded deployed configuration and a non-protruding region, In some embodiments, the rows of circumferential struts 102*f* includes at least a first row of circumferential struts adjacent the distal end (bottom) of the valve and a second row of circumferential struts adjacent a proximal end (top) of the valve, wherein the struts of the first row are thicker than the struts of the second row. In other words, the diameter, width, and/or length of the circumferential struts are larger in the first row than that of the second row. In some embodiments, at least one row of circumferential struts includes pairs 102*f*1 of circumferential struts extending between two longitudinal struts, the struts of each pair having adjacent ends interconnected by a generally U-shaped crown portion 102*g* defining a gap between the adjacent ends. In some embodiments, an angle between each pair of struts connected by the U-shaped portion is between about 90 and 110 degrees. In some embodiments, the stent frame comprises a nickel cobalt chromium alloy. In some embodiments, the nickel cobalt chromium alloy comprises MP35N. In some embodiments, the stent frame 102 further comprising a reinforcing bar positioned against flaps of the valve for reinforcing the attachments between commissures of the valve and the commissure attachment posts 102*d*. In some embodiments, the stent frame 102 further comprising a reinforcing bar that sandwiches commissures of the valve and the commissure attachment posts 102*d*.

ACURATE® Example:

FIGS. 1N-1P show nonlimiting exemplary embodiments of the stent frame 102 herein with different views when the stent frame is in the expanded deployed configuration. In some embodiments, the stent frame include more than one stent cells 102*a* contoured by one or more stent struts 113 and arranged in one or more layers. In some embodiments, the stent frame has three layers of stent cells from its proximal end to its distal end. The most proximal layer (top most layer) include stent cells that are of a shape with 12 legs. Among these 12 legs, 6 at its distal portion are shared with adjacent layer of stent cells more distal to it. The 6 shared legs can be equal in length. Adjacent stent cells of this layer share at least two support beams with each other. The second layer or middle layer of FIGS. 1N-1P have stent cells of at least two different shapes, one shape is substantially diamond (when projected onto a two dimensional plane), the other shape is a substantially concave hexagon. The first layer or most distal layer includes stent cells that are substantially diamond. In some embodiments, such as in the embodiment of FIGS. 1N-1P, the stent frame forms a zig-zag shape at the distal end of diamond stent cells and/or another zig-zag shape at the proximal end of stent cells. The sizes of stent cells of the most distal layer are substantially identical when the cells are laid flat and expended. In some embodiments, the vertices or the edges of the distalmost layer of stent cells are coupled or connected to extending legs that extend distally in a direction non-parallel to the longitudinal axis of the stent. In some embodiments, the vertices or the edges of the distalmost layer of stent cells are coupled or connected to extending legs that extend distally in a direction non-parallel to the longitudinal axis of the stent. In some embodiments, the extending legs extend distally beyond the stent layer distalmost vertex or edge.

In some embodiments, the sizes of stent cells of the distalmost layers are substantially identical. In some embodiments, the sizes of stent cells of the distalmost layers are smallest at the middle layer. In some embodiments, the stent frame has a height of about 50-70 mm, the top layer of stent cells has a height of about 20-40 mm while the bottom layer of stem cells includes a height of about 8-15 mm. The diameter of the stent cross section (perpendicular to z axis or longitudinal direction) is about 20-30 mm, and the strut includes a thickness of about 0.4 to about 1.5 mm along the radial direction.

In some embodiments, the diameter, height, and/or other size determining parameters may be customized to fit for different patients.

In some embodiments, the most distal layer includes stent cells of a substantially identical shape. In some embodiments, the stent cells are substantially diamond. In some embodiments, the layer adjacent the most distal layer includes cells of two different shapes, e.g., substantially diamond (with bending or flaring out) and substantially hexagon (having 6 legs or arms or edges). When the stent frame is in the expanded deployed configuration, at least a portion of the stent cells (e.g., a proximal portion) in the layer that is adjacent and proximal to the most distal layer may flare outwardly along the radial direction as shown in FIG. 1P. In this embodiments, the flare-out or bending portion includes at least a portion of the distal-facing legs of the substantially diamond shape. The substantially diamond (with bending or flaring out) shape becomes a substantially diamond shape when laid flat in a plane. In some embodiments, the stent frame includes a third layer of cells that is most proximal among the three layers. As shown in FIG. 1P, the stent cells of this third layer have a substantially identical shape, which is a random or an irregular shape with 12 legs or arms. Each cell of this third layer may include two supporting beams 108*a* extending longitudinally and substantially parallel to each other. In some embodiments, the adjacent cells of the third layer shares one supporting beam. The supporting beam may include attachment element such as loops for of a valve to the stent frame. Each cell of this third layer may include 6 legs or arms or struts from an adjacent layer distal to the third layer. These 6 legs may be connected by inflections and equal in length. In this embodiment, the 6 legs are from the distal half of three adjacent stent cells of the adjacent layer distal to the third layer. Each cell of this third layer may include a proximal half with two most proximal legs 108*b* that may optionally flare outwardly in the radial direction. The two most proximal legs are connected by a U-shape inflection/vertex.

In some embodiments, the dimensions of the stent frame 102 and stent cells 102*a* are when the stent frame is in the deployed configuration. In some embodiments, the stent frame includes a height in the range of about 35 to 70 mm. In some embodiments, the stent frame includes a height in the range of about 30 to 65. In some embodiments, the stent includes a cross section (perpendicular to z axis or longitudinal direction) with a diameter of about 20 mm to about 30 mm. In some embodiments, the stent includes a cross section (perpendicular to z axis or longitudinal direction) with a diameter of about 25 mm to about 35 mm in an expanded deployed configuration, optionally measured at the distal end of the stent frame or proximal end of the stent frame. In some embodiments, the stent frame includes a cross section that is larger at the middle portion than that at the bottom or at the top portion, as shown in FIG. 1P. In some embodiments, the stent frame includes an approximately cylindrical shape as shown in FIGS. 4M-4N. In some embodiments, each stent cell of a layer includes a height of about 5 mm to about 20 mm in an expanded deployed configuration. In some embodiments, each stent cell of a layer includes a height of about 6 mm to about 9 mm in an expanded deployed configuration. In some embodiments, each stent cell of a layer includes a height of about 6 mm to about 12 mm in an expanded deployed configuration. In some embodiments, each stent cell of a layer includes a height of about 8 mm to about 12 mm in an expanded deployed configuration. In some embodiments, each stent cell of a layer includes a height of about 10 mm to about 18 mm in an expanded deployed configuration. In some embodiments, each stent cell of a layer includes a height of about 9 mm to about 16 mm in an expanded deployed configuration. In some embodiments, each stent cell of a layer includes a height of about 9 mm to about 14 mm in an expanded deployed configuration. In some embodiments, each stent cell of a layer includes a height of about 20 mm to about 40 mm in an expanded deployed configuration. In some embodiments, each stent cell of a layer includes a height of about 25 mm to about 35 mm in an expanded deployed configuration.

In some embodiments, the stent frame comprises multiple stent cells which have a cell pattern defined by unequal length zig-zagging struts that connect in closed cells at inflection points to adjacent zig-zagging struts. The inflection points may not be true connections but may be laser cut to form this pattern of legs and inflections forming substantially diamond shaped cells. In some embodiments, one layer of stent cells are of a substantially diamond shape.

Procedure of Implantation

In some embodiments, the device is deployed by means of a movement of the catheter tubing (e.g., proximally and away from the ventricle) to release the device from the catheter; a movement of the catheter tubing (e.g., distally and toward the ventricle) during the deployment procedure; or a combination of the two. In some embodiments, the bottom part of the device 130 is deployed first with the catheter (sheath) moving away (e.g., proximally) from the ventricle and while the bottom part 130 remains deployed and relatively stable with the native aortic valve annulus or ventricle (or the left ventricular outflow tract) the top portion of the device 110 is deployed by the catheter (sheath) moving further away from the ventricle. In this embodiment, the device is recaptured or equivalently herein resheathed, in the reverse steps.

In some embodiments, the device is deployed starting with the bottom section 130 first, followed by the middle 120, and then the top 110 part—all by moving the catheter (sheath) in the direction away from the ventricle i.e. towards the operator. In the same embodiment, recaptured or resheathed is in the reverse steps. In some embodiments, the device is deployed by a combination of maneuvers such as deploying bottom section 130 first by moving the catheter towards the ventricle, followed by deployment of the mid 120 and top 110 sections of the device by moving the catheter away from the ventricle. The combination could also include deployment the mid-section 120 first by moving the catheter (sheath) away from the ventricle, then followed by the bottom section 130 by moving the catheter (or part of the catheter) towards the ventricle and then the top section 110 by moving the catheter (sheath) away from the ventricle.

In some embodiments, the expandable skirt includes circumferential extensions on individual cells 105 that extend over the stent strut 102*c* thickness or width. Such circumferential extensions may potentially further enhance the sealing capacity by further preventing blood to flow through the channels formed by the stent struts 102*c*.

In some embodiments, the deployed state is equivalent to expanded state or unsheathed stated herein. In some embodiments, the undeployed state is equivalent to compressed stated, collapsed state, sheathed state, or resheathed state, herein.

In some embodiments, the device assembly herein has a collapsed delivery configuration and an expanded deployed configuration. In some embodiments, each of the expandable skirt, the stent frame, and the valve include a collapsed delivery configuration and an expanded deployed configuration. In some embodiments, the device assembly is in the same configuration as its structural elements such as the stent frame, stent cells, skirts, the protruding region, the valve, etc.

Foam of the Expandable Skirt

In some embodiments, the foam of the expandable skirt described herein including the protruding region, the foam cells of the protruding region, the connection regions of the protruding region, and the non-protruding region, has a controlled porosity. In some embodiments, the foam of the expandable skirt described herein, including one or more of the protruding region, the foam cells of the protruding region, the connection regions of the protruding region, and the non-protruding region, has a uniform porosity. In some embodiments, the foam of the expandable skirt described herein, including one or more of the protruding region, the foam cells of the protruding region, the connection regions of the protruding region, and the non-protruding region, has a variable porosity. In some embodiments, the foam of the expandable skirt described herein including one or more of the protruding region, the foam cells of the protruding region, the connection regions of the protruding region, and the non-protruding region, has an open pore structure, a closed pore structure, or a combination. In some embodiments, the foam of the expandable skirt described herein, including one or more of the protruding region, the foam cells of the protruding region, the connection regions of the protruding region, and the non-protruding region, has a porosity of about 5-500 μm. In some embodiments, the foam of the expandable skirt described herein, including one or more of the protruding region, the foam cells of the protruding region, the connection regions of the protruding region, and the non-protruding region, has a porosity of about 5-500 μm. In some embodiments, the foam of the expandable skirt described herein, including one or more of the protruding region, the foam cells of the protruding region, the connection regions of the protruding region, and the non-protruding region, has a porosity of about 5-450 μm. In some embodiments, the foam of the expandable skirt described herein, including one or more of the foam cells, the protruding region, the foam cells of the protruding region, the connection regions of the protruding region, and the non-protruding region, has a porosity of about 5-400 μm. In some embodiments, the foam of the expandable skirt described herein, including one or more of the protruding region, the foam cells of the protruding region, the connection regions of the protruding region, and the non-protruding region, has a porosity of about 5-350 μm. In some embodiments, the foam of the expandable skirt described herein, including one or more of the protruding region, the foam cells of the protruding region, the connection regions of the protruding region, and the non-protruding region, has a porosity of about 5-300 μm. In some embodiments, the foam of the expandable skirt described herein, including one or more of the protruding region, the foam cells of the protruding region, the connection regions of the protruding region, and the non-protruding region has a porosity of about 5-250 μm. In some embodiments, the foam of the expandable skirt described herein, including one or more of the protruding region, the foam cells of the protruding region, the connection regions of the protruding region, and the non-protruding region has a porosity of about 5-200 μm.

In some embodiments, the foam disclosed herein of the expandable skirt described herein, including one or more of the protruding region, the foam cells of the protruding region, the connection regions of the protruding region, and the non-protruding region is cast using one or more molds. In some embodiments, the process for the preparation of a foam of the expandable skirt, including one or more of the protruding region, the foam cells of the protruding region, the connection regions of the protruding region, and the non-protruding region includes one or more steps selected from: dissolving a polymer material in a solvent to form a polymer solution; adding the polymer solution to a mold, and optionally degassing the polymer solution in the mold; adding a solid particulate to the top of the polymer solution in the mold; and washing the resulting polymer mixture in the mold with a washing liquid; wherein the solid particulate is insoluble in the polymer solution and soluble in the washing liquid, and wherein after washing the polymer mixture with the washing liquid, the remaining polymer material in the mold forms the foam and the shape of the foam is defined by the shape of the mold.

In some embodiments, the foam disclosed herein of the expandable skirt described herein, including one or more of the protruding region, the foam cells of the protruding region, the connection regions of the protruding region, and the non-protruding region is made of polymer material. In some embodiments, the polymer material is pre-polymerized polymer pellets. In some embodiments, the polymer material is polyurethane pellets. In some embodiments, the foam of the expandable skirt described herein, including one or more of the protruding region, the foam cells of the protruding region, the connection regions of the protruding region, and the non-protruding region disclosed herein is made of a polymer solution. In some embodiments, the solvent is selected from dimethyl sulfoxide (DMSO), tetrahydrofuran (THF), dimethylformamide (DMF), dimethylacetamide (DMAc), and a combination thereof. In some embodiments, the solvent is DMSO. In some embodiments, the solvent is THF. In some embodiments, the solvent is DMF. In some embodiments, DMAc. In some embodiments, the solvent is a combination of DMSO and THF. In some embodiments, the solid particulate is sodium chloride. In some embodiments, the solid particulate is sugar. In some embodiments, the mold is a silicon mold, a Teflon mold, or an aluminum mold.

Example 1: Foam Casting Procedure Using DMSO

DSM Carbosil 80A and 55D Pellets are stored in a desiccator at approximately room temperature, at moisture content ranging from of 30-33%. Silica gel beads are used to absorb the moisture in a desiccant cabinet.

Polymer solutions are made by dissolving polyurethane (PU) pellets in DMSO with around 5-25% TDS. The pellets were dissolved by adding solvent on top of pellets in a Pyrex bottle with Teflon cap stirring on a magnetic stirrer at room temperature. Depending on the polymer concentration, complete dissolution takes 20-80 hours.

A mother mold of a pattern of protruding cells reflecting one or more of the layers of stent frame cells in their expanded configuration at or distal to the constriction region (region that includes the valve attached to the stent frame and is configured to be delivered to the native valve annulus) of a transcatheter valve bioprosthesis (alternatively called a stent frame and valve attached thereto) to be cast is first designed by a 3D modelling software, e.g. Solidworks, and printed using a 3D printer. In order to produce protruding cells that will protrude through the one or more layers of the stent frame radially away from a central longitudinal axis of the transcatheter valve bioprothesis and at or distal to the native valve annulus (at least) when the device assembly with the expandable skirt attached thereto is delivered for implantation in the subject's heart as a replacement valve. The protruding region has connection regions between the protruding cells aligning with the stent frame that connect the protruding cells. Thus, the mother mold, in some embodiments, also includes connection region mold regions between the protruding cell mold regions, and the connection regions in such embodiments is made from the foam as described herein, concurrently with the protruding cell manufacture. In some embodiments, the connection regions are not foam, or are not entirely foam. In such embodiments the connection regions of the protruding regions are created according to Example 2. Then, a negative of the desired pattern of protruding cells (and optionally, the connection regions of the protruding region) is made using a silicon mold from an appropriate castable silicone e.g. PinkySil®.

The silicon mold is preheated at temperature between 40-100° C. for at least half an hour. The polymer solution which has been stored at room temperature is added to the silicon mold to fill the mold until it overflows. The amount of solution depends on the mold size and is optimized for each mold. The solution may be pre-heated, if necessary.

The solution in the silicon mold may be degassed in a vacuum oven at 30-90° C. for up to 1 hour (vacuum up to 300 mbar). Salt is weighed and then added on top of the optionally degassed solution in the mold. The ratio of the salt to solution is optimized for different molds. This step can be done either manually or using an automated means.

The sample is removed from oven/vacuum oven and sunk in hot tap water in order to wash out the DMSO. Washing also leaches out the salt so that the remaining polymer material forms the scaffold of the foam. Upon removal of the salt crystals all that remains is the hardened polymer with open holes/pores where the salt once was.

The protruding region including layer(s) of protruding cells made of foam, are removed from the silicon molds and are stored in tap water in 120 mL containers. The protruding region may be trimmed thereafter, or not. In some embodiments, the protruding region is trimmed distal to the protruding cells, so as not to extend beyond the distal-most portions of the stent frame. In some embodiments, the protruding region is formed to sit below (i.e. distal to) the stent frame. In some embodiments, protruding cells are formed which are below (i.e. distal to) the stent frame. In some embodiments, the protruding cells that are below (i.e. distal to) the stent frame are not enclosed by or surrounded by any expandable stent cell. The protruding region is then attached to the stent frame of the device assembly such that the protruding cells are aligned with the expandable stent cells of the one or more layers of the stent frame and protrude therethrough when the device assembly is in its expanded deployed configuration. The attachments are described herein, such as by suturing with sutures.

In some embodiments, the non-protruding region is also made in the same manner and concurrently with the protruding cells as described in this example. In some embodiments, the non-protruding region and the protruding region including the protruding cells and one or more connection regions therebetween are made from the foam as described herein. In some embodiments, the non-protruding region and the protruding region (including the protruding cells and one or more connection regions therebetween and one or more connecting cells) are made from the foam as described herein.

Example 2: Foam Casting Procedure Using DMSO Including Use of PET Mesh

Figure 9:
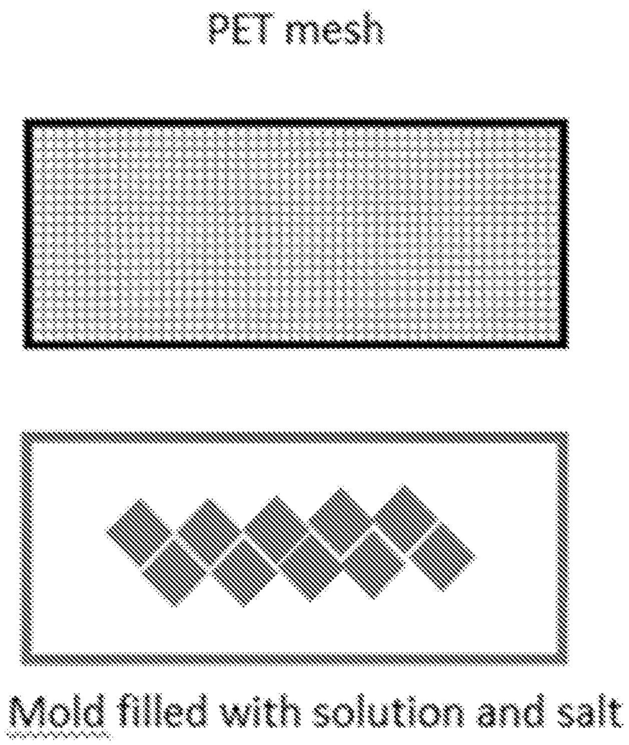
FIG. 9 depicts the addition of a PET mesh as the non-protruding region on top of the mold of the protruding region during casting of the foam expandable sealing skirt.

In some embodiments wherein the protruding region is used as a transcatheter heart valve skirt, the use of a PET mesh as the non-protruding region is included in the casting process. Following the addition of salt to the polymer solution in the mold as outlined in Example 1, PET mesh is cut to a size that is at least as large as the mold of the protruding region and then it is preheated in oven at 50-100° C. for at least half an hour. The PET mesh is placed on top of the mold (FIG. 9) and the mold/PET mesh sample is heated at 30-90° C. for up to an hour. The sample is removed from oven/vacuum oven and sunk in hot tap water in order to wash out the DMSO. Washing also leaches out the salt so that the remaining polymer material forms the scaffold of the foam. Upon removal of the salt crystals, what remains is the hardened polymer foam with the PET mesh attached to the foam surface, optionally permanently. The PET mesh thereafter can be used as the non-protruding region by itself or with the foam-cast non-protruding region described in Example 1. The PET mesh attached to the foam cells as described herein can be used as the connecting regions between the protruding foam cells of the protruding region by itself when there are no or intermittent foam connection regions. Alternatively, the PET mesh attached to the foam cells as described herein can be used in addition to the foam as the connecting regions between the protruding foam cells of the protruding region.

Example 3: Foam Casting Procedure Using THF

DSM Carbosil 80A and 55D Pellets are stored in a desiccator at approximately room temperature, at moisture content ranging from of 30-33%. Silica gel beads are used to absorb the moisture in a desiccant cabinet.

Two polymer solutions are made by dissolving polyurethane (PU) pellets in THF; a higher concentration solution in the range of 8-15% (w/v) and a lower concentration solution in the range of 0.5-6% (w/v). The pellets were dissolved by adding solvent on top of pellets in a Pyrex bottle with Teflon cap stirring on a magnetic stirrer at room temperature.

A mother mold of a pattern of protruding cells reflecting one or more of the layers of stent frame cells in their expanded configuration at or distal to the constriction region (region that includes the valve attached to the stent frame and is configured to be delivered to the native valve annulus) of a transcatheter valve bioprosthesis (alternatively called a stent frame and valve attached thereto) to be cast is first designed by a 3D modelling software, e.g. Solidworks, and printed using a 3D printer in order to produce protruding cells that will protrude through the one or more layers of the stent frame radially away from a central longitudinal axis of the transcatheter valve bioprothesis and at or distal to the native valve annulus (at least) when the device assembly with the expandable skirt attached thereto is delivered for implantation in the subject's heart as a replacement valve. The protruding region has connection regions between the protruding cells aligning with the stent frame that connect the protruding cells. Thus, the mother mold, in some embodiments, also includes connection region mold regions between the protruding cell mold regions, and the connection regions in such embodiments is made from the foam as described herein, concurrently with the protruding cell manufacture. In some embodiments, the connection regions are not foam, or are not entirely foam. In such embodiments the connection regions of the protruding regions are created according to Example 2. Then, a negative of the desired pattern of protruding cells (and optionally, the connection regions of the protruding region) is made using a silicon mold from an appropriate castable silicone e.g. PinkySil®.

A thin layer of PU (poly-urethane?) is created on the silicon mold using the lower concentration PU/THF solution. When the thin layer of PU is dried, salt is added to the silicon mold to fill the spaces completely.

The higher concentration polymer THF solution is added to the silicon mold to cover the salt completely (the volume of polymer solution is optimised for each design of silicon mold and is kept consistent between samples).

The mold is left under a fume hood for at least 30 minutes so that the polymer solution diffuses into the structure of foam. The sample is covered with a glass beaker to minimize the evaporation of solvent during this time.

The mold is placed in a vacuum oven at 50° C. for a minimum of 12 hours to remove the solvent and obtain a solid structure of foam.

The sample is removed from oven/vacuum oven and washed with water until the salt is fully dissolved and removed.

The protruding region including protruding cells made of foam, are removed from the silicon molds and are kept wet in PBS (Phosphate buffer saline). The protruding region may be trimmed thereafter, or not. In some embodiments, the protruding region is trimmed distal to the protruding cells, so as not to extend beyond the distal-most portions of the stent frame. In some embodiments, the protruding region is formed to sit below (i.e. distal to) the stent frame. In some embodiments, protruding cells are formed which are below (i.e. distal to) the stent frame. In some embodiments, the protruding cells that are below (i.e. distal to) the stent frame are not enclosed by or surrounded by any expandable stent cell. The protruding region is then attached to the stent frame of the device assembly such that the protruding cells are aligned with the expandable stent cells of the one or more layers of the stent frame and protrude therethrough when the device assembly is in its expanded deployed configuration. The attachments are described herein, such as by suturing with sutures.

In some embodiments, the non-protruding region is also made in the same manner and concurrently with the protruding cells as described in this example. In some embodiments, the non-protruding region and the protruding region including the protruding cells and one or more connection regions therebetween are made from the foam as described herein. In some embodiments, the non-protruding region and the protruding region including the protruding cells and one or more connection regions therebetween and one or more connecting cells are made from the foam as described herein.

Example 4: Foam Casting Procedure Using THF Including Use of PET Mesh

In some embodiments wherein the protruding region is used as a transcatheter heart valve skirt, the use of a PET mesh as the non-protruding region is included in the casting process. Following the addition of salt to the polymer solution in the mold as outlined in Example 3, PET mesh is cut as the same size of the mold and then it is preheated in oven at 50-100° C. for at least half an hour. The PET mesh is placed on top of the mold and an additional layer of the higher concentration polymer THF solution is added to the mold/PET mesh sample to obtain a uniform distribution of polymer solution on the surface. The mold/PET mesh sample is heated at 30-90° C. for up to an hour. The sample is removed from oven/vacuum oven and washed with water until the salt is fully dissolved and removed. Upon removal of the salt crystals, what remains is the hardened polymer foam with the PET mesh attached to the foam surface, optionally permanently. The PET mesh thereafter can be used as the non-protruding region by itself or with the foam-cast non-protruding region described in Example 3. The PET mesh attached to the foam cells as described herein can be used as the connection regions between the protruding foam cells of the protruding region by itself when there are no or intermittent foam connection regions. Alternatively, the PET mesh attached to the foam cells as described herein can be used in addition to the foam as the connecting regions between the protruding foam cells of the protruding region. In some embodiments, the PET mesh attached to the foam cells as described herein can be used in addition to the foam as the connecting cells between the protruding foam cells of the protruding region.

Example 5: Foam Casting Procedure Using Co-Solvents

Foams are manufactured using the processes outlined in Examples 1-4, but a combination on DMSO and THF is used to prepare the polymer solution. The ratio of DMSO to THF can be varied. Use of various co-solvent ratios allows for solutions with higher concentration of polymer and lower viscosity and as a result foams with different mechanical properties.

In some embodiments, the expandable foam skirt including nonprotruding region and the protruding region may then be attached to the stent frame using attachment methods, such as suturing, optionally when the foam skirt is in the expanded configuration. In some embodiments, after attachment, the foam skirt, the stent frame, and other elements of the device assembly can be sheathed into a delivery catheter, thus ready for delivery and implantation.

Unless otherwise defined, all technical terms used herein have the same meaning as commonly understood by one of ordinary skill in the art to which this disclosure belongs. As used in this specification and the appended claims, the singular forms "a," "an," and "the" include plural references unless the context clearly dictates otherwise. Any reference to "or" herein is intended to encompass "and/or" unless otherwise stated. As used in this specification and the claims, unless otherwise stated, the term "about," "substantially," and "approximately" refers to variations of less than or equal to +/−1%, +/−2%, +/−3%, +/−4%, +/−5%, +/−6%, +/−7%, +/−8%, +/−9%, +/−10%, +/−11%, +/−12%, +/−14%, +/−15%, or +/−20% of the numerical value depending on the embodiment. As a non-limiting example, about 100 meters represents a range of 95 meters to 105 meters (which is +/−5% of 100 meters), 90 meters to 110 meters (which is +/−10% of 100 meters), or 85 meters to 115 meters (which is +/−15% of 100 meters) depending on the embodiments.

While preferred embodiments disclosed herein have been shown and described herein, it will be obvious to those skilled in the art that such embodiments are provided by way of example only. Numerous variations, changes, and substitutions will now occur to those skilled in the art without departing from the disclosure herein. It should be understood that various alternatives to the embodiments of the device assemblies described herein may be employed in practicing the device assemblies herein. It is intended that the following claims define the scope of the device assemblies herein and that methods and structures within the scope of these claims and their equivalents be covered thereby.

What is claimed is:

1. A device assembly for endovascular prosthesis implantation in a human patient, the device assembly comprising a collapsed delivery configuration and an expanded deployed configuration, and the device assembly comprising, when in the expanded deployed configuration:

a) a stent frame comprising
  a first layer of first expandable stent cells and a second layer of second expandable stent cells;
b) a valve attached to the stent frame; and
c) an expandable sealing skirt coupled to the stent frame, the expandable sealing skirt comprising a protruding layer and a non-protruding layer integral with and backing the protruding layer in the radial direction, the protruding layer comprising an expandable material having an inner surface integral with and extending radially outward from an outer surface of the non-protruding layer, wherein the expandable material has a thickness in the radial direction, from the inner surface thereof to an outer surface thereof, greater than that of the non-protruding layer.

2. The device assembly of claim 1, wherein the thickness of the expandable material along the radial direction is spatially variable at least along a longitudinal direction.

3. The device assembly of claim 1, wherein the protruding layer comprises a plurality of protruding cells and connecting regions between the protruding cells, wherein the protruding cells comprise the expandable material of the protruding layer.

4. The device assembly of claim 3, wherein the protruding cells and connecting regions are arranged in a pattern reflecting a stent cell pattern of the stent frame.

5. The device assembly of claim 3, wherein the protruding cells extend through one or more of the first expandable stent cells in the first layer.

6. The device assembly of claim 3, wherein the connecting regions are coincident with one or more legs of said expendable stent cells, or are coincident with at least one or more inflections of said expendable stent cells, or a combination thereof.

7. The device assembly of claim 3, wherein the connecting regions are coincident with a portion of one or more legs of said expendable stent cells, or are coincident with a portion of at least one or more inflections of said expendable stent cells, or a combination thereof.

8. The device assembly of claim 3, wherein when the device assembly is in the expanded deployed configuration, one or more of the protruding cells comprises a cross section along a radial direction that is substantially a triangle or rectangle.

9. The device assembly of 3, wherein the protruding layer forms a protruding ring.

10. The device assembly of claim 9, wherein the protruding ring when viewed longitudinally from the proximal to distal end of the protruding layer, has protruding cells around an entire circumference of the protruding layer.

11. The device assembly of claim 3, wherein the protruding cells, the connecting region, or both, comprises foam.

12. The device assembly of claim 11, wherein the foam has an open pore structure, a closed pore structure, or a combination.

13. The device assembly of claim 11, wherein the foam has a controlled porosity.

14. The device assembly of claim 11, wherein the foam has a uniform porosity.

15. The device assembly of claim 11, wherein the foam has a variable porosity.

16. The device assembly of claim 11, wherein the foam has a porosity of about 5-500 μm.

17. The device assembly of claim 1, wherein the stent frame comprises a top or proximal portion, and a bottom or distal portion.

18. The device assembly of claim 17, wherein the top portion is more proximal than the bottom portion.

19. The device assembly of claim 17, wherein the stent frame comprises a cross section that is substantially circular at the bottom portion or at the first layer of stent cells.

20. The device assembly of claim 3, wherein the protruding cells are self-expanding.

21. The device assembly of claim 1, wherein the expandable material is self-expandable.

22. The device assembly of claim 1, wherein the expandable material of the protruding layer comprises a foam and the non-protruding layer comprises a mesh or foam mesh.

23. The device assembly of claim 1, wherein the protruding layer and the non-protruding layer are made of different materials.

24. The device assembly of claim 1, wherein the protruding layer and the non-protruding layer comprise the same material.

25. The device assembly of claim 1, wherein a maximal protruding thickness of the protruding layer along the radial direction is about 10% to about 3500% of a thickness of the non-protruding layer.

26. The device assembly of claim 1, wherein a maximal protruding thickness of the protruding layer along the radial direction is in a range of 0.1 mm to 10 cm.

27. The device assembly of claim 1, wherein the outer surface of the non-protruding layer is permanently integrated with the expandable material of the protruding layer.

28. The device assembly of claim 1, wherein the stent frame further comprises a plurality of rigid support beams of fixed length that extend longitudinally.

29. The device assembly of claim 28, wherein the valve is attached to the stent frame at the plurality of support beams.

30. The device assembly of claim 28, wherein the plurality of support beams are provided with bores for allowing attachment of the valve or the expandable sealing skirt thereto.

31. The device assembly of claim 1, wherein the expandable sealing skirt is coupled to the valve.

32. The device assembly of claim 1, wherein each expandable stent cell of the first or second expandable stent cells comprises a substantially diamond shape.

33. The device assembly of claim 1, wherein the stent frame comprises at least a third layer, and where the protruding layer does not extend beyond the first layer of first expandable stent cells, the second layer of second expandable stent cells, or both.

34. The device assembly of claim 1, wherein the expandable material of the protruding layer comprises a foam.

35. The device assembly of claim 34, wherein the foam has a porosity of about 5-500 μm.

36. The device assembly of claim 1, wherein the non-protruding layer is configured to prevent the expandable material of the protruding layer from bulging inward along the radial direction.

37. The device assembly of claim 1, wherein the non-protruding layer is configured to provide a flat backing of the protruding layer.

38. The device assembly of claim 3, wherein the non-protruding layer is configured to provide a flat backing of the plurality of protruding cells.

* * * * *